(12) United States Patent
Whiteford et al.

(10) Patent No.: US 7,438,833 B2
(45) Date of Patent: Oct. 21, 2008

(54) ORGANIC SPECIES THAT FACILITATE CHARGE TRANSFER TO OR FROM NANOSTRUCTURES

(75) Inventors: Jeffery A. Whiteford, Belmont, CA (US); Mihai A. Buretea, San Francisco, CA (US); Erik C. Scher, San Francisco, CA (US)

(73) Assignee: Nanosys, Inc., Palo Alto, CA (US)

( * ) Notice: Subject to any disclaimer, the term of this patent is extended or adjusted under 35 U.S.C. 154(b) by 396 days.

(21) Appl. No.: 11/130,303

(22) Filed: May 16, 2005

(65) Prior Publication Data
US 2005/0205850 A1 Sep. 22, 2005

Related U.S. Application Data

(62) Division of application No. 10/656,910, filed on Sep. 4, 2003, now Pat. No. 6,949,206.

(60) Provisional application No. 60/452,232, filed on Mar. 4, 2003, provisional application No. 60/408,722, filed on Sep. 5, 2002.

(51) Int. Cl.
C08G 61/00 (2006.01)
C07C 13/28 (2006.01)
C07D 497/12 (2006.01)
H01B 1/12 (2006.01)
H05B 33/00 (2006.01)

(52) U.S. Cl. ............... 252/500; 252/299.3; 252/301.32; 252/301.36; 528/101; 528/377; 528/398; 564/75; 564/155; 568/58; 562/8; 562/23; 549/41

(58) Field of Classification Search ............... None
See application file for complete search history.

(56) References Cited

U.S. PATENT DOCUMENTS

| | | | |
|---|---|---|---|
| 5,504,323 A | 4/1996 | Heeger et al. | |
| 5,505,928 A | 4/1996 | Alivisatos et al. | |
| 5,690,807 A | 11/1997 | Clark, Jr. et al. | |
| 5,728,487 A | 3/1998 | Gratzel et al. | |
| 5,751,018 A | 5/1998 | Alivisatos et al. | |
| 5,897,945 A | 4/1999 | Lieber et al. | |
| 5,990,479 A | 11/1999 | Weiss et al. | |

(Continued)

FOREIGN PATENT DOCUMENTS

| | | |
|---|---|---|
| EP | 1170273 A | 1/2002 |
| EP | 1215205 A | 6/2002 |
| WO | WO-02017362 | 2/2002 |
| WO | WO-02080280 | 10/2002 |
| WO | WO-04022637 | 3/2004 |
| WO | WO-04023527 | 3/2004 |

OTHER PUBLICATIONS

Burillo et al, "Studies on salts of Amine-containing polymers with benzoic acids. III. Poly(N,N-dimethylaminoethylmethacrylate-g-polyethylene) with benzoic acids," J. Appl. Poly. Sci., 2000, 78, 972-978.*

(Continued)

*Primary Examiner*—Stanley Silverman
*Assistant Examiner*—Kallambella Vijayakumar
(74) *Attorney, Agent, or Firm*—Andrew L. Filler

(57) ABSTRACT

The present invention provides compositions (small molecules, oligomers and polymers) that can be used to modify charge transport across a nanocrystal surface or within a nanocrystal-containing matrix, as well as methods for making and using the novel compositions.

6 Claims, 31 Drawing Sheets

U.S. PATENT DOCUMENTS

| | | | |
|---|---|---|---|
| 5,997,832 | A | 12/1999 | Lieber et al. |
| 6,036,774 | A | 3/2000 | Lieber et al. |
| 6,048,616 | A | 4/2000 | Gallagher et al. |
| 6,136,156 | A | 10/2000 | El-Shall et al. |
| 6,207,229 | B1 | 3/2001 | Bawendi et al. |
| 6,225,198 | B1 | 5/2001 | Alivisatos et al. |
| 6,239,355 | B1 | 5/2001 | Salafsky |
| 6,245,988 | B1 | 6/2001 | Gratzel et al. |
| 6,251,303 | B1 | 6/2001 | Bawendi et al. |
| 6,306,736 | B1 | 10/2001 | Alivisatos et al. |
| 6,319,426 | B1 | 11/2001 | Bawendi et al. |
| 6,320,200 | B1 * | 11/2001 | Reed et al. .................... 257/40 |
| 6,322,901 | B1 | 11/2001 | Bawendi et al. |
| 6,399,224 | B1 | 6/2002 | Li |
| 6,413,489 | B1 | 7/2002 | Ying et al. |
| 6,512,172 | B1 | 1/2003 | Salafsky et al. |
| 6,649,129 | B1 | 11/2003 | Neal |
| 6,649,138 | B2 | 11/2003 | Adams et al. |
| 6,805,922 | B2 * | 10/2004 | Heeney et al. ............... 428/1.1 |
| 2002/0110645 | A1 | 8/2002 | Shelnut et al. |
| 2003/0226498 | A1 | 12/2003 | Alivisatos et al. |
| 2004/0026684 | A1 | 2/2004 | Empedocles |
| 2004/0118448 | A1 | 6/2004 | Scher et al. |

OTHER PUBLICATIONS

Bjork et al., "One-dimensional Steeplechase for Electron Realized" (2002) *Nano Letters* 2:86-90.

Cao et al., "Growth and properties of semiconductor core/shell nanocrystals with InAs cores" (2000) *J. Am. Chem. Soc.* 122:9692-9702.

Cui et al., "Doping and electrical transport in silicon wires" (2000) *J. Phys. Chem. B.* 104:5213-5216.

Cui et al., "Diameter-controlled synthesis of single-crystal silicon nanowires" (2001) Appl. Phys. Letts. 78(15):2214-2216.

Dabbousi et al., "(CdSe)ZnS core-shell quantum dots: Synthesis and characterization of a size series of highly luminescent nanocrystallites" (1997) J. Phys. Chem. B. 101:9463-9475.

Duan et al., "General synthesis of compound semiconductor nanowires" (2000) Adv. Mater. 12:298-302.

Greenham et al., "Charge separation and transport in conjugated-polymer/semiconductor-nanocrystal composites studied by photoluminescence quenching and photoconductivity," (1996) Phys. Rev. B—Condens Matter 54(24):17628-17637.

Greenham et al., "Charge separation and transport in conjugated-polymer/cadmium selenide nanocrystal composites studied by photoluminescence quenching and photoconductivity," (1997) Synth. Mater. 84:545-546.

Groenendaal et al., "Poly(3,4-ethylenedioxythiophene) and its derivatives: Past, present and future" (2000) Adv. Mater. 12:481-494.

Gudiksen et al., "Diameter-selective synthesis of semiconductor nanowires" (2000) J. Am. Chem. Soc. 122:8801-8802.

Gudiksen et al., "Synthetic control of the diameter and length of single crystal semiconductor nanowires" (2001) J. Phys. Chem. B. 105:4062-4064.

Gudiksen et al., "Growth of nanowire superlattice structures of nanoscale photonics and electronics" (2002) Nature 415:617-620.

Huynh et al., "CdSe Nanocrystals Rod/Poly (3-hexylthiophene) Composite Photovoltaic Devices" (1999) Adv. Mater. 11(11):923-927.

Huynh et al., "Hybrid Nanorod-Polymer Solar Cells" (2002) Science 295:2425-2427.

Jun et al., "Controlled synthesis of multi-armed CdS nanorod architectures using monosurfactant system" (2001) J. Am. Chem. Soc. 123:5150-5151.

Kraft et al., "Electroluminescent conjugated polymers—seeing polymers in a new light" (1998) Angew Chem. Int. Ed. 37:402-428.

Liu et al., "Sol-Gel Synthesis of Free-Standing Ferroelectric Lead Zirconate Titanate Nanoparticles" (2001) J. Am. Chem. Soc. 123:43444345.

Manna et al., "Synthesis of soluble and processable rod-, arrow-, and tetrapod-shaped CdSe nanocrystals" J. Am. Chem. Soc. (2000) 122:12700-12706.

Manna et al., "Epitaxial growth and photochemical annealing of graded Cds/ZnS shells on colloidal CdSe nanorods" (2002) J. Am. Chem. Soc. 124:7136-7145.

Milliron et al., "Electroactive surfactant designed to mediate electron transfer between CdSe nanocrystals and organic semiconductors" (2003) Adv. Mater 15(1):58-61.

Morales et al., "A lawer ablation method for the synthesis of crystalling semiconductor nanowires" (1998) Science 279:208-211.

Peng et al., "Epitaxial growth of highly luminescent CdSe/CdS core/shell nanocrystals with photostability and electronic accessibility" (1997) J. Am. Chem. Soc. 119:7019-7029.

Peng et al., "Shape control of CdSe nanocrystals" (2000) Nature 404:59-61.

Puntes et al., "Colloidal nanocrystal shape and sixe control: The case of cobalt" (2001) Science 291:2115-2117.

Urban et al., "Synthesis of single-crystalline perovskite nanowires composed of brium titanate and strontium titanate" (2002) J. Am. Chem. Soc. 124:1186.

Welsh et al., "Regiosymmetric dibutyl-substituted poly(3,4-propylenedioxythiphene)s as highly electron-rich electroactive and luminescent polymers" (2002) Macromolecules 35:6517-6525.

Wu et al., "Block-by-block growth of single-crystalline Si/SiGe superlattice nanowires" (2002) Nano letters 2:83-86.

Yun et al., "Ferroelectric properties of individual barium titanate nanowires investigated by scanned probe microscopy" (2002) Nano letters 2:447-450.

Yamamoto, T. et al. "Preparation of Pi-Conjugated Polymers Composed of Hydroquinone, p-Benzoquinone, and p-Diacetoxyphenylene Units. Optical and Redox Properties of the Polymers" Macromolecules (1999) 32:8886-8896.

* cited by examiner

T1--B3--H1

T2--B3--H1

T3--B3--H1

T1--B3--H2

T2--B3--H2

T3--B3--H2

T1--E3--H1

T2--E3--H1

T3--E3--H1

T1--E3--H2

T2--E3--H2

T3--E3--H2

“ORGANIC SPECIES THAT FACILITATE CHARGE TRANSFER TO OR FROM NANOSTRUCTURES

CROSS-REFERENCE TO RELATED APPLICATIONS

This application is a divisional of U.S. Ser. No. 10/656,910, filed Sep. 4, 2003, which is related to U.S. provisional applications U.S. Ser. No. 60/408,722, filed Sep. 5, 2002; and U.S. Ser. No. 60/452,232, filed Mar. 4, 2003. The present application claims priority to and benefit of each of these prior applications, which are hereby incorporated herein by reference in their entirety for all purposes.

FIELD OF THE INVENTION

The present invention is in the field of nanotechnology. More particularly, the present invention is directed to conductive ligands and matrices for use with nanostructures, as well as related methods for producing and using the conductive compositions, and related devices incorporating the conductive compositions.

BACKGROUND OF THE INVENTION

Polymer-based light-emitting and photovoltaic devices, including those incorporating nanocrystal-containing polymers are known in the art. The performance of polymer-based photovoltaic devices has been improved, e.g., by embedding semiconductor nanocrystals into the polymer matrix. For example, nanocomposite-based photovoltaic devices are described in WO 04/022637 and WO 04/023527. However, the performance of these and other devices that employ nanocrystals can be further improved.

Semiconducting nanocrystals can be designed with specific optical properties and/or electronic structures, in part by controlling the size and shape of the nanocrystals used as part of the light harvesting element in the photovoltaic devices. In addition, the polymeric matrix encompassing the nanocrystal can be selected to also absorb light. However, charge transport within the photovoltaic device is generally limited by matrix constraints, rather than by the absorption properties of the nanocrystals. As a result, charge transport through the matrix and/or among the nanocrystals is an important element of optimal photovoltaic operation.

Nanocrystal syntheses typically produce particles having surfaces coated with a surfactant layer, e.g., a layer of molecules having long aliphatic chains, such as alkyl phosphonic acids, alkyl amines, alkyl carboxylic acids, alkyl phosphines or alkyl phosphine oxides. These ligands form a substantially non-conductive layer on the nanocrystal surface. In applications in which it is desirable to efficiently remove or add charges to nanocrystalline structures, the residual aliphatic ligand layer limits the charge transfer to the surface. Synthesis of water soluble semiconductor nanocrystals capable of light emission are described, for example, in U.S. Pat. No. 6,251,303 to Bawendi et al. entitled "Water-soluble fluorescent nanocrystals" (Jun. 6, 2001) and U.S. Pat. No. 6,319,426 to Bawendi et al. titled "Water-soluble fluorescent semiconductor" (Nov. 20, 2001).

While conductive polymers are known in the art (see, for example, H. S. Nalwa (ed.), *Handbook of Organic Conductive Molecules and Polymers*, John Wiley & Sons 1997; U.S. Pat. No. 6,399,224 to Li, "Conjugated Polymers with Tunable Charge Injection Ability"; and U.S. Pat. No. 5,504,323 to Heeger et al., "Dual function conducting polymer diodes"), these polymers do not have any functional group(s) that can bind strongly to a nanocrystal surface. As such, these polymers do not make optimal contact with the nanocrystal.

The performance of nanocrystal-based light-emitting and photovoltaic devices would be improved if the removal or addition of charges via the nanocrystals was more energetically efficient. Accordingly, there exists a need in the art for improved ligands for use with nanocrystal structures. The present invention meets these and other needs by providing novel compositions for use with nanocrystals, as well as methods for making and using the novel compositions. A complete understanding of the invention will be obtained upon review of the following.

SUMMARY OF THE INVENTION

The present invention provides compositions (small molecules, oligomers and polymers) that can be used to modify charge transport across a surface or a nanostructure (e.g., nanocrystal) surface, or within a nanostructure (e.g., nanocrystal)-containing matrix, as well as methods for making and using the novel compositions. The compositions contain a conjugated organic species and at least one binding group capable of interacting with a nanostructure (e.g., nanocrystal) surface; during use, the compositions are coupled via the binding group to the nanostructure (e.g., nanocrystal) surface, such that the compositions are substantially conductive to electrons and/or holes being transported by/through the nanostructure (e.g., nanocrystal) (e.g., during the process of extracting or injecting the electrons or holes). The compositions of the present invention can optionally be derivatized with additional chemical groups, e.g., to enhance the electronic conjugation of the core organic species, to couple adjacent nanostructures (e.g., nanocrystals), or to facilitate dispersion, mixing and/or blending of nanostructures (e.g., nanocrystals) in various matrices.

In one aspect, the present invention provides conductive compositions for modification of charge transport across a nanostructure (e.g., nanocrystal)-containing matrix. The conductive composition typically include a) a conjugated organic moiety as the "body structure," or core of the conductive molecule; b) a nanostructure (e.g., nanocrystal)-binding "head group" coupled to the body structure at a first position on the conjugated organic moiety; and c) a "tail group" coupled to the body structure at a second position on the conjugated organic moiety. After formation of an exciton in the nanostructure (e.g., nanocrystal)-containing matrix, the conductive composition facilitates the injection and/or extraction of charge (electron and/or hole) with respect to the attached nanostructure, thereby modifying charge transport across a nanostructure-containing matrix.

The modular nature of the composition (and the corresponding methods for synthesizing the composition) lends itself toward modification or adjustment of the various elements of the composition (head, body, tail) based upon the desired use. As such, various constituents can be used for the different composition elements. For example, the body structure typically comprises a conjugated alkyl moiety or a conjugated aryl moiety (e.g., a phenylene, thiophene, ethene, ethyne, aniline, fluorene, pyridine, perylene, phenanthralene, anthracene, an alkynyl, or a polynuclear aromatic moiety). Chemical structures for use as the functionalized head group include, but are not limited to, one or more phosphonic acid, carboxylic acid, amine, phosphine, sulfonate, sulfinate, or thiol moieties. Tail group structures can be either conducting or nonconducting chemical moieties; preferred tail group substituents include, but are not limited to, 1-propyne, 1-butyne, 1-pentyne, 1-hexyne, 1-heptyne, 1-octyne, 1-nonyne, 1-decyne, or an alkyne comprising between 3 and 22 carbons. Optionally, either or both the head group and the tail group further include one or more thiophene moieties positioned between the body structure and the head or tail substituent.

In some embodiments, the tail group also includes a nanostructure (e.g., nanocrystal)-binding moiety (e.g., a phosphonic acid, carboxylic acid, amine, phosphine, or thiol moiety). Furthermore, the nanostructure-binding head group and/or nanostructure-binding tail group can provide either a single chemical moiety for attachment to the nanostructure (i.e., monodentate) or multiple binding moieties (i.e., multidentate). Optionally, these moieties are chosen or selected for their ability to bind to selected types of nanostructures (for example, the head group(s) selectively bind p-type nanocrystals while the tail group(s) selectively bind n-type nanocrystals).

The body structure optionally includes one or more additional substituents, or "sidechains," coupled to the conjugated organic species. In some embodiments, the sidechains are O-linked or N-linked sidechains coupled to the conjugated organic moiety. Addition of the sidechain (or other substituent) to the body structure preferably does not destroy the conjugation of the core organic species; rather, in some embodiments, the sidechain moiety or moieties extend the conjugation. As such, substituents for use as sidechain elements can include, but are nor limited to, an electron donating group, an electron withdrawing group, a conducting chemical structure, a nonconducting chemical structure, or various reactive functional groups or polymerizable elements (such as an acrylate moiety, a methacrylate moiety, or a vinyl moiety). In some embodiments, the sidechain is matched functionally and/or electronically to the nanostructure (e.g., nanocrystal)-containing matrix; in other embodiment, the sidechain element simply alters the solubility of the composition. Preferably, the conjugated compositions of the present invention have two sidechain substituents coupled to the body structure; however, the chemical compositions of the side chains need not be identical. Optionally, the sidechains can be employed to link and/or align adjacent nanostructures.

Exemplary sidechain substituents for use in the compositions of the present invention include, but are not limited to, an O-linked hexane moiety, an O-linked 2-ethylhexyl moiety, an O-linked octyl moiety, an O-linked decyl moiety, an N-linked hexane moiety, an N-linked 2-ethylhexyl moiety, an N-linked octyl moiety, and an N-linked decyl moiety. However, any N-linked or O-linked alkyl moiety having between 1 and 22 (or more) carbons are contemplated for use in the present invention.

In some embodiments of the present invention, the body structure employed in the conductive composition is an oligomeric or polymeric structure, rather than a monomeric chemical structure. Exemplary multimeric body structure components include, but are not limited to, poly(phenylene), poly(thiophene), poly(ethene), poly(ethyne), poly(aniline), poly(fluorene), poly(pyridine), poly(polynuclear) moieties, and combinations thereof. Optionally, the multimeric body structure is composed of two or more monomeric body structure elements linked by a linker region, such as a dithiophene moiety. Preferably the linker element allows or enhances electronic conjugation between the body structure elements. As with the monomeric embodiments, the multimeric body structure can optionally include one or more sidechains coupled to one or more elements of the oligomeric or polymeric structure.

The present invention also provides polymeric conductive compositions for use with nanostructure (e.g., nanocrystal) structures (e.g., in the case of nanocrystals, either as a nanocrystal coating or as a polymer matrix). The polymeric conductive compositions have the structure $[H_x\text{-}B_y\text{-}T_z]_n$, wherein H comprises at least one functionalized head group capable of binding to a nanostructure surface or at least one head group bound to a nanostructure surface; wherein B comprises a body structure comprising one or more conjugated organic moieties, wherein a first conjugated organic moiety is coupled to a proximal functionalized head group or bound head group; wherein T comprises at least one tail group coupled to the body structure; and wherein x, y, z and n independently comprise integers equal to or greater than 1. The sum of the integers x, y, z and n is equal to or greater than 5, such that at least one element (head, body or tail) is present in more than one "copy" in the polymeric conductive composition. The polymeric conductive composition is synthesized by polymerization of monomeric precursors through coupling of various polymerizable elements on one or more of the substituents.

In these polymeric conductive compositions, the head group optionally is one or more phosphonic acid, carboxylic acid, amine, phosphine, phosphine oxide or thiol moieties; the body structure is optionally a phenylene, thiophene, ethene, ethyne, aniline, fluorene, pyridine, perylene, phenanthralene, anthracene, an alkenyl moiety, a polynuclear aromatic moiety, or polymer thereof; and the tail group is optionally a 1-propyne, 1-butyne, 1-pentyne, 1-hexyne, 1-heptyne, 1-octyne, 1-nonyne, 1-decyne, or an alkyne comprising between 3 and 22 carbons. In further embodiments, the body structure further comprises one or more O-linked or N-linked substituents (e.g., electron donating or electron withdrawing groups, conducting chemical structures, or nonconducting chemical structures) coupled to one or more polymer subunits (e.g., member conjugated organic moieties). These O-linked of N-linked substituents can be used, e.g., to alter the electronic signature of the composition, or alter the solubility of the polymeric conductive composition.

As an additional aspect, the present invention provides nanostructure (e.g., nanocrystal)-containing matrix compositions. In one embodiment, the nanostructure-matrix composition includes a nanostructure coupled to a conductive composition (e.g., ligand) of the present invention, and a matrix positioned proximal to the ligand-conjugated exterior surface of the nanostructure. Optionally, the matrix is also covalently coupled to the nanostructure-bound conductive composition. In a preferred embodiment, the conductive composition is functionally or electronically matched to one or more substituents of the matrix.

In another embodiment, the nanostructure (e.g., nanocrystal)-containing matrix composition includes a nanostructure and a matrix composed of the polymeric conductive composition of the present invention. In one embodiment, a portion of the nanostructure exterior surface is coupled to the polymeric matrix. In another embodiment, the nanostructure is derivatized or functionalized with a conductive composition of the present invention prior to being embedded in the polymeric conductive composition. Optionally, the polymeric conductive composition and the nanostructure-bound conductive composition are matched functionally and/or electronically. In addition, the matrix composition and the conductive composition can optionally be covalently coupled.

In a further embodiment of the present invention, the nanostructure-matrix composition includes a conductive composition of the present invention coupled at a first position to a first nanostructure (e.g., nanocrystal) and coupled at a second position to a second nanostructure, and a matrix positioned proximal to the exterior surfaces of the nanostructure. In one optional example, the first nanostructure is a p-type nanocrystal, and the second nanostructure is a n-type nanocrystal.

The present invention also provides methods of synthesizing an organic composition that facilitates charge transfer for use in a nanostructure-containing device. The organic compositions made using these methods are particularly suitable for use in a photovoltaic device. The methods include the steps of: a) providing a conjugated organic precursor, wherein the conjugated organic precursor comprises at least three positions available for attachment of substituent modules (e.g., head, tail and sidechain); b) providing a first substituent module, wherein the first substituent module comprises a phosphonic acid derivative, a carboxylic acid derivative, an amine derivative, a phosphine derivative, a thiol derivative, a thiophene derivative, or a combination thereof; c) providing a second substituent module, wherein the second substituent module comprises an alkyne derivative comprising between three and 22 carbons; d) optionally providing a third substituent module, wherein the optional third substituent module comprises an alkyl derivative comprising between one and 22 carbons; and e) coupling the first substituent module at a first position, coupling the second substituent module at a second position, and optionally coupling the third substituent module at a third position, thereby synthesizing the organic composition.

At least one substituent of the first, second or third substituent modules is capable of binding to a nanostructure surface (or, optionally, the component is already bound to a nanostructure surface). Coupling of the various modules to the body structure does not destroy the electronic conjugation of the body structure. Rather, in a preferred embodiment, coupling of one or more of the substituent modules to the body structure extends the conjugation of the body structure.

In some embodiments of the present invention, the first substituent module is a thiophene derivative. The thiophene-containing head group substituent module can be prepared, for example, by a) providing an arylhalide core structure; b) lithiating the arylhalide core structure at a first halide position and reacting with chlorotrimethylsilane (TMSCl) to yield a TMS-aryl intermediate core structure; c) lithiating the intermediate core structure at a second halide position and reacting the product with trimethyltinchloride ($Me_3SnCl$) to yield a stannylated second intermediate; and d) combining the second intermediate with a halogenated thiophene to form a first substituent module comprising a TMS-aryl-thiophene derivative. Coupling the phosphite moiety to the TMS-aryl-thiophene derivative can be achieved, for example, by performing a palladium-catalyzed phosphite-aryl coupling. The first substituent module can be functionalized with the nanostructure-binding moiety (e.g., the phosphite group) either prior to coupling of the module to the body structure, or after the module has been attached.

Coupling of an alkyne moiety employed as the second substituent module can be performed, e.g., via a Sonogashira coupling. Optionally, the body structure has been functionalized with thiophene moieties at the first (e.g., head) and/or second (e.g., tail) positions prior to addition of the head and tail moieties.

Various reactions can be employed to couple the optional third substituent to the body structure. For example, alkylation reactions (e.g., a Williamson ether synthesis, a Friedel-Crafts alkylation reaction, or other aromatic electrophilic substitution reaction) can be used to couple the third substituent to the conjugated organic precursor at a third position having a hydroxyl or amine moiety, to form a sidechain-substituted intermediate composition.

In a preferred embodiment, the optional third substituent module (e.g., one or more sidechains) is coupled to the conjugated organic precursor prior to attachment of the first and/or second substituent modules. For example, providing and coupling the third substituent module can include: a) providing about 1.1 molar equivalents of a halogenated derivative of a sidechain substituent; b) combining the halogenated derivative with the conjugated organic precursor in the presence of potassium carbonate ($K_2CO_3$) and dimethyl formamide (DMF) to form a reaction mixture; and c) heating the reaction mixture to about 70° C., thereby coupling the third substituent to the conjugated organic moiety.

Optionally, additional sidechain substituents can be added to the conjugated organic precursor during the third substituent coupling step. For example, coupling the third substituent module optionally further includes coupling a fourth substituent to the body structure at a fourth position. The third and fourth substituents can be the same or different chemical species.

In some embodiments of the present invention, the methods of making the conductive composition also include the step of coupling or cojoining the head group (and any other nanostructure-binding moieties incorporated into the composition) to an external surface of a nanostructure, thereby providing a nanostructure-bound composition. Optionally, this step an be performed during the synthesis of the conductive composition (e.g., solid phase synthesis).

For embodiments utilizing substituent modules having polymerizable components incorporated therein, the methods of making the conductive composition can optionally further include the step of polymerizing the organic composition after coupling the composition to the nanostructure surface, thereby forming a polymerized conjugated organic composition.

As a further aspect, the present invention also provides methods of modifying an interaction between a nanostructure (such as a nanocrystal) and an external matrix. The methods include the steps of a) treating a nanostructure with a conductive composition the present invention; and b) forming a nanostructure-containing matrix comprising the treated nanostructure and a matrix composition, thereby modifying the interaction between the nanostructure and the external matrix. Optionally, the conductive composition applied to the nanostructure can be polymerized in situ, to form a polymerized conductive composition. In another embodiment, the matrix composition into which the coated nanostructure is placed constitutes the polymeric conductive composition of the present invention.

The present invention also provides devices, such as optoelectric devices, photovoltaic devices and light-emitting devices (LEDs) incorporating the conductive compositions of the present invention. The conductive compositions of the present invention can be coupled to either nanoscale and non-nanoscale (e.g., bulk crystalline) assemblies. The devices of the present invention typically include a first electrode surface and a second electrode surface, and having a semiconductor or nanostructure-containing matrix composition comprising the conductive compositions disposed between the two electrodes and electrically coupled to the first electrode surface and the second electrode surface. In one embodiment, the conductive compositions of the present invention are incorporated into photovoltaic devices, such as those described in WO 04/022637 and WO 04/023527. Alternatively, the compositions of the present invention can be used for charge injection into a fluorescent core/shell nanostructure containing device, e.g., to make an LED for use as a display or white light source.

DETAILED DESCRIPTION

Figure 1:
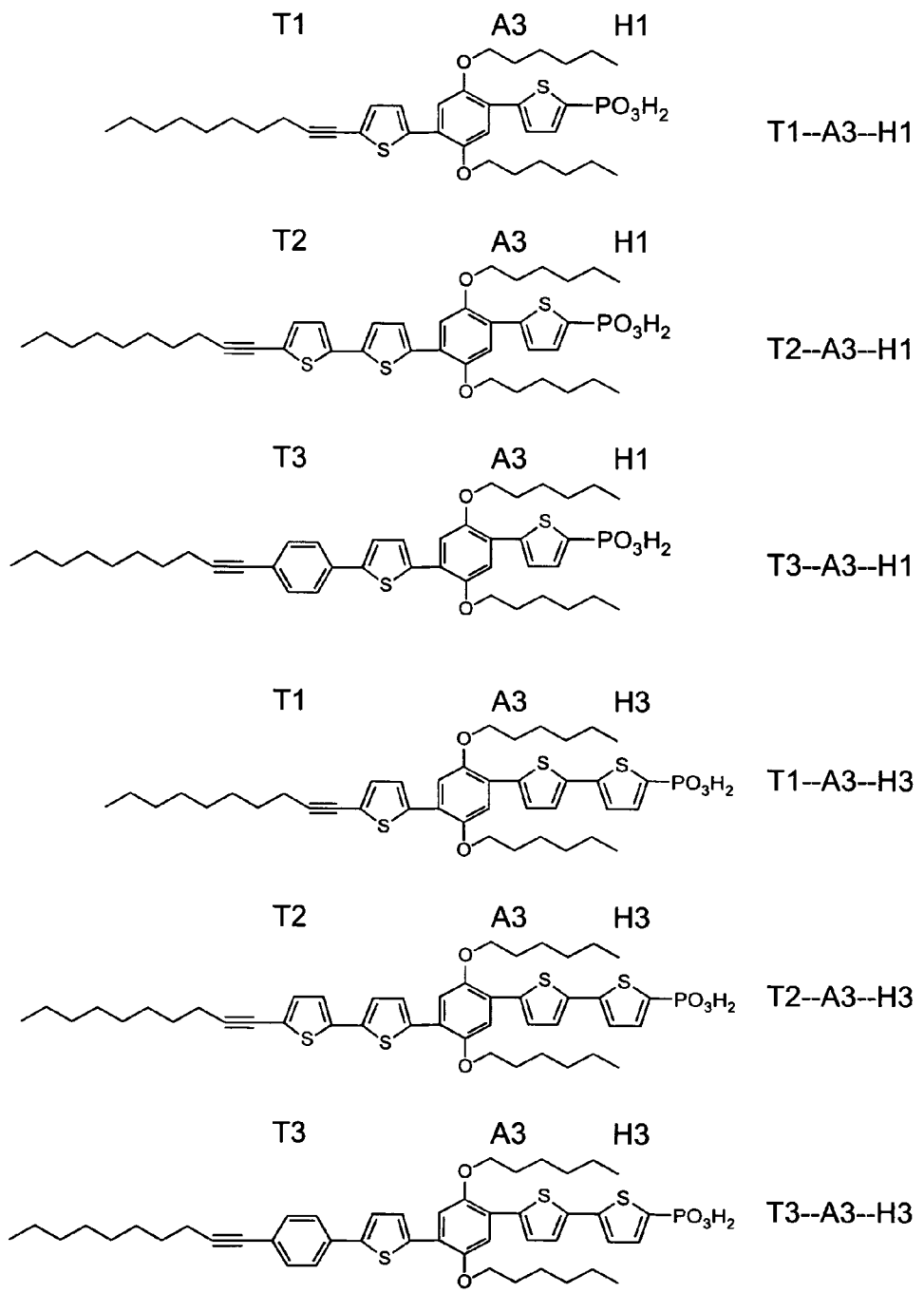
FIG. 1 provides exemplary conductive compositions of the present invention.
Figure 1:
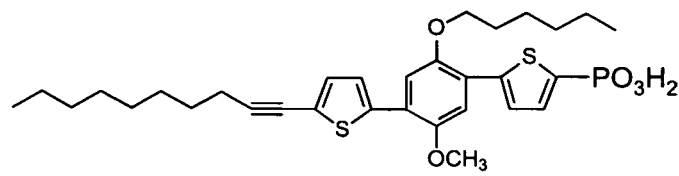
Figure 1:
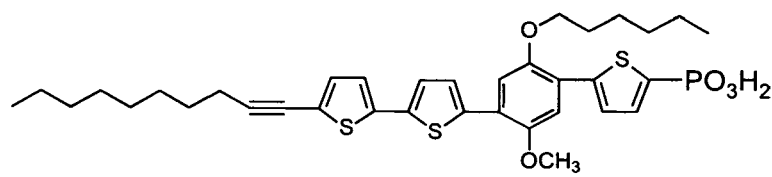
Figure 1:
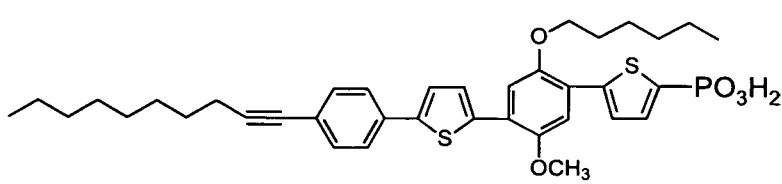
Figure 1:
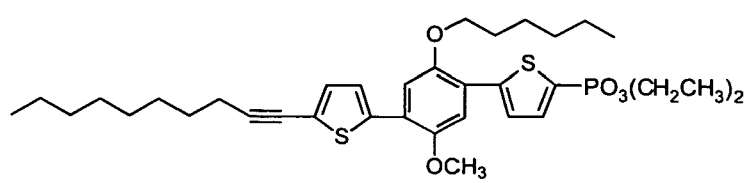
Figure 1:
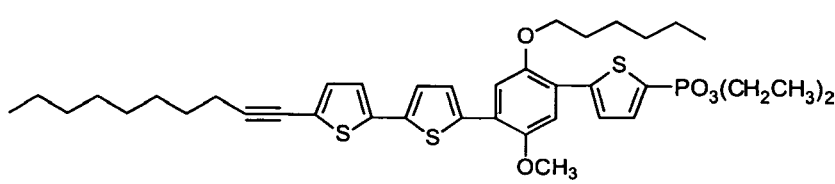
Figure 1:
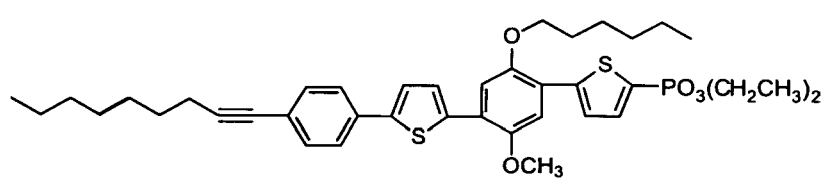
Figure 1:
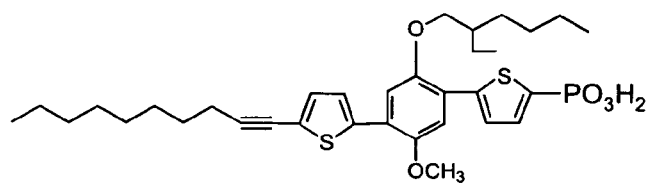
Figure 1:
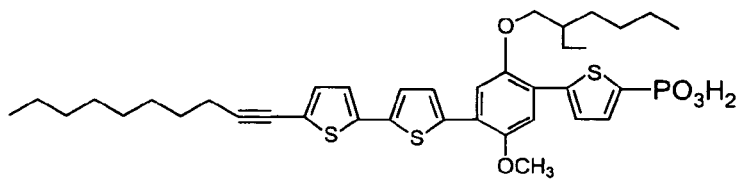
Figure 1:
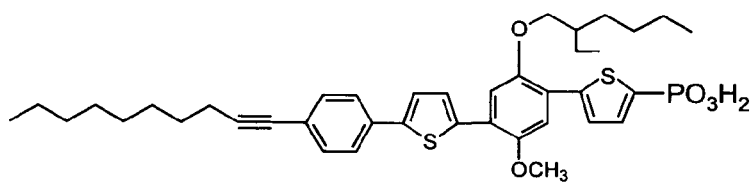
Figure 1:
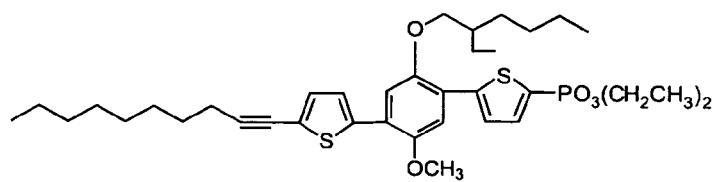
Figure 1:
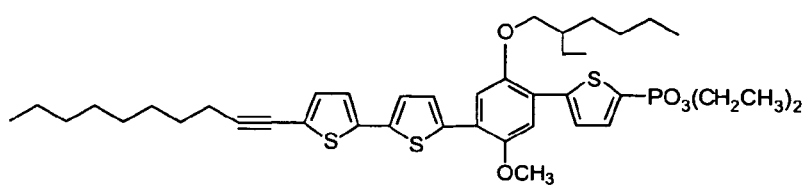
Figure 1:
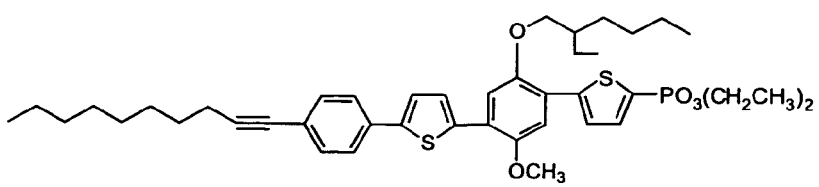

The present invention provides conductive small molecules, oligomers and polymers that can be used to modify charge transport across a nanostructure surface or within a nanostructure-containing matrix (e.g., a nanocomposite, e.g., comprising one or more nanocrystals, e.g., one or more inorganic nanocrystals).

Photovoltaic devices convert light (solar energy) into storable energy. When light is absorbed by nanocrystalline structures in a nanocomposite (e.g., a nanocrystal-containing composition), the absorption results in the formation of an electron-hole pair (also termed an "exciton"). The electron and hole can either recombine or remain separated, depending in part upon the configuration of the nanocomposite. Recombination of electrons and holes is desirable in some applications (e.g., light emission in LEDs) and undesirable in other applications.

In nanocomposites employed in photovoltaic devices, for example, the electron and hole preferably do not recombine, but rather travel to opposite electrodes. However, nanostructures (e.g., nanowires, branched nanowires, nanocrystals, amorphous nanostructures, nanoparticles, nanotetrapods, etc.) typically comprise one or more surface ligands (such as surfactant molecules introduced during synthesis) that are nonconductive in nature. See e.g. U.S. patent application 60/389,029 (filed Jun. 13, 2002) by Empedocles entitled "Nanotechnology enabled optoelectronics" and Milliron et al. (2003) "Electroactive surfactant designed to mediate electron transfer between CdSe nanocrystals and organic semiconductors" *Adv. Mater.* 15:58-61. The presence of these nonconductive nanostructure coatings reduces the efficiency of charge separation in the photovoltaic device. The compositions of the present invention are designed to moderate, enhance, or otherwise control the transport (e.g., separation) of the electron and hole generated in the nanocomposite. During use, the compositions are coupled to the nanocrystal surface, such that a conjugated organic species in the composition interacts electronically with the electrons and/or holes being transmitted through the nanocrystal. As noted above, this is in contrast with the currently-available organic nanocrystalline coatings, which are nonconductive in nature.

Definition

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a nanocrystal surface" or a "nanostructure surface" includes a combination of two or more surfaces; reference to "a substituent" includes mixtures of substituents, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

The term "conductive composition" as used herein refers to a monomeric (e.g. ligand), oligomeric or polymeric composition having the capacity for electron conduction, hole conduction, or the ability to otherwise undergo charge transfer.

The term "conjugated organic moiety" refers to an organic (i.e., carbon-containing) molecule having two or more double bonds alternating with single bonds, and as such includes both linear and cyclic structures.

The term "functionalized" as used herein refers to the presence of a reactive chemical moiety or functionality.

The term "alkyl" as used herein refers to a chemical substituent consisting of or containing the monovalent group $C_nH_{2n}$, where n is an integer greater than zero.

The term "aryl" as used herein refers to a chemical substituent consisting of or containing an aromatic group.

The terms "monodentate" and "multidentate" refers to a number of attachment sites (monodentate having one site and multidentate having more than one site).

The term "polymerizable element," as used herein, refers to a chemical substituent or moiety capable of undergoing a self-polymerization and/or co-polymerization reaction, and as such, includes, but is not limited to, vinyl derivatives, butadienes, trienes, tetraenes, diolefins, acetylenes, diacetylenes, styrene derivatives, as well as other reactive functional groups known to one of skill in the art.

The terms "oligomeric" and "polymeric" are used interchangeably herein to refer to multimeric structures having more than one component monomer or subunit.

The term "matrix" as used herein refers to a material, often a polymeric material, into which a second material (e.g., a nanocrystalline composition) is embedded or surrounded. The matrix can be a conductive composition, a semiconductive composition, or a non-conductive composition.

A "nanostructure" is a structure having at least one region or characteristic dimension with a dimension of less than about 500 nm, e.g., less than about 200 nm, less than about 100 nm, less than about 50 nm, or even less than about 20 nm. Typically, the region or characteristic dimension will be along the smallest axis of the structure. Examples of such structures include nanowires, nanorods, nanotubes, branched nanocrystals, nanotetrapods, tripods, bipods, nanocrystals, nanodots, quantum dots, nanoparticles, branched tetrapods (e.g., inorganic dendrimers), and the like. Nanostructures can be substantially homogeneous in material properties, or in certain embodiments can be heterogeneous (e.g. heterostructures). Nanostructures can be, e.g., substantially crystalline, substantially monocrystalline, polycrystalline, amorphous, or a combination thereof. In one aspect, each of the three dimensions of the nanostructure has a dimension of less than about 500 nm, e.g., less than about 200 nm, less than about 100 nm, less than about 50 nm, or even less than about 20 nm. Nanostructures can comprise one or more surface ligands (e.g., surfactants).

The terms "crystalline" or "substantially crystalline", when used with respect to nanostructures, refer to the fact that the nanostructures typically exhibit long-range ordering across one or more dimensions of the structure. It will be understood by one of skill in the art that the term "long range ordering" will depend on the absolute size of the specific nanostructures, as ordering for a single crystal cannot extend beyond the boundaries of the crystal. In this case, "long-range ordering" will mean substantial order across at least the majority of the dimension of the nanostructure. In some instances, a nanostructure can bear an oxide or other coating, or can be comprised of a core and at least one shell. In such instances it will be appreciated that the oxide, shell(s), or other coating need not exhibit such ordering (e.g. it can be amorphous, polycrystalline, or otherwise). In such instances, the phrase "crystalline," "substantially crystalline," "substantially monocrystalline," or "monocrystalline" refers to the central core of the nanostructure (excluding the coating layers or shells). The terms "crystalline" or "substantially crystalline" as used herein are intended to also encompass structures comprising various defects, stacking faults, atomic substitutions, and the like, as long as the structure exhibits substantial long range ordering (e.g., order over at least about 80% of the length of at least one axis of the nanostructure or its core). In addition, it will be appreciated that the interface between a core and the outside of a nanostructure or between a core and an adjacent shell or between a shell and a second adjacent shell may contain non-crystalline regions and may even be amorphous. This does not prevent the nanostructure from being crystalline or substantially crystalline as defined herein.

The term "monocrystalline" when used with respect to a nanostructure indicates that the nanostructure is substantially crystalline and comprises substantially a single crystal. When used with respect to a nanostructure heterostructure comprising a core and one or more shells, "monocrystalline" indicates that the core is substantially crystalline and comprises substantially a single crystal.

A "nanocrystal" is a nanostructure that is substantially monocrystalline. A nanocrystal thus has at least one region or characteristic dimension with a dimension of less than about 500 nm, e.g., less than about 200 nm, less than about 100 nm, less than about 50 nm, or even less than about 20 nm. Typically, the region or characteristic dimension will be along the smallest axis of the structure. Examples of such structures include nanowires, nanorods, nanotubes, branched nanowires, nanotetrapods, nanotripods, nanobipods, nanocrystals, nanodots, quantum dots, nanoparticles, nanoribbons, and the like. Nanostructures can be substantially homogeneous in material properties, or in certain embodiments can be heterogeneous (e.g. heterostructures). Optionally, a nanocrystal can comprise one or more surface ligands (e.g., surfactants). The nanocrystal is optionally substantially single crystal in structure (a "single crystal nanostructure" or a "monocrystalline nanostructure"). While nanostructures for use in the present invention can be fabricated from essentially any convenient material or material, preferably the nanostructure is prepared from an inorganic material, e.g., an inorganic conductive or semiconductive material. A conductive or semi-conductive nanostructure often displays 1-dimensional quantum confinement, e.g., an electron can often travel along only one dimension of the structure. Nanocrystals can be substantially homogeneous in material properties, or in certain embodiments can be heterogeneous (e.g. heterostructures). The term "nanocrystal" is intended to encompass substantially monocrystalline nanostructures comprising various defects, stacking faults, atomic substitutions, and the like, as well as substantially monocrystalline nanostructures without such defects, faults, or substitutions. In the case of nanocrystal heterostructures comprising a core and one or more shells, the core of the nanocrystal is typically substantially monocrystalline, but the shell(s) need not be. The nanocrystals can be fabricated from essentially any convenient material or materials.

A "nanowire" is a nanostructure that has one principle axis that is longer than the other two principle axes. Consequently, the nanowire has an aspect ratio greater than one; nanowires of this invention have an aspect ratio greater than about 1.5 or greater than about 2. Short nanowires, sometimes referred to as nanorods, typically have an aspect ratio between about 1.5 and about 10. Longer nanowires have an aspect ratio greater than about 10, greater than about 20, greater than about 50, or greater than about 100, or even greater than about 10,000. The diameter of a nanowire is typically less than about 500 nm, preferably less than about 200 nm, more preferably less than about 150 nm, and most preferably less than about 100 nm, about 50 nm, or about 25 nm, or even less than about 10 nm or about 5 nm. The nanowires employed in the present invention can be substantially homogeneous in material properties, or in certain embodiments can be heterogeneous (e.g. nanowire heterostructures). The nanowires can be fabricated from essentially any convenient material or materials. The nanowires can comprise "pure" materials, substantially pure materials, doped materials and the like, and can include insulators, conductors, and semiconductors. Nanowires are typically substantially crystalline and/or substantially monocrystalline. Nanowires can have a variable diameter or can have a substantially uniform diameter, that is, a diameter that shows a variance less than about 20% (e.g., less than about 10%, less than about 5%, or less than about 1%) over the region of greatest variability and over a linear dimension of at least 5 nm (e.g., at least 10 nm, at least 20 nm, or at least 50 nm). Typically the diameter is evaluated away from the ends of the nanowire (e.g. over the central 20%, 40%, 50%, or 80% of the nanowire). A nanowire can be straight or can be e.g. curved or bent, over the entire length of its long axis or a portion thereof. In certain embodiments, a nanowire or a portion thereof can exhibit two- or three-dimensional quantum confinement. Nanowires according to this invention can expressly exclude carbon nanotubes, and, in certain embodiments, exclude "whiskers" or "nanowhiskers", particularly whiskers having a diameter greater than 100 nm, or greater than about 200 nm. Nanorods, nanowires and other nanostructures are described in detail in WO 04/022637, the contents of which are incorporated herein in their entirety.

An "aspect ratio" is the length of a first axis of a nanostructure divided by the average of the lengths of the second and third axes of the nanostructure, where the second and third axes are the two axes whose lengths are most nearly equal each other. For example, the aspect ratio for a perfect rod would be the length of its long axis divided by the diameter of a cross-section perpendicular to (normal to) the long axis.

The "band gap difference" between HOMO and LUMO states refers the energy necessary make the transition across the "band gap" region separating the valence and conduction bands.

Conductive Composition

In one aspect, the present invention provides conductive compositions for modification of charge transport, e.g., across a nanostructure-containing matrix. The compositions are used in conjunction with a nanostructure composition, such as a nanocrystal-containing photovoltaic matrix. Alternatively, the conductive compositions of the present invention can be employed with non-nanoscale semiconductive components. The conductive compositions of the present invention typically include three basic components: a core element or "body structure," a "head group" coupled to the body structure at a first position and capable of associating with a nanostructure surface, and a "tail" group coupled to the body structure at a second position. In addition, the conductive composition can optionally include one or more "sidechain" elements coupled to the body structure at additional locations (i.e. third position, fourth position, etc).

Each of these components is described in greater detail below. The elements comprising the conductive compositions of the present invention work together to provide a conductive coating on the bound surface (e.g., a nanocrystal surface), or a polymeric matrix encompassing the semiconductor surface, thereby permitting and/or enhancing electron and/or hole transfer. For example, when light impinges upon a nanocrystal component of an optoelectric device (such as a photovoltaic device), the photon is absorbed by the nanocrystal creating an exciton within the nanocrystal. By conducting the electron away from the hole, one creates an electric potential that can be exploited. The conductive compositions (e.g., ligand-type coatings and/or polymeric matrices) of the present invention assist in the generation of the electric potential. The assistance can be, for example, via donation (injection) of an electron to the nanocrystal or other semiconductive material, or via conduction (extraction) of the hole away from the nanocrystal or semiconductor. In a preferred embodiment, the charge mobility (movement of the electrons) enhanced by the conductive compositions of the present invention is sufficiently fast so as to avoid recombination of the electron and hole. A further discussion of charge separation and conduction as it relates to the conductive compositions and related devices of the present invention (e.g., photovoltaic devices and LEDs) can be found in WO 04/023527.

Body Structure

A conjugated organic moiety is selected for the core of the conductive composition. This conjugated moiety typically is either a conjugated alkyl moiety or a conjugated aryl moiety. Exemplary body structures for use in the compositions of the present invention include, but are not limited to, phenylene, thiophene, ethene, ethyne, aniline, pyridine, phenanthralene, various alkenyl structures, and the like. In some embodiments, a polynuclear aromatic moiety (e.g., a polynuclear aromatic hydrocarbon, or PAH) is employed as the conjugated organic moiety. Exemplary PAH compounds include, but are not limited to, anthracene, benzo[a]anthracene, chrysene, fluorene, perylene, naphthalene, acenaphthene, acenaphthalene, phenanthrene, pyrene, benzo[a]pyrene, and the like.

In one embodiment, the function of the conjugated organic moiety is to provide hole transport from the crystal to the polymer matrix (and optionally, to an electrode or electrode surface of, e.g., a photovoltaic device). Movement of the hole along this conjugated "backbone" of the conductive composition (e.g., charge transport) is enhanced by selecting or matching the electronic characteristics of the body structure, such that hole transport from the nanocrystal to the polymer matrix is favored over electron transport (i.e., the body structure element of the conductive composition has a higher HOMO energy level than the nanocrystal and a lower HOMO level than the surrounding polymer). Alternatively, the conductive composition of the present invention can be modularly designed for enhanced electron transport.

In some embodiments of the present invention, the body structure is an oligomeric or polymeric structure, such as poly(phenylene), poly(thiophene), poly(ethene), poly(ethyne), poly(aniline), poly(fluorene), poly(pyridine), poly(PAH), and the like. The extent of polymerization can range from just a few repeating elements (e.g., 2, 3, 4, 5, 6, etc) or longer polymers (e.g., having tens of repeating units). Furthermore, additional or alternative oligomeric or polymeric conjugated structures known to one of skill in the art can also be employed as the body structure of the present composition.

Head Group

The conductive compositions of the present invention further include a "head group" coupled to the body structure at a first position on the conjugated organic moiety. In the unbound configuration, the head group is a functionalized element capable of binding to a nanostructure surface. Optionally, the head group is a bound head group (e.g., for embodiments in which the composition is associated with the nanostructure). Both the bound and functionalized chemical structures are considered "head groups" in the present invention.

Exemplary chemical moieties for use as functionalized head groups in the present invention include, but are not limited to, phosphonic acid, phosphinic acid, carboxylic acid, amine, amine oxide, phosphine, phosphine oxide, phosphonate, phosphonite, hydroxyl, and thiol moieties.

Alternatively, nitrogen-containing aromatic compounds or heterocycles (e.g., imidazoles, benzoimidazoles, pyridines, pyrimidines, purines, or quinolines) can also be used as nanostructure-binding head group moieties in the compositions of the present invention. Exemplary compounds include, but are not limited to, derivatives of 2-methylpyridine, 3-ethylpyridine, 4-chloropyridine, collidine, dimethylquinoline, and other compounds commonly used as nanostructure growth terminators.

In some embodiments, the functionalized (or bound) head group is a monodentate structure (e.g., a single moiety capable of binding the nanostructure). In an alternate embodiment, the head group is a multidentate structure capable of a plurality of interactions with the nanostructure surface.

Optionally, the head group element includes one or more polymerizable elements. The polymerizable element can be employed, in some embodiments, to prepare conductive compositions having a plurality of head group modules attached (e.g., linearly) to a single body structure. One such composition would have the formula $(H_x)$-B-T, in which x copies of the head moiety (H) are attached to a body structure (B) and tail group (T), e.g., during synthesis of the conjugated composition. Alternatively, the polymerizable elements on the head group are used to polymerize proximal elements of the conductive composition. The polymerization can occur between two head groups, or between a head group and another element of the conductive composition (e.g., a tail group or optional sidechain). An exemplary composition of this nature is described by the formula $(H-B-T)_n$, where n represents the number (or average number) of member compositions in the polymer. While the proximal elements are preferably polymerized after attachment to the nanostructure surface, in some polymeric embodiments, the elements are polymerized prior to exposure to the nanostructure.

Tail Group

The conductive compositions of the present invention also include a tail group coupled to the body structure at a second position (tail position) on the conjugated organic moiety. Either conducting or a non-conducting chemical structures can be employed as tail groups in the present invention. Typically, the tail group is an alkyne structure composed of n carbons (where n is equal to 3-22); however, even larger alkyne structures (having greater than 22 carbons) are also contemplated for use in the compositions of the present invention. Exemplary alkynes for use in the present invention include, but are not limited to, 1-propyne, 1-butyne, 1-pentyne, 1-hexyne, 1-heptyne, 1-octyne, 1-nonyne, and 1-decyne. Optionally, any alkyne comprising between 3 and 22 carbons (or longer) can be employed as a tail group in the present invention. Alternatively, other moieties having "rigid" elements, such methylene, aryl, acetylene and alkene groups, can be used as tail groups in the present invention. The more rigid constituents can be used to produce more conductive compositions (and, in the embodiment in which the conductive compositions include polymerizable elements, a more thermodynamically predictable product).

The alkyne structure can be linear or branched, depending in part upon the particular system in which the composition will be employed. For example, in some embodiments, the increased steric hindrances incurred by branched alkynyl chain employed as tail groups can affect the conjugation of the conductive composition (e.g., by altering the positioning of an aryl component of the body structure). Changes in the molecule-molecule and polymer-molecule order, stacking and packing can also have an effect on the electronic properties and charge transport capabilities. In a preferred embodiment, linear (e.g., non-branched) alkyl chains are preferred for use as tail group moieties.

In some embodiments, the tail group further includes a thiophene moiety; when present, the thiophene is preferably positioned between the alkyne moiety and the body structure (e.g., the thiophene couples the tail group to the conjugated organic species at the second position of the body structure).

Optionally, the tail group further includes a chemical functionality capable of binding to the nanostructure surface. As described for the head group element, the tail group can be either a monodentate or a multidentate structure. When present, the nanostructure-binding functionality incorporated into the tail group is optionally used, for example, for coupling to a second nanostructure surface (e.g., forming a bridging composition between proximal nanocrystals).

For example, in a further embodiment, the conductive composition of the present invention can include a di-alkyne or di-alkene tail group substituent having the formula CC—$(CH2)_n$—CC, in which CC represents either double or triple bonded carbon atoms (flanking an alkyl chain, in this embodiment). Optionally, a nanostructure binding moiety (e.g., phosphanate) is incorporated within the tail element, e.g., at a site distal to the site for attachment to the body structure (as represented by the formula $(OH)_2P(O)$—CC—$(CH2)_n$—CC—). The presence of multiple alkyne or alkene moieties within the tail group module can be used to alter the geometry of the tail and can affect the binding of the head group. The nanostructure binding moiety incorporated into the tail group can be the same or different moiety as present in the head group. Optionally, the nanostructure binding moiety incorporated into the tail group can be used to bind to the same nanostructure as the head group, or it can be coupled to an adjacent crystal (i.e., linking the crystals). In a further embodiment, different nanostructure binding moieties favoring attachment to different nanostructure structures are employed in the multi-dentate conductive compositions of the present invention (forming, e.g., an asymmetric bidentate conductive composition). Such compositions can be employed, e.g., to align nanostructures within a two crystal system.

In another embodiment of the present invention, the tail group includes one or more polymerizable elements. As described previously, the polymerizable element can be employed, in some embodiments, to prepare conductive compositions having a plurality of tail group modules attached (e.g., linearly) to a single body structure. One such composition would have the formula H-B-$(T_z)$, in which z copies of the tail moiety are attached to the body structure. Alternatively, the polymerizable elements on the tail group are used to polymerize proximal elements of the conductive composition, similar to that described for the optional polymerizable elements on the head group (e.g., between two tail groups, or between a tail group and another element of the conductive composition). While the proximal elements are preferably polymerized after attachment to the nanostructure surface, the polymerizable elements can be coupled prior to exposure of the composition to the nanostructure.

Optional Sidechains

The body structure optionally includes one or more sidechains coupled to the conjugated organic species. Optionally, the conductive composition includes two, three, or four side chains (although additional sidechains are conceivable given an appropriately-configured body structure).

Changes in sidechain composition can be used, e.g., to alter the solubility of the conductive composition, for electronic adjustment of the composition, and/or for polymerization purposes. For example, the sidechain can optionally include a carbonyl ester moiety; as a result of the electron-withdrawing property of the carbonyl, the conductive composition containing this sidechain will enhance (favor) electron transfer. Alternatively, incorporation of a simple alkyl chain as the sidechain substituent will favor hole transfer by virtue of the electron donating nature of the substituent.

Either conducting or a non-conducting chemical structures can be employed as sidechains in the present invention. Conducting chemical structures have the added advantage of extending the conjugation of the organic core structure.

In a preferred embodiment, the sidechains are O-linked or N-linked chemical structures (e.g., are coupled to an existing hydroxyl or amine group on the body structure). Exemplary sidechain moieties for use in the present invention include, but are not limited to, an O-linked or N-linked hexane moiety, an O-linked or N-linked 2-ethylhexyl moiety, an O-linked or N-linked octyl moiety, an O-linked or N-linked decyl moiety. Optionally, any O-linked or N-linked alkyl moiety comprising between 5 and 22 (or more) carbons can be used as a sidechain component (including alkane, alkene, alkyne, vinyl, and aryl structures).

As noted above, the chemical substituents employed as sidechain elements can optionally be either electron donating groups or electron withdrawing groups, depending upon the intended use. For example, in embodiments in which the modification of charge transport involves electron transport, electron withdrawing groups are preferred; in contrast, for transport of the "holes", electron donating groups function better.

In a preferred embodiment, a first sidechain is coupled to the body structure at a first sidechain position (i.e., a third position on the conjugated organic species), and a second sidechain is coupled to the body structure at a second sidechain position (i.e., a fourth position on the conjugated organic species). The sidechains can be identical chemical moieties, or they can differ in their chemical structure. Optionally, the side chain(s) can have the same chemical composition as the head group or the tail group.

In some embodiments of the present invention, the sidechain substituent is matched functionally and/or electronically to a matrix composition of the nanostructure-containing matrix. For example, the sidechain optionally can include functionalities which interact with matrix functionalities (e.g., affinity binding, ionic interactions, covalent interactions and/or bond formation, and the like). Alternatively, the sidechain elements can be used to affect the electronic signature of the surrounding matrix. For example, the distance between the conductive composition (e.g., ligand) and the polymer matrix, the aryl group matrix-matrix stacking distance and packing order, and/or the matrix-ligand stacking distance and packing can be altered or controlled by varying the sidechain element of the conductive composition, thereby affecting the interaction of the side chain with the surrounding matrix and modifying the electronic signature of the matrix-ligand-nanostructure system.

The length of the alkyl portion of the sidechain can be used to influence solubility; as such and can be any length or branching scheme. Both solubility and electronic properties can be adjusted simultaneously (or independently) via various combinations of the sidechain elements.

In another embodiment of the present invention, the side group includes one or more polymerizable elements. In some embodiments of the compositions of the present invention, the polymerizable elements on the sidechains interact with each other, thereby crosslinking individual members of the conductive composition to form a polymeric conductive composition. The polymerization can occur between sidechains on adjacent conductive compositions, or between a sidechain and another element of the conductive composition (e.g., a head group or tail group). While the proximal elements are preferably polymerized after attachment to the nanostructure surface, in some embodiments, the elements are polymerized prior to exposure to the nanostructure.

Alternatively, the polymerizable element can be employed to prepare extended sidechain components (e.g., as a means for coupling additional moieties to the conductive composition).

Exemplary chemical moieties which can be incorporated as sidechain elements include, but are not limited to, alkyl (e.g., alkane, alkene, or alkyne) chains ranging in length from one carbon to 22 carbons (or longer), carbonyls, acrylates, methacrylates, cinnamic esters, and the like. In some embodiments, the sidechain element includes a carbonyl ester having a diene moiety, such as butadiene (e.g., O—C(O)—(CH$_2$)$_n$-butadiene). The diene moiety, which can be positioned anywhere along the esterified alkyl chain (e.g., near the carbonyl, towards the middle of the alkyl chain, at the terminus distal to the O-linkage, etc.). can then optionally be polymerized, for example, with light via a 2+2 or 4+4 polymerization reaction. See, for example, Paleos (ed.) Polymerization in Organized Media (Gordon and Breach Science Publishers, Philadelphia, 1992.

Furthermore, the modular approach to the chemical synthesis of the conductive compositions of the present invention (e.g., convergent periphery modification) lends itself to a number of combinations of various head moieties, tail groups, and optional side chain elements.

Exemplary conductive compositions of the present invention are provided in Table 1 below, and in the figures and examples.

TABLE 1

Exemplary conductive compositions

5b 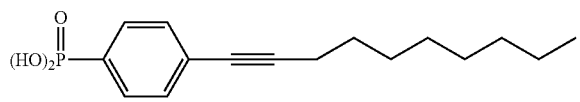

16 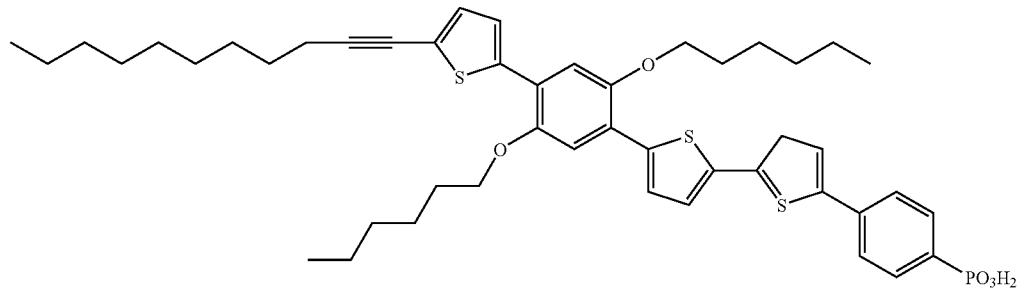

TABLE 1-continued
Exemplary conductive compositions
21b
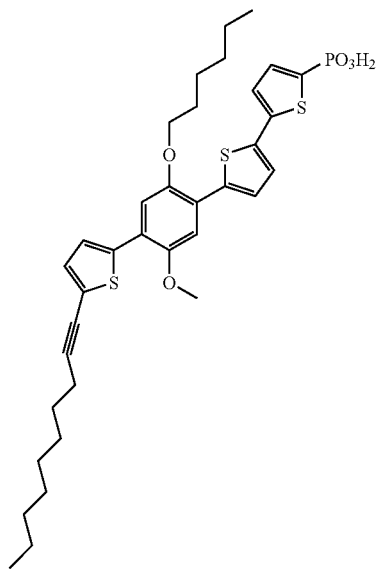
25
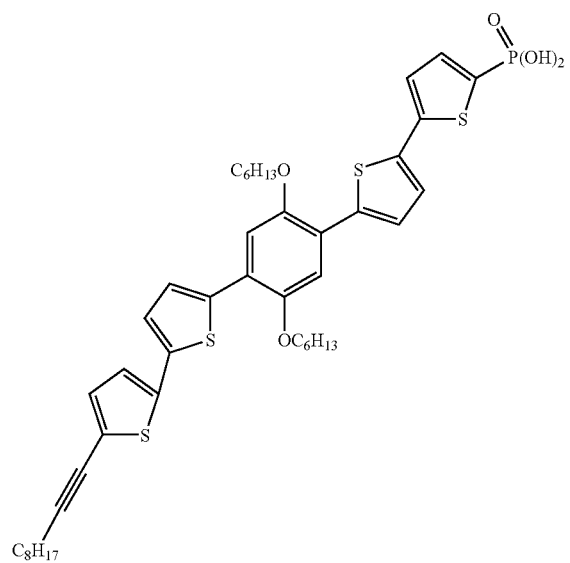
28
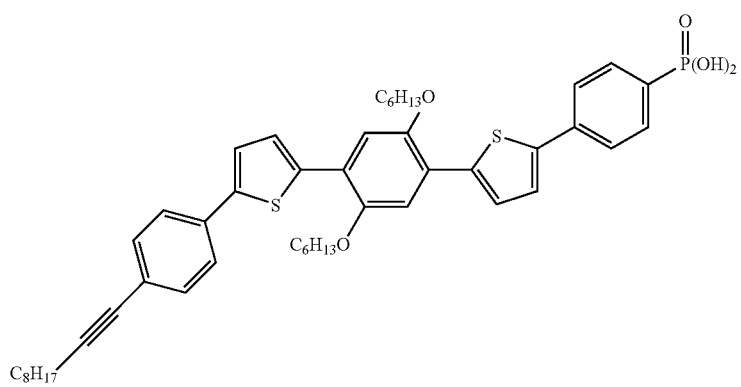

TABLE 1-continued
Exemplary conductive compositions
31 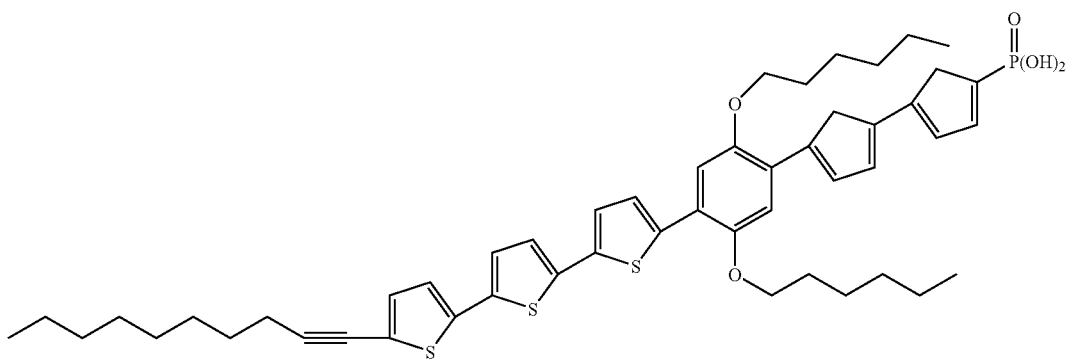
36 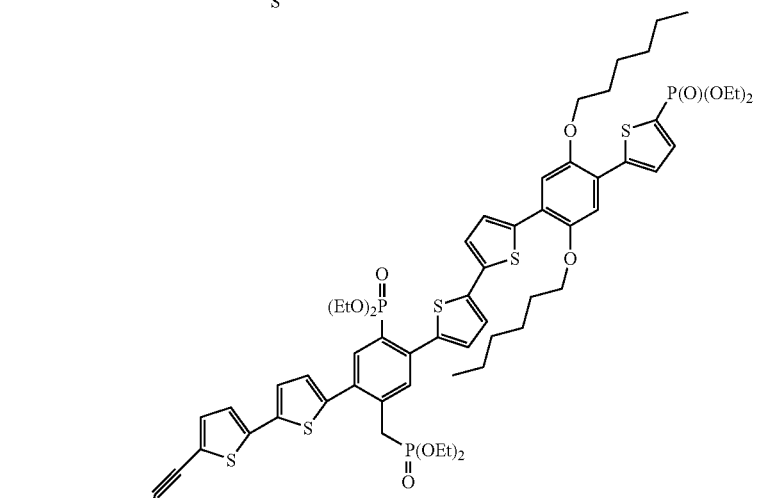
41a 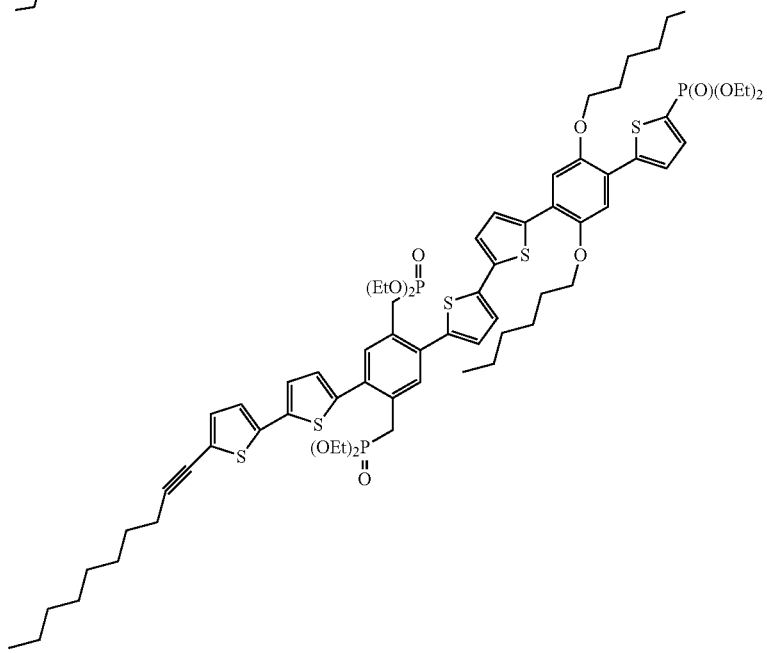

TABLE 1-continued

Exemplary conductive compositions

43

46

50

Polymer Embodiment

As noted above, one or more of the constituents of the conductive compositions can optionally include polymerizable elements. The present invention also provides oligomeric and polymer conductive compositions for use with nanostructures. The oligomeric and/or polymeric compositions can be used as either coatings on nanostructures, or as the matrix into which the nanostructure in embedded. Optionally, the nanostructure is coated with a first conductive composition of the present invention, and the embedded in an additional (e.g., second) polymeric conductive composition. In an additional embodiment, different types of nanostructures (e.g., p-type and n-type nanocrystals) are coupled or crosslinked within a matrix via the conductive compositions of the present invention.

One way to accomplish efficient charge transport is by designing an electronic "stairway" for both holes and electrons via bandgap adjustment, where the matrix polymer may have a highest occupied molecular orbital (HOMO) level slightly higher than the HOMO of a nanostructure-bound conductive composition ligand (which itself has a HOMO level higher than that of the nanostructure). Since the energetically favored pathway for hole transport is from lower to higher HOMO levels, this design will promote hole transport from the nanostructure to the ligand to the polymer to the electrode. Conversely, the matrix polymer can have a LUMO (lowest unoccupied molecular orbital) level slightly lower than the ligand LUMO, and the ligand LUMO may be lower than the crystal LUMO level. This will favor electron transport from the polymer via the ligand and nanostructure to the electrode. We have performed model calculations of the bandgap, HOMO and LUMO levels of the ligands and polymer, showing that this can be achieved by tuning both the ligand and the polymer to meet these requirements. One way to accomplish this is to use similar components for the polymer and the oligomer so the electronic signatures of each are similar but can be tuned slightly to afford the appropriate electronic stairway for hole and electron transport, respectively.

Polymerizable Elements

Any of the elements of the of the conductive compositions of present invention (head group, body structure, tail group, and/or sidechains) can include one or more of the polymerizable elements. Exemplary chemical substituents which can be incorporated into the composition, but are not limited to, vinyl derivatives, butadienes, trienes, tetraenes, diolefins, acetylenes, diacetylenes, styrene derivatives and the like. Exemplary sidechain substituents and/or derivatives (and mechanisms for coupling or crosslinking) are provided, for example, in Paleos, supra, and Kraft et al. (1998) "Electroluminescent Conjugated Polymers—Seeing Polymers in a New Light" *Angew Chem. Int. Ed.* 37:402-428.

For the crosslinking reaction, the polymerizable element can be situated at the end of the selected element, or it an be internal (e.g., amidst an alkyl chain substituent). Various polymerization schemes are contemplated in the present invention, including, but not limited to, polyaddition reactions (thermal, photo-induced or radiation-induced); polycondensations; oxidative couplings, and the like. A preferred polymerization scheme is vinyl polymerization of sidechain substituents in adjacent conductive compositions.

Polymeric Compositions

Figure 8:
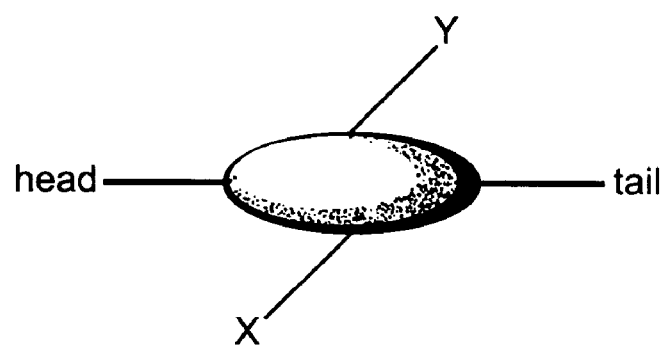
FIG. 8 provides a pictorial representation of a further embodiment of the present invention depicting both monomeric and polymeric conductive compositions.
Figure 8:
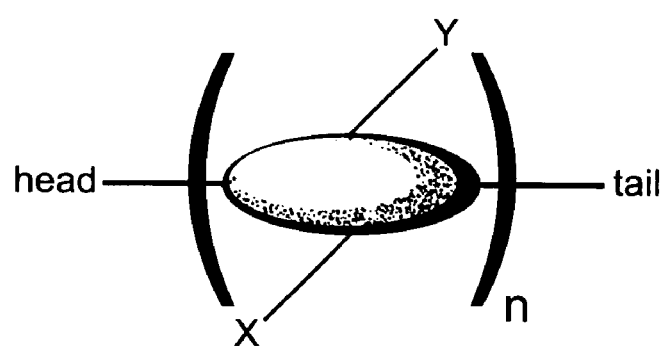
Figure 8:
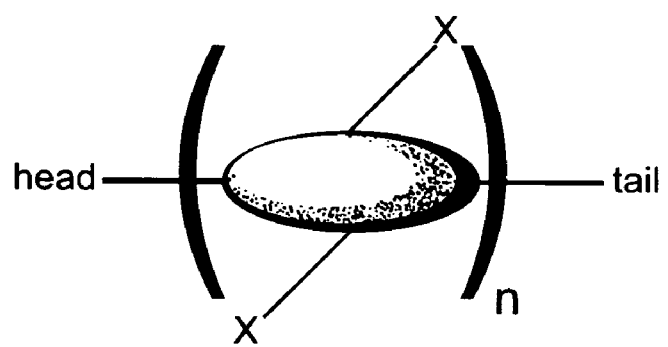
Figure 8:
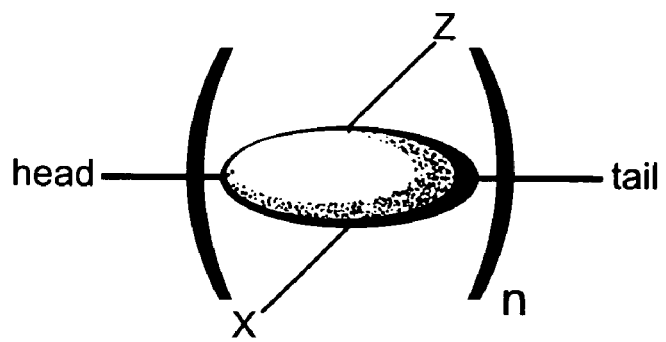

In a preferred embodiment, the polymeric conductive compositions of the present invention typically have the structure $[H_x\text{-}B_y\text{-}T_z]_n$, where H represents the head group, B represents the body structure, and T represents the tail group. The subscripts x, y and z represent the number of repeating elements (of head group, body structure, or tail group, respectively) present in a "monomeric" subunit of the polymer, while the value for n provides for the number of monomeric units present in the polymer; these values are integers. An embodiment in which x, y, z and n all equal 1 is equivalent to the monomeric conductive composition as previously described. Thus, for the polymeric composition of the invention, the sum of these integers (x+y+z+n) is an integer greater than 4 (i.e., 5 or greater). FIG. 8 depicts exemplary polymeric conductive compositions of the present invention in which multiple body structure components are depicted with similar or dissimilar sidechain elements attached. N is an integer, ranging in value from 1 (i.e., the monomeric form of the composition) to 10 or more. (e.g., to 15, 2, 25, 50, 100, etc.)

Sidechains can also be present, coupled to one or more of the body structures in the polymeric conductive composition; these optional sidechains are not depicted in the formula independent of body structure B, but are optionally present. In some polymeric embodiments of the present invention, the sidechain moiety is present on a majority of the body structures present (i.e., on at least 50% of the body structures); in further embodiments, the sidechain is present on at least 75%, 90%, 95%, 99% or essentially all of the member body structures. Optionally, these sidechain moieties can be the same chemical functionality; alternatively, the composition of the sidechain varies from body structure to body structure. For example, in one embodiment, the body structures of the polymer alternate between attachment of two different sidechain moieties. In another embodiment, the plurality of sidechains present in the composition is a random mixture of two, three, four, or more chemical substituents.

When in use (e.g., in the presence of nanostructures), at least one head group moiety of the polymeric conductive composition is bound to the nanostructure surface. Optionally, a majority of the head groups (e.g., at least 50%, about 75%, about 90%, about 95%, about 99%, or essentially all of the head groups) are in the bound form. As noted in a previous section, polymerization can be performed either prior to or after binding of the conductive composition to the nanostructure structure; furthermore, the polymer can be partially crosslinked in an initial step, and further crosslinked upon interaction with the nanostructure structure. Thus, compositions including the conductive composition or polymer in combination with the nanostructure structure (e.g., nanostructure-containing matrices) are also contemplated in the present invention.

Nanostructure-Matrix

The conductive compositions would also be useful in charge injection/extraction from other, non nanoscale surfaces, e.g., bulk crystalline materials, etc. Thus, while nanostructures and other nanoscale compositions are preferred embodiment, the conductive compositions described herein can be used for charge injection/extraction from other, non nanoscale surfaces, e.g., bulk crystalline materials, etc., and as such are not limited to either nanoscale and non-nanoscale (e.g., bulk crystalline) assemblies. In one embodiment, the nanostructure-containing matrices comprise a nanostructure having an exterior surface, wherein a portion of the nanostructure exterior surface is cojoined to a conductive composition of the present invention; and a matrix component positioned proximal to the conjugated exterior surface of the nanostructure. The conductive composition employed in the nanostructure-containing matrices can be either a monomeric composition or a polymeric version, e.g., coating the nanostructure. The matrix component can be either a conductive matrix or a nonconductive matrix, depending on the use envisioned for the product. Exemplary matrices for use in the present invention include, but are not limited to, poly-3-hexylthiophene (P3HT), poly(p-phenylene vinylene) (PPV), and poly(2-methoxy, 5 ethyl(2'hexyloxy)p-phenylene vinylene (MEH-PPV).

In another embodiment, the nanostructure-containing matrices of the present invention include, but are not limited to, a nanostructure and a matrix composition positioned proximal to an exterior surface of the nanostructure, wherein the matrix composition comprises a polymerized embodiment of the conductive compositions of the present invention. For example, the conductive polymer having the structure $[T_x\text{-}B_y\text{-}H_z]_n$ is contemplated, wherein H comprises at least one functionalized head group capable of binding to a nanostructure surface; wherein B comprises a body structure comprising one or more conjugated organic moieties, wherein a first conjugated organic moiety is coupled to the at least one functionalized head group; wherein T comprises at least one tail group coupled to the body structure; and wherein x, y, z and n independently comprise integers equal to or greater than 1. The polymerization is achieved via crosslinking of polymerizable units on the elements (for example, the sidechain) of the composition.

In a further embodiment of the present invention, the conductive polymeric composition of the matrix is covalently coupled to a further conductive composition applied to the nanostructure. In a preferred embodiment, this additional conductive composition is functionally and/or electronically matched to one or more components of the conductive polymeric matrix.

Matrices

A wide variety of nanostructure-compatible polymers are known to those of skill in the art (see e.g., Demus et al. (ed.) 1998 *Handbook of Liquid Crystals* Volumes 1-4, John Wiley and Sons, Inc., Hoboken, N.J.); Brandrup (ed.) 1999 *Polymer Handbook*, (John Wiley and Sons, Inc.); Harper 2002 *Handbook of Plastics, Elastomers, and Composites*, 4th edition (McGraw-Hill, Columbus, Ohio); and Kraft et al. (1998) *Angew. Chem. Int. Ed.* 37:402-428. While either conductive or nonconductive polymers can be used in conjunction with the conductive compositions of the present invention, preferred embodiments of the present invention employ conductive polymers.

Exemplary polymers for use in the present invention include, but are not limited to, thermoplastic polymers (e.g., polyolefins, polyesters, polysilicones, polyacrylonitrile resins, polystyrene resins, polyvinyl chloride, polyvinylidene chloride, polyvinyl acetate, or fluoroplastics); thermosetting polymers (e.g., phenolic resins, urea resins, melamine resins, epoxy resins, polyurethane resins); engineering plastics (e.g., polyamides, polyacrylate resins, polyketones, polyimides, polysulfones, polycarbonates, polyacetals); and liquid crystal polymers, including main chain liquid crystal polymers (e.g., poly(hydroxynapthoic acid)) and side chain liquid crystal polymers (e.g., poly [n-((4'(4"-cyanphenyl)phenoxy)alkyl) vinyl ether]). Certain embodiments include conductive organic polymers; see e.g. T. A. Skatherin (ed.) 1986 *Handbook of Conducting Polymers I*. (Marcel Dekker, N.Y.). Examples of conductive polymers for use as matrices of the present invention include, but are not limited to, poly(3-hexylthiophene) (P3HT), poly[2-methoxy, 5-(2'-ethyl-hexyloxy)-p-phenylene-vinylene] (MEH-PPV), poly(p-phenylene vinylene) (PPV), and polyaniline.

Nanostructures

As noted previously, structures for use in the present invention include, but are not limited to nanoscale and non-nanoscale (e.g., bulk crystalline) assemblies. Nanostructures, such as nanocrystals, nanowires, nanorods, nanoparticles and the like, can be fabricated by a number of mechanisms known to one of skill in the art. Furthermore, their size can be controlled by any of a number of convenient methods that can be adapted to different materials. For example, synthesis of nanocrystals of various composition is described in, e.g., Peng et al. (2000) "Shape control of CdSe nanocrystals"0 Nature 404:59-61; Puntes et al. (2001) "Colloidal nanocrystal shape and size control: The case of cobalt" Science 291:2115-2117; U.S. Pat. No. 6,306,736 to Alivisatos et al. (Oct. 23, 2001) entitled "Process for forming shaped group III-V semiconductor nanocrystals, and product formed using process"; U.S. Pat. No. 6,225,198 to Alivisatos et al. (May 1, 2001) entitled "Process for forming shaped group II-VI semiconductor nanocrystals, and product formed using process"; U.S. Pat. No. 5,505,928 to Alivisatos et al. (Apr. 9, 1996) entitled "Preparation of III-V semiconductor nanocrystals"; U.S. Pat. No. 5,751,018 to Alivisatos et al. (May 12, 1998) entitled "Semiconductor nanocrystals covalently bound to solid inorganic surfaces using self-assembled monolayers"; U.S. Pat. No. 6,048,616 to Gallagher et al. (Apr. 11, 2000) entitled "Encapsulated quantum sized doped semiconductor particles and method of manufacturing same"; and U.S. Pat. No. 5,990,479 to Weiss et al. (Nov. 23, 1999) entitled "Organo luminescent semiconductor nanocrystal probes for biological applications and process for making and using such probes."

Growth of nanowires having various aspect ratios, including nanowires with controlled diameters, is described in, e.g., Gudiksen et al (2000) "Diameter-selective synthesis of semiconductor nanowires" *J. Am. Chem. Soc.* 122:8801-8802; Cui et al. (2001) "Diameter-controlled synthesis of single-crystal silicon nanowires" *Appl. Phys. Lett.* 78: 2214-2216; Gudiksen et al. (2001) "Synthetic control of the diameter and length of single crystal semiconductor nanowires" *J. Phys. Chem. B* 105:4062-4064; Morales et al. (1998) "A laser ablation method for the synthesis of crystalline semiconductor nanowires" *Science* 279:208-211; Duan et al. (2000) "General synthesis of compound semiconductor nanowires" *Adv. Mater.* 12:298-302; Cui et al. (2000) "Doping and electrical transport in silicon nanowires" *J. Phys. Chem. B* 104:5213-5216; Peng et al. (2000), supra; Puntes et al. (2001), supra; U.S. Pat. No. 6,225,198 to Alivisatos et al., supra; U.S. Pat. No. 6,036,774 to Lieber et al. (Mar. 14, 2000) entitled "Method of producing metal oxide nanorods"; U.S. Pat. No. 5,897,945 to Lieber et al. (Apr. 27, 1999) entitled "Metal oxide nanorods"; U.S. Pat. No. 5,997,832 to Lieber et al. (Dec. 7, 1999) "Preparation of carbide nanorods"; Urbau et al. (2002) "Synthesis of single-crystalline perovskite nanowires composed of barium titanate and strontium titanate" *J. Am. Chem. Soc.*, 124, 1186; Yun et al. (2002) "Ferroelectric Properties of Individual Barium Titanate Nanowires Investigated by Scanned Probe Microscopy" *Nano Letters* 2, 447; and published PCT application nos. WO 02/17362, and WO 02/080280.

Growth of branched nanowires (e.g., nanotetrapods, tripods, bipods, and branched tetrapods) is described in, e.g., June et al. (2001) "Controlled synthesis of multi-armed CdS nanorod architectures using monosurfactant system" *J. Am. Chem. Soc.* 123:5150-5151; and Manna et al. (2000) "Synthesis of Soluble and Processable Rod-,Arrow-, Teardrop-, and Tetrapod-Shaped CdSe Nanocrystals" *J. Am. Chem. Soc.* 122:12700-12706. Synthesis of nanoparticles is described in, e.g., U.S. Pat. No. 5,690,807 to Clark Jr. et al. (Nov. 25, 1997) entitled "Method for producing semiconductor particles"; U.S. Pat. No. 6,136,156 to El-Shall, et al. (Oct. 24, 2000) entitled "Nanoparticles of silicon oxide alloys"; U.S. Pat. No. 6,413,489 to Ying et al. (Jul. 2, 2002) entitled "Synthesis of nanometer-sized particles by reverse micelle mediated techniques"; and Liu et al. (2001) "Sol-Gel Synthesis of Free-Standing Ferroelectric Lead Zirconate Titanate Nanoparticles" *J. Am. Chem. Soc.* 123:4344. Synthesis of nanoparticles is also described in the above citations for growth of nanocrystals, nanowires, and branched nanowires, where the resulting nanostructures have an aspect ratio less than about 1.5.

Synthesis of core-shell nanostructure heterostructures are described in, e.g., Peng et al. (1997) "Epitaxial growth of highly luminescent CdSe/CdS core/shell nanocrystals with photostability and electronic accessibility" *J. Am. Chem. Soc.* 119:7019-7029; Dabbousi et al. (1997) "(CdSe)ZnS core-shell quantum dots: Synthesis and characterization of a size series of highly luminescent nanocrystallites" *J. Phys. Chem. B* 101:9463-9475; Manna et al. (2002) "Epitaxial growth and photochemical annealing of graded CdS/ZnS shells on colloidal CdSe nanorods" *J. Am. Chem. Soc.* 124:7136-7145; and Cao et al. (2000) "Growth and properties of semiconductor core/shell nanocrystals with InAs cores" *J. Am. Chem. Soc.* 122:9692-9702. Similar approaches can be applied to growth of other core-shell nanostructures. See, for example, U.S. Pat. No. 6,207,229 (Mar. 27, 2001) and U.S. Pat. No. 6,322,901 (Nov. 27, 2001) to Bawendi et al. entitled "Highly luminescent color-selective materials".

Growth of homogeneous populations of nanowires, including nanowire heterostructures in which the different materials are distributed at different locations along the long axis of the nanowire is described in, e.g., published PCT application nos. WO 02/17362, and WO 02/080280; Gudiksen et al. (2002) "Growth of nanowire superlattice structures for nanoscale photonics and electronics" *Nature* 415:617-620; Bjork et al. (2002) "One-dimensional steeplechase for electrons realized" *Nano Letters* 2:86-90; Wu et al. (2002) "Block-by-block growth of single-crystalline Si/SiGe superlattice nanowires" *Nano Letters* 2, 83-86; and U.S. patent application 60/370,095 (Apr. 2, 2002) to Empedocles entitled "Nanowire heterostructures for encoding information." Similar approaches can be applied to growth of other heterostructures.

In certain embodiments, the collection or population of nanostructures is substantially monodisperse in size and/or shape. See e.g., US patent application 20020071952 by Bawendi et al entitled "Preparation of nanocrystallites."

The diameter of the inorganic nanowires can be varied, for example, to control the wavelength emitted by fluorescent nanowires. The diameter of the nanowires is preferably between about 2 nm and about 100 nm, more preferably between about 2 nm and about 5 nm or between about 10 nm and about 50 nm. The length of the nanowires can also be varied. In certain embodiments, the inorganic nanowires have an aspect ratio between about 10 and about 10,000 (e.g., between about 20 and about 10,000, between about 50 and about 10,000, or between about 100 and about 10,000).

The nanowires can be fabricated of essentially any convenient material (e.g., a semiconducting material, a ferroelectric material, a metal, etc.) and can comprise essentially a single material or can be heterostructures.

The nanostructures employed in the nanostructure-containing matrices of the present invention can be fabricated from essentially any convenient materials. E.g., the nanocrystals can comprise an inorganic materials, e.g., a semiconducting material, for example a material comprising a first element selected from group 2 or from group 12 of the periodic table and a second element selected from group 16 (e.g., ZnS, ZnO, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and like materials); a material comprising a first element selected from group 13 and a second element selected from group 15 (e.g., GaN, GaP, GaAs, GaSb, InN, InP, InAs, InSb, and like materials); a material comprising a group 14 element (Ge, Si, and like materials); a material such as PbS, PbSe, PbTe, AlS, AlP, and AlSb; or an alloy or a mixture thereof. Further details regarding nanocrystalline structures for use in the present invention can be found, for example, WO 04/023527.

In a preferred embodiment, the devices of the present invention employ nanocrystals comprising CdSe, CdTe and/or InP as the nanocrystal materials.

Methods of Synthesizing Conductive Compositions

The present invention also provides methods of synthesizing an organic species that facilitates charge transfer, e.g., for use in a nanostructure-containing photovoltaic device. The methods provide a modular approach to the synthesis procedure, such that various head groups, tail groups, and side chains can be independently coupled to the selected body structure.

The methods of the present invention include the steps of a) providing a conjugated organic precursor, wherein the conjugated organic precursor comprises at least three positions available for attachment of substituent modules; b) providing a first substituent module (e.g., a head group or other nanostructure binding moiety), wherein the first substituent module comprises a nanostructure binding moiety, such as a phosphonic acid derivative, a carboxylic acid derivative, an amine derivative, a phosphine derivative, a thiol derivative, a thiophene derivative, or a combination thereof; and c) providing a second substituent module (e.g., a tail group), wherein the second substituent module comprises an alkyne derivative comprising between three and 22 carbons. Optionally, the method further includes providing a third substituent module (e.g., the sidechains), wherein the optional third substituent module comprises an alkyl derivative comprising between one and 22 carbons. The substituent modules are then coupled to the conjugated organic precursor (e.g., the body structure): the first substituent module at a first position, coupling the second substituent module at a second position, and the optional third substituent module at a third position, thereby synthesizing the organic composition. (The first, second and third positions delineate available attachment sites on the conjugated organic moiety, and are not representative either order of attachment during synthesis or IUPAC numbering conventions with respect to the conjugated organic species). Typically, the optional third substituents are coupled to the body structure prior to attachment of the first (head) and second (tail) substituents. Preferably, coupling of the modules to the body structure does not destroy the electronic conjugation of the body structure; furthermore, at least one substituent of the first, second or third substituent modules is capable of binding to a nanostructure surface (or is already bound to a nanostructure surface).

Synthesis of Core Body Structures with Attached Sidechain Moieties

The body structure provides the core of the conjugated organic species of the present invention. Typically, the body structure is a conjugated organic species that either can be functionalized (e.g., by halogenation) or can be reacted with other functionalized moieties (head group, tail group, sidechains) to prepare the conductive compositions of the present invention.

Preferably, the conjugated organic precursor is selected from any of a number of conjugated alkyl moieties or conjugated aryl moieties known to one of skill in the art. Exemplary conjugated organic precursors, such as phenylene, thiophene, ethene, ethyne, aniline, fluorene, and pyridine derivatives, alkenyl moieties, or perylene, phenanthralene, anthracene, alkenyl or other polynuclear aromatic moieties (or polymeric derivatives thereof), have been discussed in previous sections. Optionally, coupling of one or more of the substituent modules to the body structure extends the conjugation of the body structure. Exemplary body structures are provided in Table 2.

TABLE 2

Exemplary conjugated organic moieties for use as Body Structures

| | |
|---|---|
| S1 | 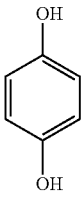 OH / OH |
| S2 | 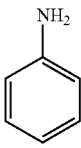 NH$_2$ |
| S3 | 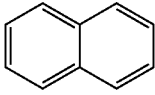 |
| S4 | 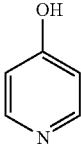 OH |
| S5 |  |
| S6 | 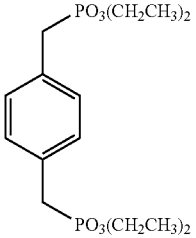 PO$_3$(CH$_2$CH$_3$)$_2$ / PO$_3$(CH$_2$CH$_3$)$_2$ |

One advantage to the convergent component synthesis ("modular") approach to the design and manufacture of the conductive compositions of the present invention is the ability to adjust or "tune" the reactivity of each component for the synthetic scheme. For example, the rate of aryl-aryl coupling can be increased or decreased by selecting an appropriate electron donating group or an electron withdrawing group on each respective component. Electron withdrawing groups tend to accelerate the oxidative addition step in palladium-catalyzed coupling reactions (see, e.g., Kuehl et. al. (1997) *Organometallics* 16: 1897). Thus, by including an electron withdrawing substituent on one of the components, the rate of coupling increases. While not limiting the present invention to a specific mechanism, the enhancement in coupling may be accomplished by the electron withdrawing group weakening the aryl halide or aryl-stannane bond, thus affording a more facile insertion of the palladium catalyst between these moieties. For example, attaching the alkynyl tail group moiety to a thiophene precursor, followed by trimethylstannane attachment, and subsequently coupling this component to the body results in a faster coupling rate and higher overall yields than stepwise assembly. A slower coupling rate is observed if the alkynyl moiety was added after the thiophene and body component were coupled in a divergent stepwise fashion.

The conductive compositions of the present invention often include one or two sidechains, or "arms," (i.e., third and fourth substituent modules) coupled to the body structure. In a preferred embodiment of the methods, the optional third and fourth substituent modules are coupled to the conjugated organic precursor prior to coupling the first (head) and/or second (tail) substituent modules. For example, the conjugated organic precursor can be alkylated at the third position having a hydroxyl or amine moiety, to form an O-linked or N-linked sidechain-substituted intermediate composition.

For example, sidechain moieties functionalized with a halide (e.g., I or Br) can be used to alkylate the selected conjugated organic species and provide a sidechain-substituted body structure using procedures known in the art. As an example, for the hydroxyl-containing conjugated organic precursors described herein, providing the third substituent module comprises providing about 1.1 molar equivalents of a halogenated derivative of the selected sidechain substituent; and coupling the third substituent module with the conjugated organic precursor comprises the steps of a) combining the halogenated sidechain derivative with the conjugated organic precursor in the presence of, e.g., potassium carbonate ($K_2CO_3$) and dimethyl formamide (DMF), to form a reaction mixture; and b) heating the reaction mixture to about 70° C., thereby coupling the third substituent to the conjugated organic moiety. A similar reaction can be designed for coupling functionalized sidechain moieties to amine-containing body structure precursors. Alternatively, the sidechain-coupled body structure for use as a substrate in generating the compositions of the present invention can be purchased from various suppliers (e.g., SIGMA-Aldrich) when available.

In the case of body structures having two (or more) identical sidechain moieties, the coupling reactions for the third and fourth substituents are typically performed simultaneously (e.g., in a single reaction mixture).

One preferred body structure used in the methods and compositions of the present invention is hydroquinone(1,4-dihydroxybenzene). Table 3 provides exemplary substrates for use in the synthesis procedures described herein, based upon a hydroquinone body structure having two sidechain substitutions coupled at the hydroxyl positions of the core hydroquinone structure.

TABLE 3

Exemplary Body Structures with Attached Sidechains

A1 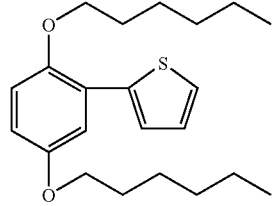

TABLE 3-continued

Exemplary Body Structures with Attached Sidechains

A2 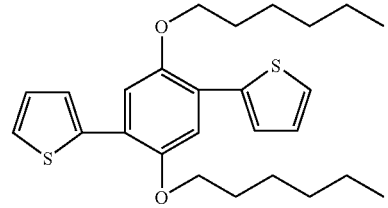

A3 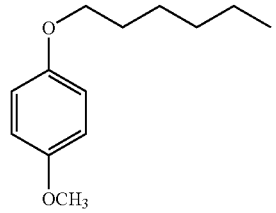

B1 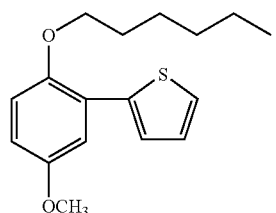

B2 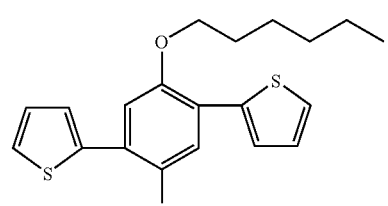

B3 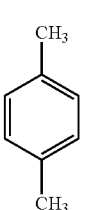

C1 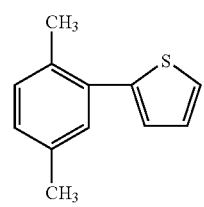

C2

TABLE 3-continued

Exemplary Body Structures with Attached Sidechains

C3: benzene ring with CH₃ at positions 2 and 5, and thiophene groups at positions 1 and 4

D1: benzene ring with CH₂PO₃(CH₂CH₃)₂ groups at 1 and 4 positions

D2: benzene ring with two CH₂PO₃(CH₂CH₃)₂ groups and a thiophene substituent

D3: benzene ring with two CH₂PO₃(CH₂CH₃)₂ groups and two thiophene substituents

E1: 4-methoxyphenyl ether with 2-ethylhexyloxy group (OCH₃ and O-CH₂-CH(C₂H₅)-C₄H₉)

E2: benzene ring with 2-ethylhexyloxy, OCH₃, and thiophene substituents

E3: benzene ring with 2-ethylhexyloxy, OCH₃, and two thiophene substituents

TABLE 3-continued

Exemplary Body Structures with Attached Sidechains

A4: benzene ring with two hexyloxy groups and bithiophene substituents on both sides As indicated in the tabular data above, the two sidechain elements at positions 1 and 4 of the hydroquinone body structure can, but need not, be the same chemical entity.

Synthesis of Head Group Moieties

The first substituent module comprises the functionalized nanostructure-binding head group. For example, for embodiments in which the first substituent module comprises diethylphosphite, coupling the first substituent module to the body structure can be performed via a palladium-catalyzed phosphite-aryl coupling reaction.

In alternate embodiment, a larger head module (precursor) is prepared having a nanostructure binding moiety (e.g., a phosphite) and a conjugated species (e.g., a benzene ring or a thiophene) for linking the nanostructure binding moiety to the body structure. Synthesis of the head module can be achieved, for example, by providing an arylhalide core structure and performing two lithium-halogen exchange reactions. The arylhalide core structure is lithiated at a first halide position and reacted with chlorotrimethylsilane (TMSCl) to yield a TMS-aryl intermediate core structure; the TMS-intermediate core structure is then lithiated at a second halide position and reacted with trimethyltinchloride (Me₃SnCl) to yield a stannylated second intermediate. Optionally, the lithiating reactions can be performed in the reverse order. The product of these reactions is then combined with, e.g., a halogenated thiophene as the conjugated species, to form the first substituent module, which in this embodiment comprises a TMS-aryl-thiophene derivative. The nanostructure-binding moiety (e.g., a phosphite group) can then be coupled to the aryl portion of the bound head group module, via a palladium-catalyzed mechanism (either before or after attachment of the head module to the body structure).

Exemplary nanostructure binding moieties that can be used in the present invention include, but are not limited to, those depicted in Table 4.

TABLE 4

Exemplary Synthetic Substrates having nanostructure Binding Moieties for use as Head Groups

| | |
|---|---|
| H1 | —PO₃H₂ |
| H2 | —PO₃(CH₂CH₃)₂ |
| H3 | thiophene—PO₃H₂ |
| H4 | phenyl—PO₃H₂ |

TABLE 4-continued

Exemplary Synthetic Substrates having nanostructure
Binding Moieties for use as Head Groups H5 [structure: thiophene-phenyl-PO$_3$H$_2$]

Synthesis of Tail Moieties

The conductive composition also includes a tail group, typically positioned distal to the nanostructure-binding head group. Optionally, the tail group can also include one or more nanostructure binding moieties; in these embodiment, the conductive compositions can be used as a linker between adjacent nanostructures or nanostructures. Optionally, for embodiments having self-organizing properties incorporated therein, the conductive compositions of the present invention can also be employed as alignment ligands, e.g., for orienting and/or arranging the associated nanostructures (see, for example, U.S. Ser. No. 10/656,911 and PCT application PCT/US03/27845 co-filed herewith).

Coupling of the second substituent module(e.g., the alkyne-containing tail moiety) can be accomplished by performing an aryl coupling reaction using palladium catalysts. Exemplary reaction protocols include, but are not limited to, Sonogashira couplings (Sonogashira et al. 1975 *Tetrahedron Lett.* 50: 4467-4470), Suzuki couplings (Miyaura 1979 *Tetrahedron Lett.* 3437), Hartwig-Buchwald couplings (for N-linked substituents), Heck reactions (Patel et al. 1977 *J. Org. Chem.* 42:3903), and the like. Alternatively, copper-mediated reactions such as the Ullmann coupling and Stephens-Castro coupling can be used to couple the second substituent module to the body structure. Optionally, the catalyst (for this or for other reactions described herein) can be provided on a solid support or coupled to a soluble polymer, to improve recovery of the material (see, for example, Bergbreiter "Soluble polymer-bound catalysts" Bergbreiter and Martin (Eds.), (1989) *Functional Polymers* (Plenum Press, New York, pp. 143-158); Tafesh and Beller (1995) "First Selective Reduction of Aromatic Nitro Compounds Using Water Soluble Catalysts" *Tetrahedron Lett.* 36:9305.

Exemplary chemical constituents for use as tail group moieties in the present invention include, but are not limited to, the structures shown in Table 5.

TABLE 5

Exemplary Alkyne precursors for use as Tail Groups

T1 [structure: alkyl chain with terminal alkyne]

T2 [structure: alkyl chain with alkyne-thiophene]

T3 [structure: alkyl chain with alkyne-phenyl]

Modular Synthesis of Conductive Compositions

Figure 2:
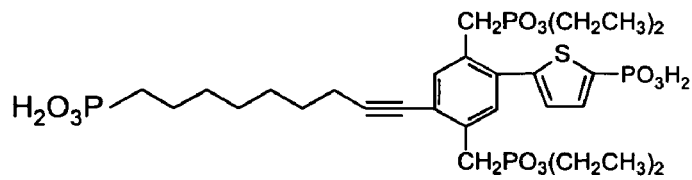
FIG. 2 provides additional exemplary conductive compositions of the present invention.
Figure 2:
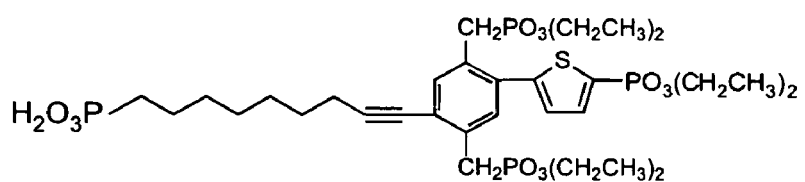
Figure 2:
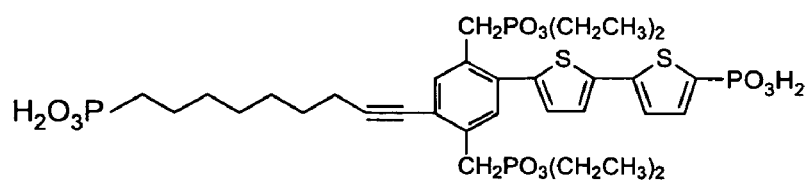
Figure 2:
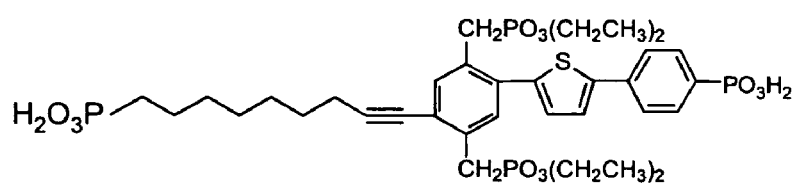
Figure 2:
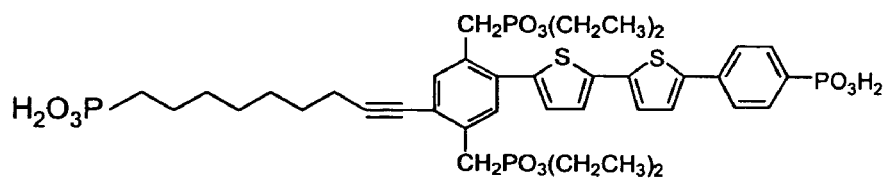
Figure 2:
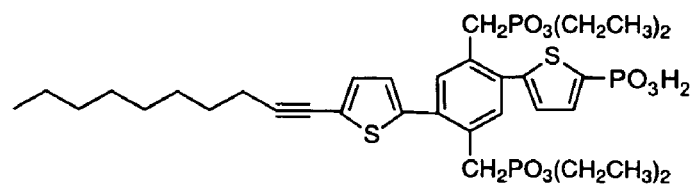
Figure 2:
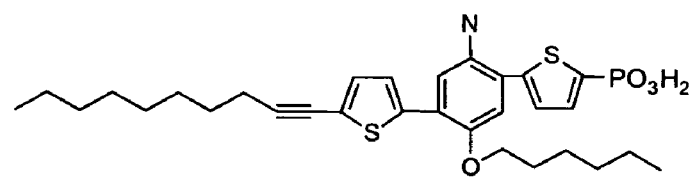
Figure 2:
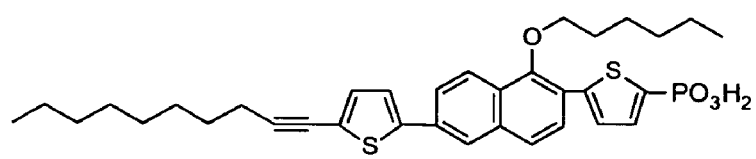
Figure 2:
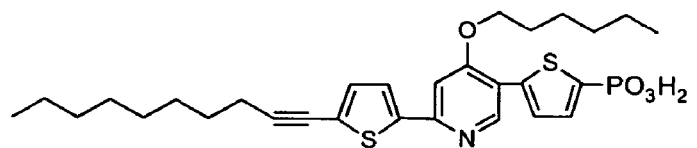
Figure 2:
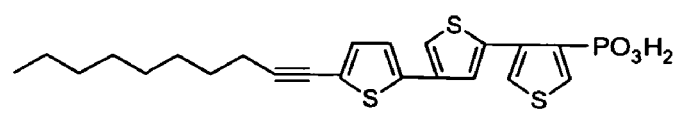

By preparing the body structure (with or without the optional accompanying sidechains), head group and tail group moieties separately, various different conductive compositions can easily and rapidly be prepared. This modular approach to the chemical synthesis of the conductive compositions of the present invention lends itself to a number of combinations of various head moieties, tail groups, and optional side chain elements, some of which are provided in FIG. 1 and FIG. 2.

Optionally, the synthetic methods further include the step of coupling the head group to an external surface of a structure, such as nanocrystal (or other nanostructure), thereby providing a nanocrystal-bound composition. Alternatively, the head group can be coupled to a non-nanoscale surface and the conductive composition employed in conjunction with a non-nanoscale semiconductor composition. Semiconductor and nanoscale semiconductor compositions are known in the art. Nanostructures having external surfaces that can be employed in the coupling step can be prepared from any of the exemplary semiconducting materials described previously. In a preferred embodiment, the nanocrystals are group II/VI or group III/V structures, for which coupling the head group to the external surface of a nanocrystal comprises, e.g., association of free electrons available in the head group with proximal metal moieties of the nanocrystal. The head group module employed can be chosen based upon the composition of the structure or nanoscale structure to be contacted, such that a conductive composition can be prepared, e.g., for any nanostructure/nanocrystal composition, without undue experimentation.

Furthermore, the methods of the present invention can also optionally include the step of polymerizing the organic composition after coupling the composition to the nanostructure surface, thereby forming a polymerized organic composition.

Nanostructure-containing device of the present invention are particularly suited for use in a photovoltaic device. See, for example, Huynh et al. (2002) *Science* 295:2425-2427; Huynh et al. (1999) *Adv. Mater.* 11:923-927; Greenham et al. (1996) *Phys. Rev. B-Condens Matter* 54:17628-17637; and Greenham et al. (1997) *Synthetic Metals* 84:545-546; as well as the exemplary nanocrystal-containing photovoltaic devices described in WO 2004/022637 and 04/023527. The conductive compositions of the present invention can also be employed in the polymer/nanocomposite photovoltaic devices described in U.S. Pat. Nos. 6,239,355; 6,512,172, as well as dye-sensitized crystal photovoltaic devices, e.g., as described in U.S. Pat. Nos. 5,728,487; and 6,245,988.

Synthesis of water soluble semiconductor nanocrystals capable of light emission are described, for example, in U.S. Pat. No. 6,251,303 to Bawendi et al. entitled "Water-soluble fluorescent nanocrystals" (Jun. 6, 2001) and U.S. Pat. No. 6,319,426 to Bawendi et al. titled "Water-soluble fluorescent semiconductor" (Nov. 20, 2001).

Method of Modifying Interaction Between Nanostructure and Matrix

As an additional aspect, the present invention also provides methods of modifying an interaction between a nanostructure and an external matrix. The methods include the steps of a) treating a nanostructure with the conductive composition of the present invention; and b) forming a nanostructure-containing matrix comprising the treated nanostructure and a matrix composition. Optionally, treating the nanostructure can also include polymerizing the conductive composition to form a polymerized conductive composition. In some embodiments of the methods, the polymeric conductive composition described herein are employed as matrices in the methods.

Uses of the Methods, Devices and Compositions of the Present Invention

Modifications can be made to the methods and materials as described above without departing from the spirit or scope of the invention as claimed, and the invention can be put to a number of different uses, including:

The use of any method herein, to prepare a conductive composition for use in modifying an interaction involving a nanostructure, e.g., an interaction between a nanocrystal and a matrix.

The use of any method herein, to associate a conductive composition of the present invention with one or more nanostructures.

The use of a method or a conductive composition of the present invention in the manufacture of a nanostructure-containing device.

A kit or system using of any one of the conductive compositions, nanostructure:conductive composition; nanostructure:matrix compositions, or methods hereinbefore described. Kits will optionally additionally comprise instructions for performing the methods, packaging materials, one or more containers which contain the conductive compositions or materials used to prepare the compositions, and/or the like.

In an additional aspect, the present invention provides kits embodying the methods and devices herein. Kits of the invention optionally comprise one or more of the following: (1) various components (body structures, head groups, tail groups, sidechains) for the modular synthesis of the conductive compositions of the present invention; (2) one or more preparations of nanocrystals or other nanostructures; (3) components and/or instructions for the preparation of nanocrystal:matrix compositions; (4) instructions for practicing the methods described herein; and/or (5) packaging materials.

In a further aspect, the present invention provides for the use of any component or kit herein, for the practice of any method herein, and/or for the use of any apparatus or kit to practice any method herein.

EXAMPLES

The following examples are offered to illustrate, but not to limit the claimed invention. It is understood that the examples and embodiments described herein are for illustrative purposes only and that various modifications or changes in light thereof will be suggested to persons skilled in the art and are to be included within the spirit and purview of this application and scope of the appended claims.

Methods for the synthesis of the conductive compositions of the present invention are provided herein and in the accompanying figures. Additional information regarding synthesis techniques can be found in, for example, Fessendon and Fessendon, (1982) *Organic Chemistry*, 2nd Edition, Willard Grant Press, Boston Mass; Carey & Sundberg, (1990) *Advanced Organic Chemistry*, 3rd Edition, Parts A and B, Plenum Press, New York; and March (1985) *Advanced Organic Chemistry*, 3rd Edition, John Wiley and Sons, New York. Optionally, the standard chemical reactions described therein are modified to enhance reaction efficiency, yield, and/or convenience.

Example 1

Synthesis of Model Conductive Composition 4-decynyl-benzene-1-phosphonic Acid

Figure 3:
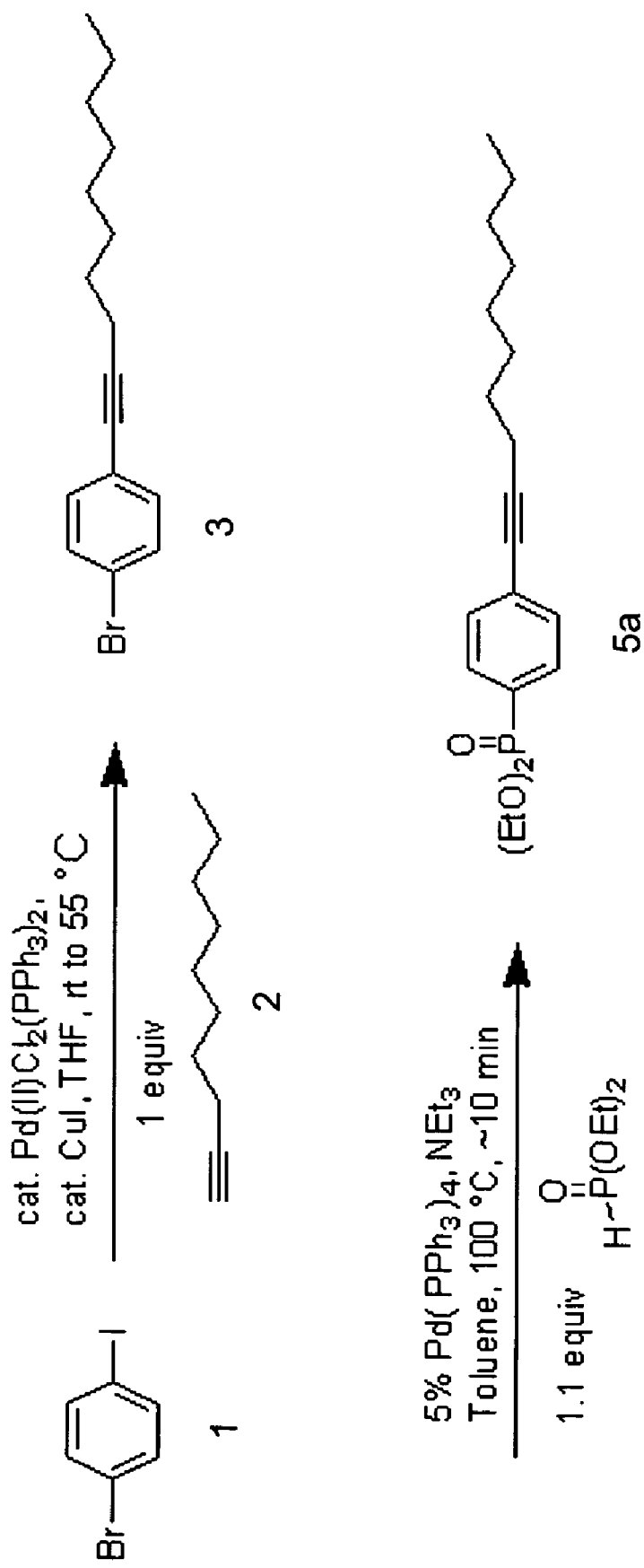
FIG. 3 depicts a chemical synthesis scheme for one embodiment of the compositions of the present invention.

A synthesis protocol was designed to test the modular approach to synthesis of the conductive compositions of the present invention (FIG. 3). The model conductive composition 5b was prepared using 1-iodo-4-bromobenzene as a precursor to the body structure, 1-decyne as the tail group moiety, and diethylphosphite as the head group moiety. To a 500 mL schlenk flask with egg-shaped stirbar under argon, palladium dichloride (1.0 mmol, 0.177 g), copper(I) iodide (2.36 mmol, 0.450 g), and triphenylphosphine (2.0 mmol, 0.525 g) were added in a glovebox under argon. On a schlenk line, 1-iodo-4-bromo-benzene (50 mmol, 14.15 g, compound 1) was added, the vessel was stoppered, and the flask was placed under vacuum and backfilled with argon (3×). The flask was fitted with a septum under positive argon pressure and degassed diisopropyl amine (100 mL) was added via cannula under positive argon pressure with stirring. Next, degassed 1-decyne (50 mmol, 6.91 g, compound 2) was added via syringe under argon. Finally, dry, degassed tetrahydrofuran was added via cannula transfer under argon, the vessel sealed with a glass stopper and allowed to stir at ambient for 16 h followed by heating to 55° C. for one hour. After cooling to ambient temperature, the solvent was removed by roto-evaporation, the residue dissolved in diethyl ether (200 mL) and washed with ammonium chloride (sat. aqueous, 3×100 mL). The organic layer was separated and dried over magnesium sulfate, filtered and the solvent removed by roto-evaporation. The resulting oil was dissolved in hexanes and plugged through silica gel. Removal of the solvent resulted in a yellow oil of 4-decynyl-bromo-benzene 3 (14.34 g, 98% yield).

Figure 9:
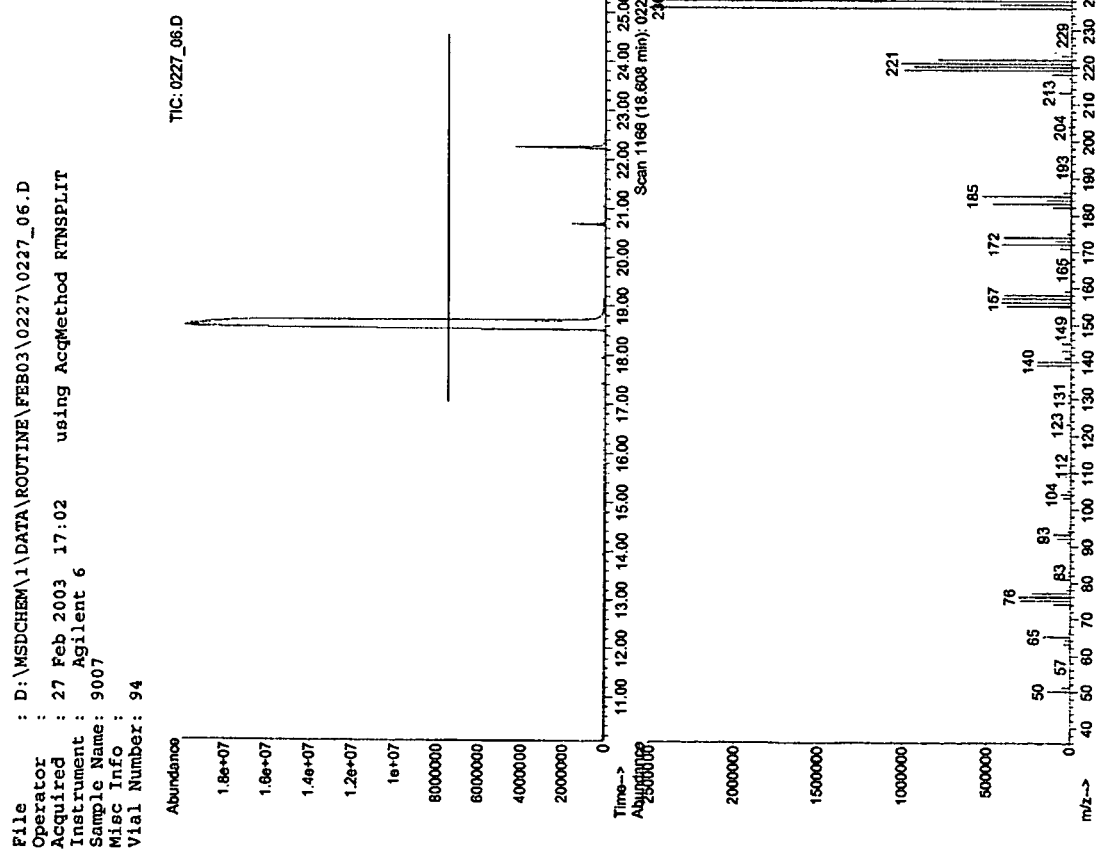
FIGS. 9 through 19 provide mass spectral and/or NMR data for exemplary intermediates and compositions of the present invention.

This material was used without further purification for the attachment of phosphonate ester moiety. To a 100 mL schlenk tube with a Teflon valve and stirbar containing the above compound 3 (23.87 mmol, 7.0 g), palladium(0)tetrakis[triphenylphosphine] (1.19 mmol, 1.38 g) was added. On a schlenk line, degassed triethyl amine (11 mL) and degassed toluene were then sequentially added via syringe under argon. Next, degassed diethyl phosphite 4 (26.26 mmol, 3.63 g) was added via syringe under argon. The reaction vessel was sealed, the mixture stirred and heated to 100° C. for 2 h. The solvent was removed by roto-evaporation, and the residue dissolved in ethyl acetate (200 mL) and washed with saturated aqueous ammonium chloride (3×75 mL), dried over sodium sulfate, filtered and the solvent removed by roto-evaporation. Isolation by silica gel chromatography (1:1 Ethyl Acetate:Hexanes) afforded 4-decynyl-benzene-1-diethylphosphonate 5a as a colorless oil (7.19 g, 90% yield) $^1$H NMR (CDCl$_3$) δ 7.70 (m, 2 H), 7.45 (m, 2 H), 4.10 (m, 4 H), 2.42 (t, 2 H), 1.61 (m, 2 H), 1.45 (m, 2H), 1.32 (t, 8H), 1.27 (m, 6 H), 0.89 (t, 3 H). MS signal derived from the phosphonated benzyl ring without the coupled tail group (a side product of the reaction) is shown in FIG. 9.

Figure 18:
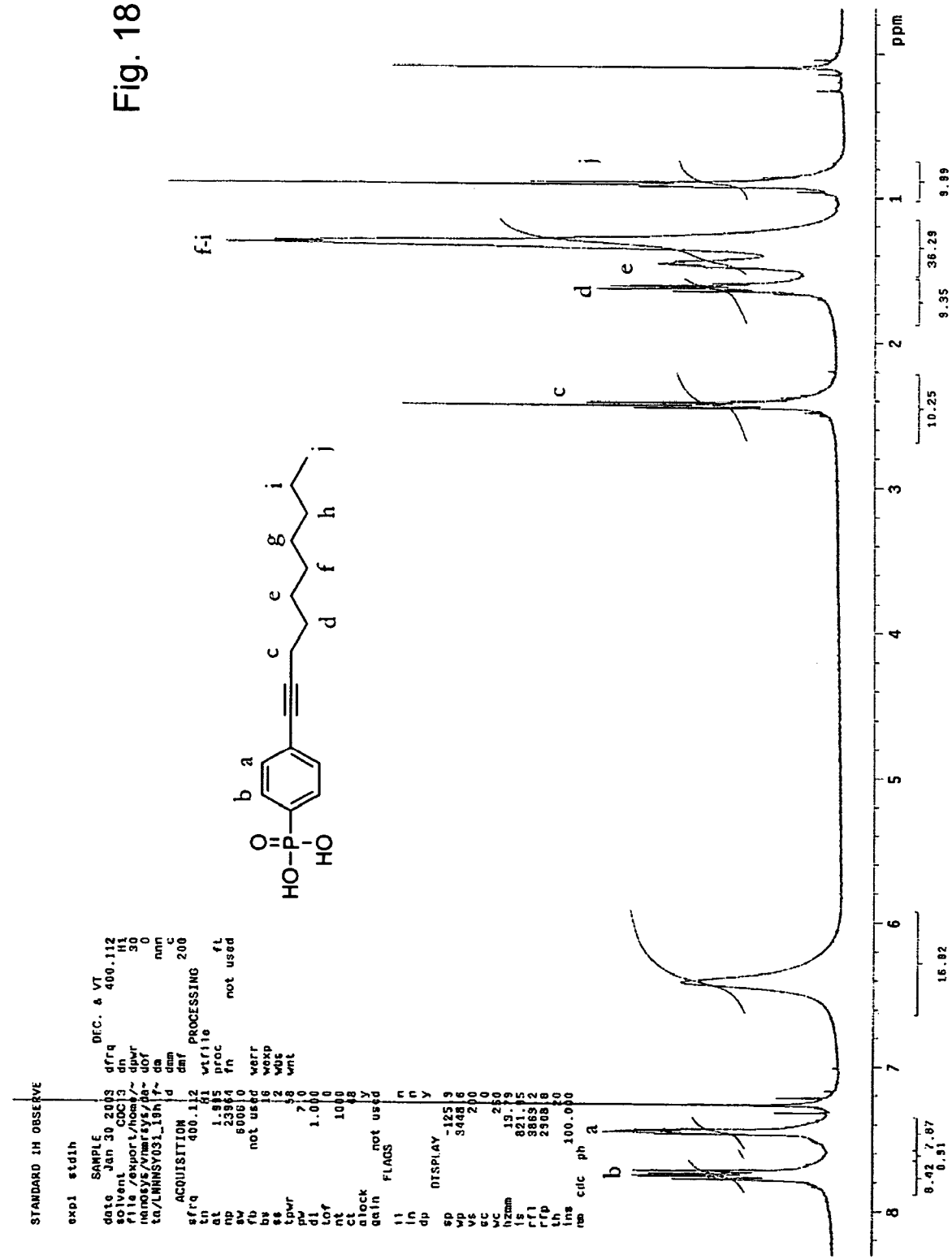
Figure 19:
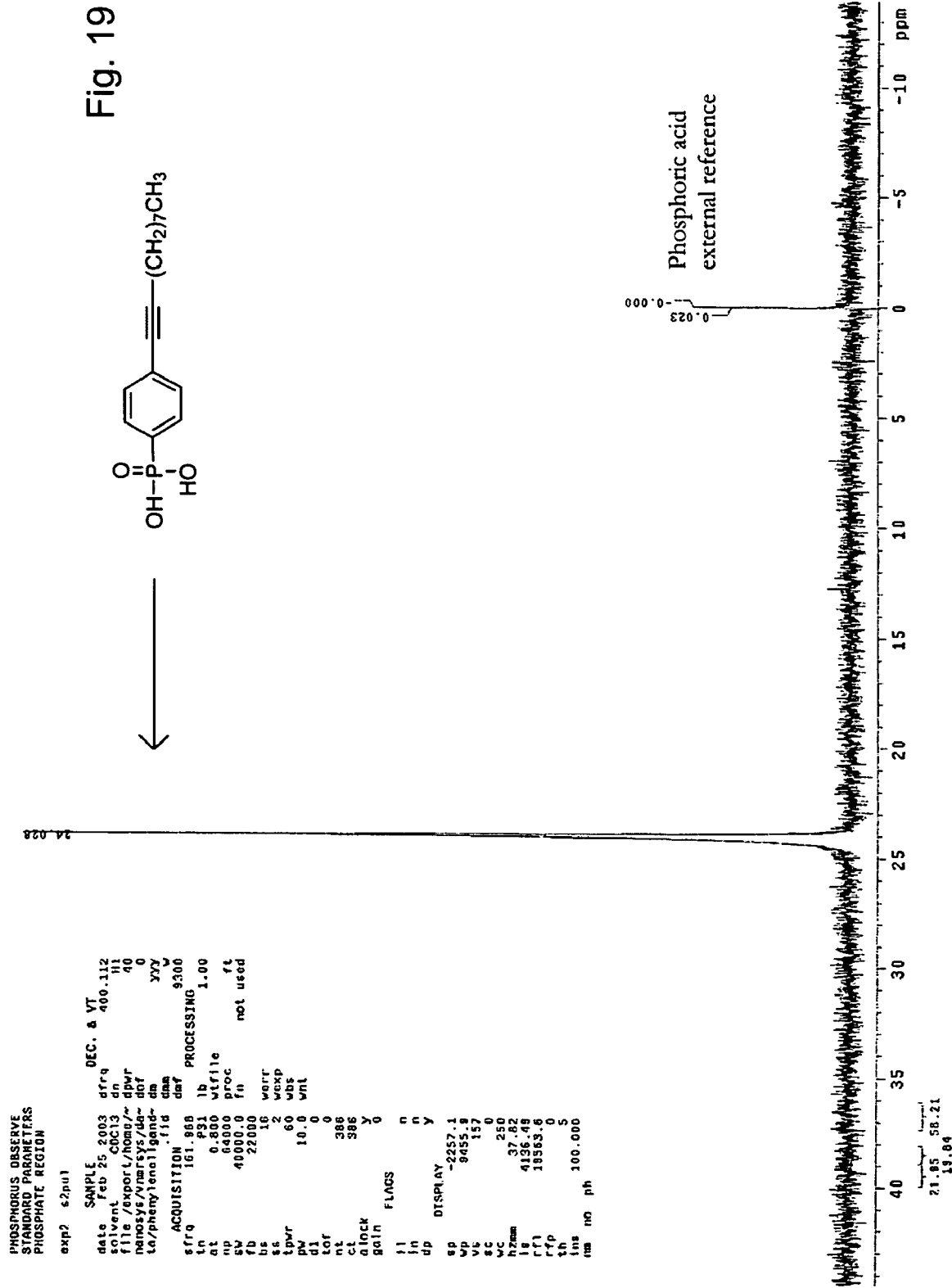

Hydrolysis of the ester to the phosphonic acid was accomplished by the following. To a 250 mL schlenk flask containing compound 5a (10 mmol, 3.5 g) and dry dichloromethane (65 mL), Trimethylsilylbromide (40 mmol, 6.1 g) was added via syringe under argon with stirring. After stirring for 4.5 h at ambient temperature, the solvent was removed in vacuo on the schlenk line. Next acetone (32 mL) and water (0.775 mL) were added and the mixture stirred at ambient temperature for 45 min. Removal of the acetone/water by roto-evaporation followed by addition of dichloromethane and roto-evaporation of all solvent afforded the phosphonic acid derivative 5b (2.9 g, 100% yield). $^1$H NMR (CDCl$_3$, FIG. 18) δ 7.75 (m, 2 H), 7.45 (m, 2 H), 2.44 (t, 2 H), 1.63 (m, 2 H), 1.45 (m, 2H), 1.32 (t, 8H), 0.93 (t, 3 H). {1H}$^{31}$P NMR (CDCl$_3$, FIG. 19) δ 24.0

Example 2

Synthesis of Conductive Composition 16

Figure 4:
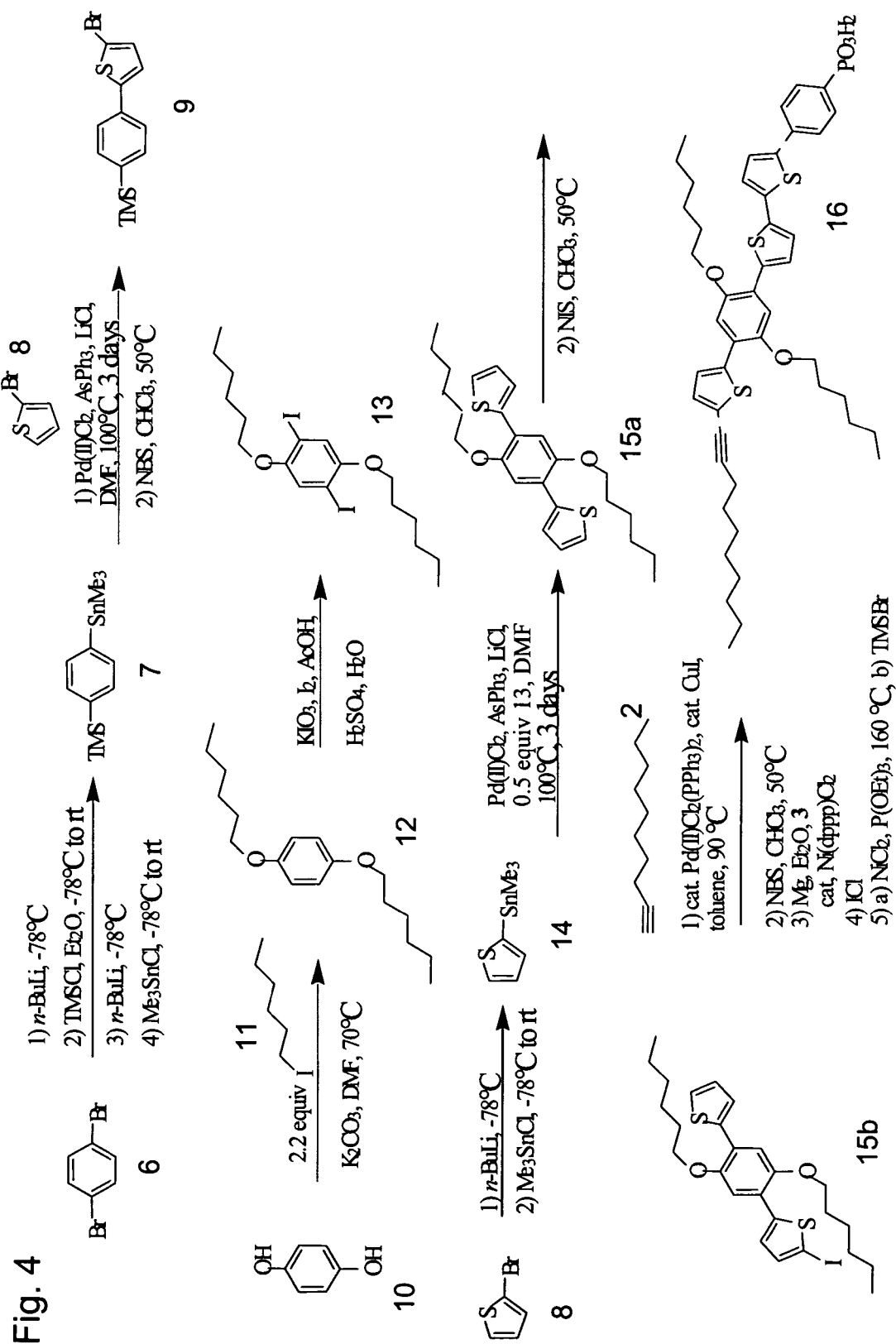
FIG. 4 depicts a chemical synthesis scheme for another embodiment of the compositions of the present invention.

One advantage to the methods of the present invention is the modular approach to synthesis of the various conductive compositions of interest. Using this approach allows for the preparation and use of common synthetic intermediates and core structures. An exemplary synthesis scheme for the preparation of a conductive composition of the present invention is depicted in FIG. 4 and described in further detail herein. In this modular approach, the various components of the composition (body structure, head group, tail group) are synthesized as individual structures, which are then coupled together to form the conductive composition.

Preparation of the Head Group Precursor

One common intermediate in the synthesis of some embodiments of the present invention is the activated head group precursor compound 9, which can be prepared based upon known synthetic protocols such as those provided in FIG. 4.

Coupling of Sidearm Moieties to the Body Structure

Figure 14:
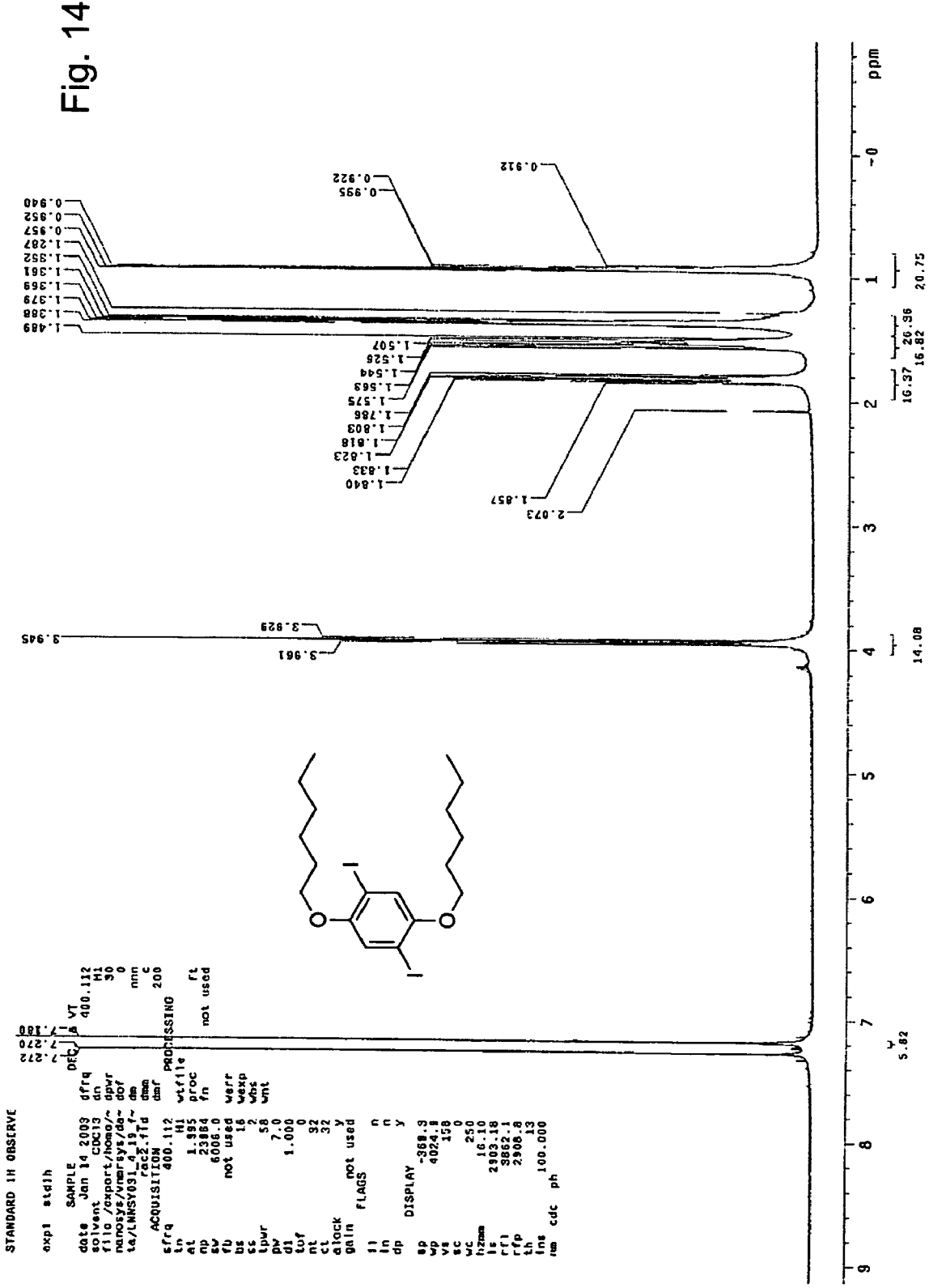

In many of the embodiments of the present invention, the sidearm moieties are coupled to the body element prior to incorporation of the head and tail elements. One preferred sidearm component for use in the conductive composition is an O-linked hexyl moiety. As such, another intermediate useful for the synthesis of 2,5-dihexoxy-containing conductive compositions is 1,4 diiodo-2,5-dihexoxybenzene (compound 13; see also FIG. 14). This core structure consisting of an aromatic body structure (benzene) and the two O-linked sidearm chains can be prepared from hydroquinone (compound 10) by standard procedures such as provided in FIG. 4. While the following syntheses focus on hydroquinone-based body structures (e.g., various sidechains O-linked to a benzene core), other aryl and/or aromatic core structures are also contemplated and can be used to generate conductive compositions of the present invention. Exemplary conductive compositions employing alternative core structures are shown, for example, in FIG. 2.

Addition of Thiophene Elements to Body Structure

Figure 16:
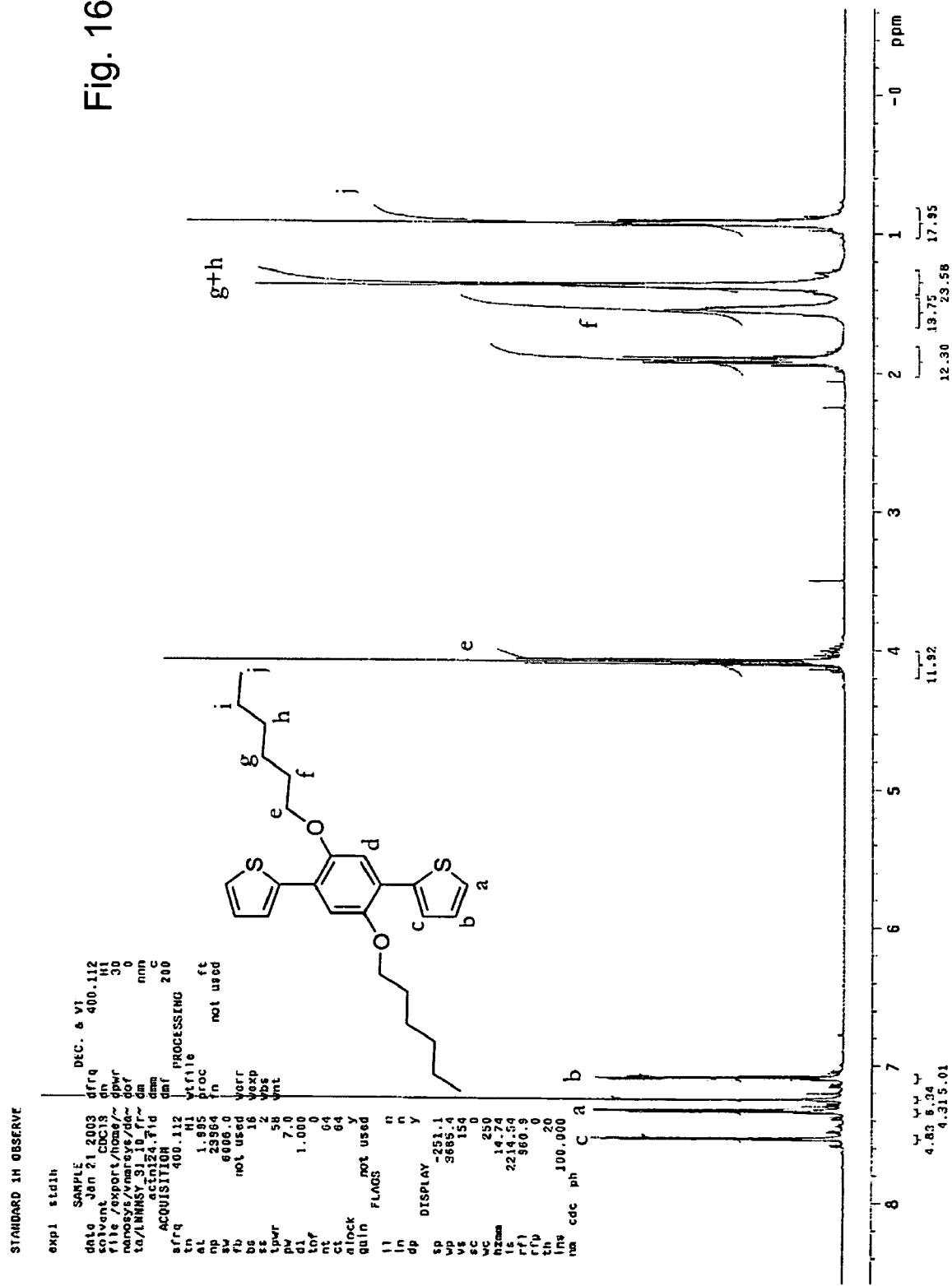

In a preferred embodiment, the body structure includes one or more thiophene moieties coupled to an aromatic ring core structure. This can be achieved synthetically by either providing thiophene-containing core structures or by providing thiophene-containing head or tail group moieties. An exemplary thiophene-containing body structure (including the coupled sidearms) is 1,4-dithiophene-2,5-dihexoxybenzene (compound 15a). This compound, which is a precursor to the iodinated intermediate compound 15b, is prepared as follows. To a 100 mL schlenk tube with stirbar and Teflon valve, palladium dichloride (1.0 mmol, 0.177 g), triphenylarsene (2.0 mmol, 0.610 g), and LiCl (20 mmol, 0.859 g) were added in a glove box. On a schlenk line, 1,4-diiodo-2,5-dihexoxybenzene 13 (10 mmol, 5.30 g), was added and the vessel placed under vacuum and backfilled with argon (3×). Next, degassed dimethylformamide (DMF) was cannula transferred under positive argon pressure. The vessel was sealed and heated to 100° C. for up to 6 days. The reaction mixture was cooled and diluted with ethyl acetate (200 mL) and washed with saturated aqueous sodium bicarbonate (125 mL), deionized water (50 mL) and brine (150 mL). The organic layer was placed under vacuum and the solvent removed and trapped in a 250 mL schlenk flask. Purification by flash chromatography (Ethyl acetate:hexanes, 0, 1, 2, and 5% gradient) and solvent removal by roto-evaporation afforded yellow crystals of 1,4-dithiophene-2,5-dihexoxybenzene (2.2 g, 49% yield, compound 15a). $^1$H NMR (CDCl$_3$, FIG. 16) δ 7.53 (d, 2 H), 7.34 (d, 2 H), 7.25 (s, 2H), 7.09 (dd, 2 H), 4.09 (t, 4H), 1.91 (m, 4 H), 1.55 (m, 4H), 1.36 (m, 8H), 0.93 (t, 6 H); $^{13}$C{$^1$H} (CDCl$_3$) δ 149.2, 139.3, 126.8, 125.8, 125.2, 123.0, 112.9, 69.9, 31.9, 29.7, 26.2, 22.9, 14.4.

Figure 13:
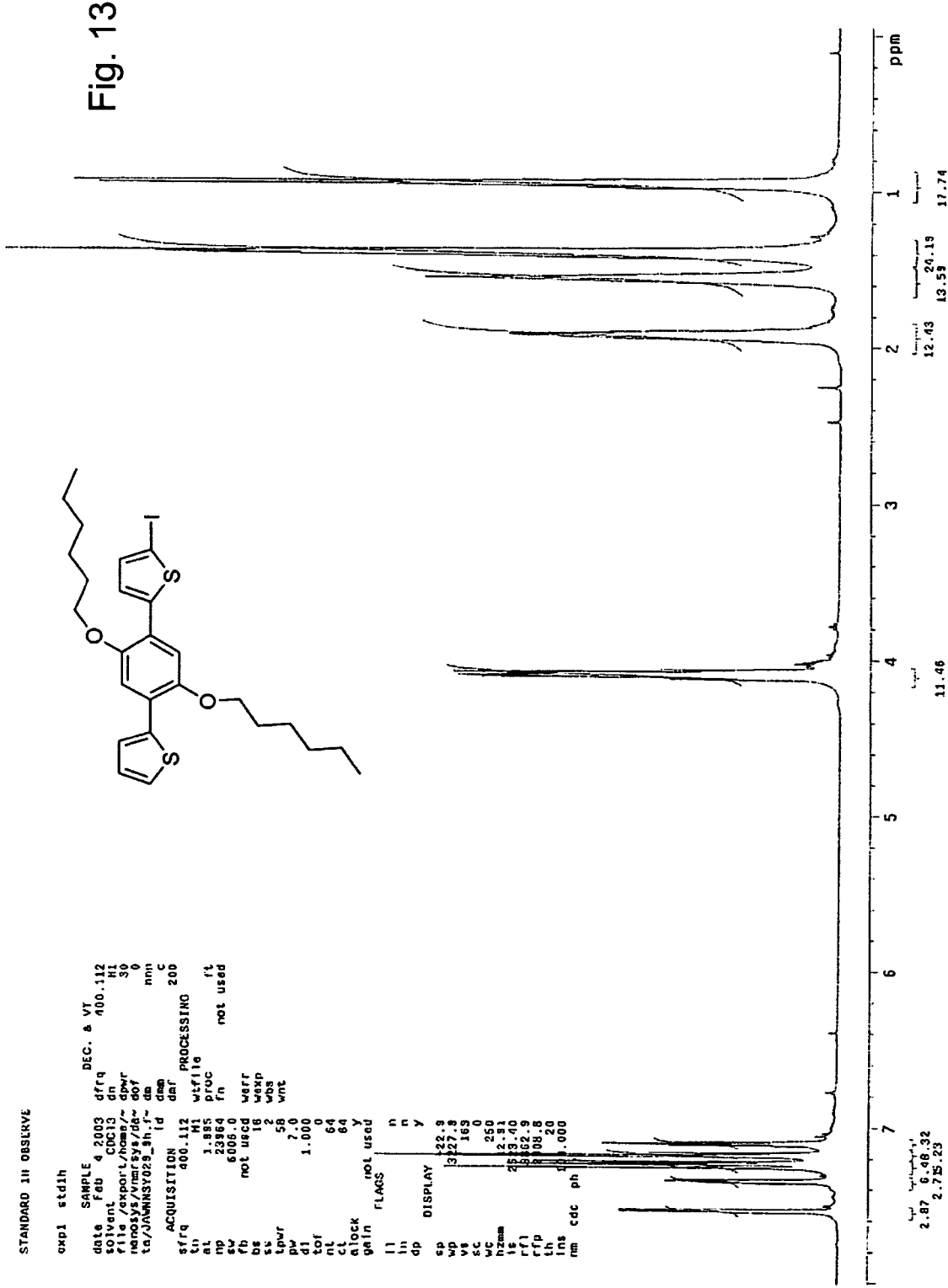

Intermediate 15a was then converted to compound 15b by iodination of one of the thiophene elements as follows. To a 100 mL schlenk flask with Teflon valve and stirbar, 1,4-dithiophene-2,5-dihexoxybenzene 15a (2.49 mmol, 1.10 g) was added and the flask closed with a stopper and placed under vacuum and backfilled with argon (3×). Next, dry chloroform (30 mL) was cannula transferred under positive argon pressure and the mixture stirred. To the stirred solution under argon, N-iodosuccinimide (2.49 mmol, 0.560 g) was added in one portion, the reaction vessel sealed with a Teflon sleeved stopper and the reaction mixture stirred at ambient temperature for 4.5 h then heated to 40° C. and stirred for an additional 22 h. After cooling the crude reaction mixture was plugged through silica gel (5% ethylacetate:95% hexane), then washed with 10% aqueous sodium thiosulfate (3×50 mL), brine (50 mL) and the organic layer dried over sodium sulfate filtered and the solvent removed by roto-evaporation to afford the crude material compound 15b as a yellow oily solid (1.40 g, 99% yield). $^1$H NMR (CDCl$_3$, FIG. 13) δ 7.53 (m, 1 H), 7.43 (d, 1H), 7.35 (m, 1 H), 7.26-7.20 (m, 3H), 7.13 (d, 1H) 7.09 (dd, 1 H), 7.02 (s, 1H), 4.09 (t, 4H), 2.45 (t, 2H), 1.93 (m, 4 H), 1.70-1.25 (m, 24H), 0.94 (m, 9 H); MALDI-TOF MS (M+H) 569 m/z.

Coupling of the Tail and Head Groups

Addition of the tail group and head group moieties to the iodinated intermediate 15b leads to conductive composition 16. The tail moiety is coupled to the iodinated thiophene element of the body structure as shown in FIG. 4, in a manner similar to that previously described for compound 5a. Coupling of the head group is the final step in the synthesis of the desired conductive composition 16.

Example 3

Synthesis of Compositions Having Asymmetric Sidearm Elements

Figure 5:
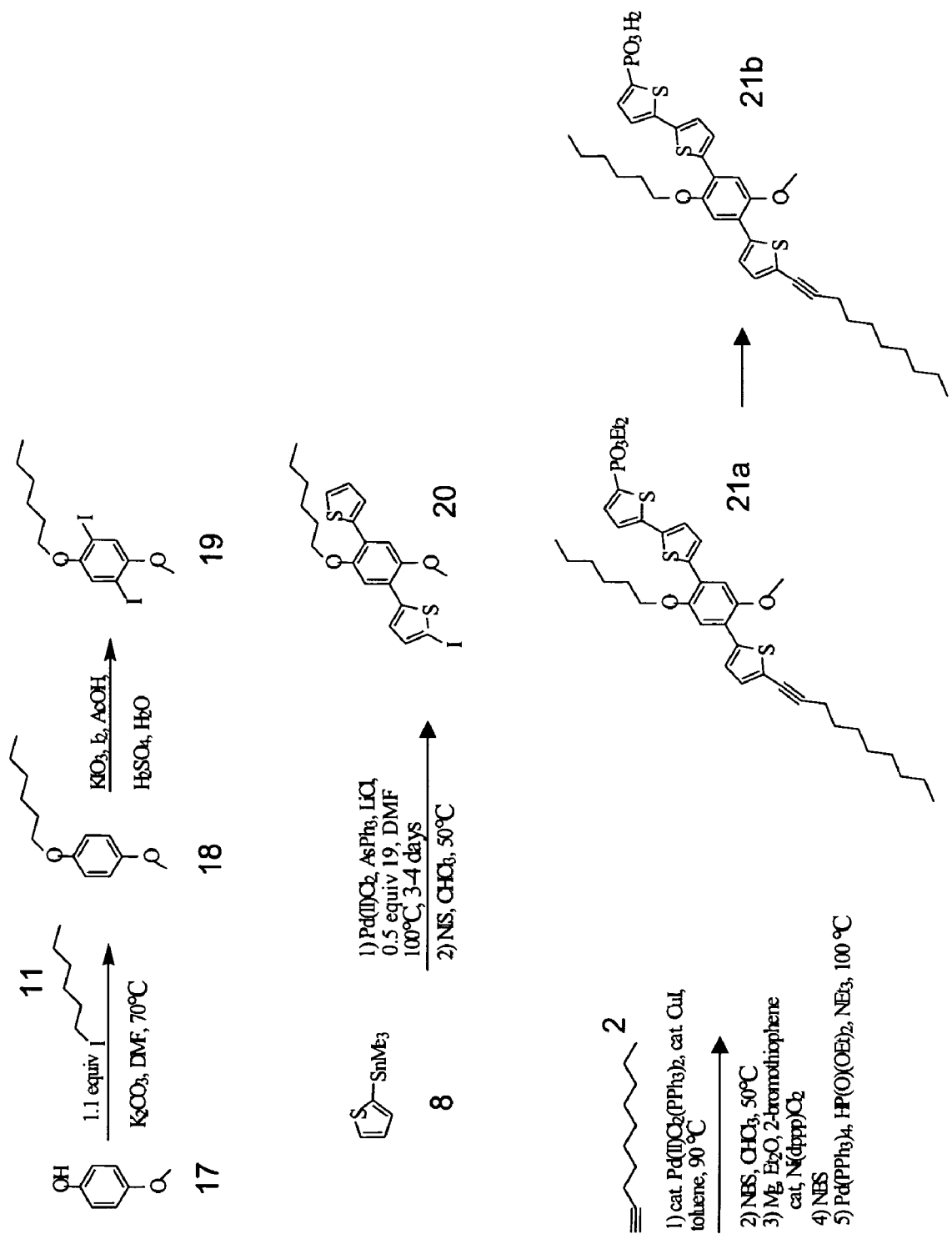
FIG. 5 depicts a chemical synthesis scheme for a further embodiment of the compositions of the present invention.
Figure 15:
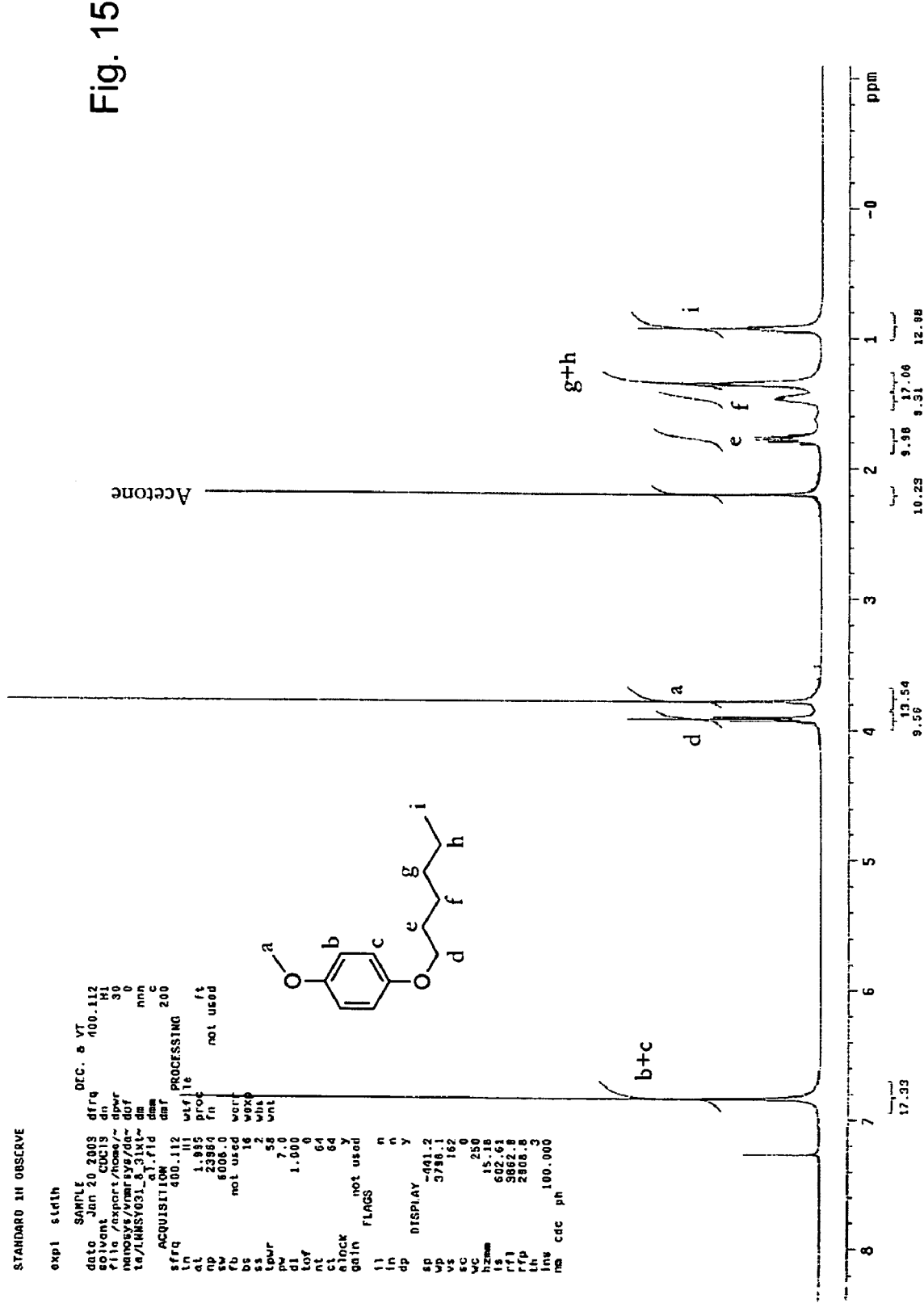
Figure 17:
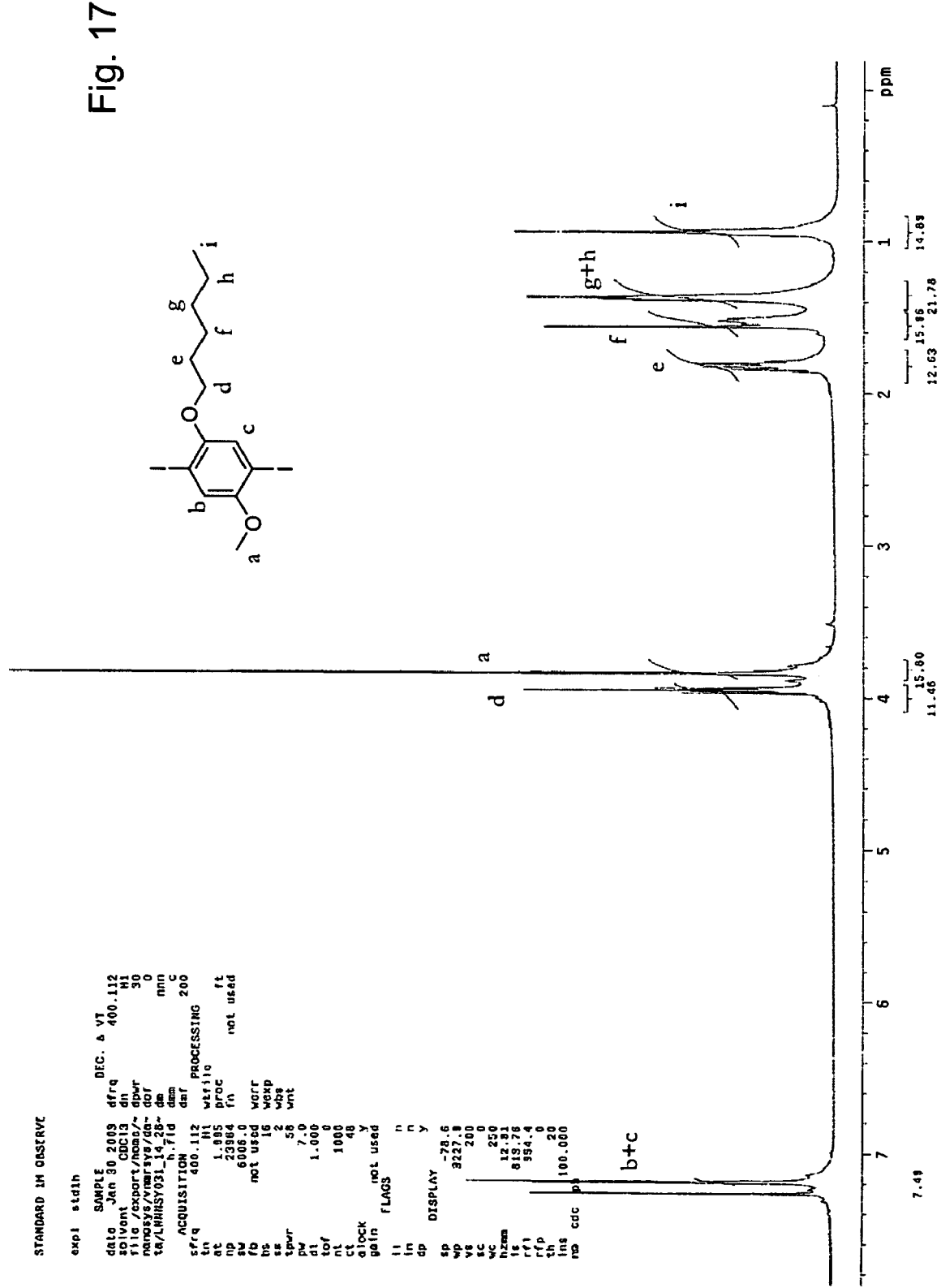

The two sidearm moieties of the conductive composition need not be identical or symmetrical in structure. In another embodiment of the compositions of the present invention, two differing sidearm moieties are employed in the modular synthesis of the conductive composition 21. As shown in FIG. 5, 4-methoxyphenol (compound 17) was alkylated at the unprotected hydroxyl group using 1.1 equivalents of 1-iodohexane (compound 11) in the presence of potassium carbonate and DMF at 70° C., to form intermediate compound 18 (see FIG. 15), which was iodinated (compound 19, FIG. 17), derivatized with thiophene moieties, and coupled to a 1-decyne tail moiety (T1) and a thiophene-phosphonate head group (H3) in a manner similar to Example 2.

Example 4

Synthesis of Tail Group Moiety
1-stannyl-5-decynyl-thiophene

Figure 6:
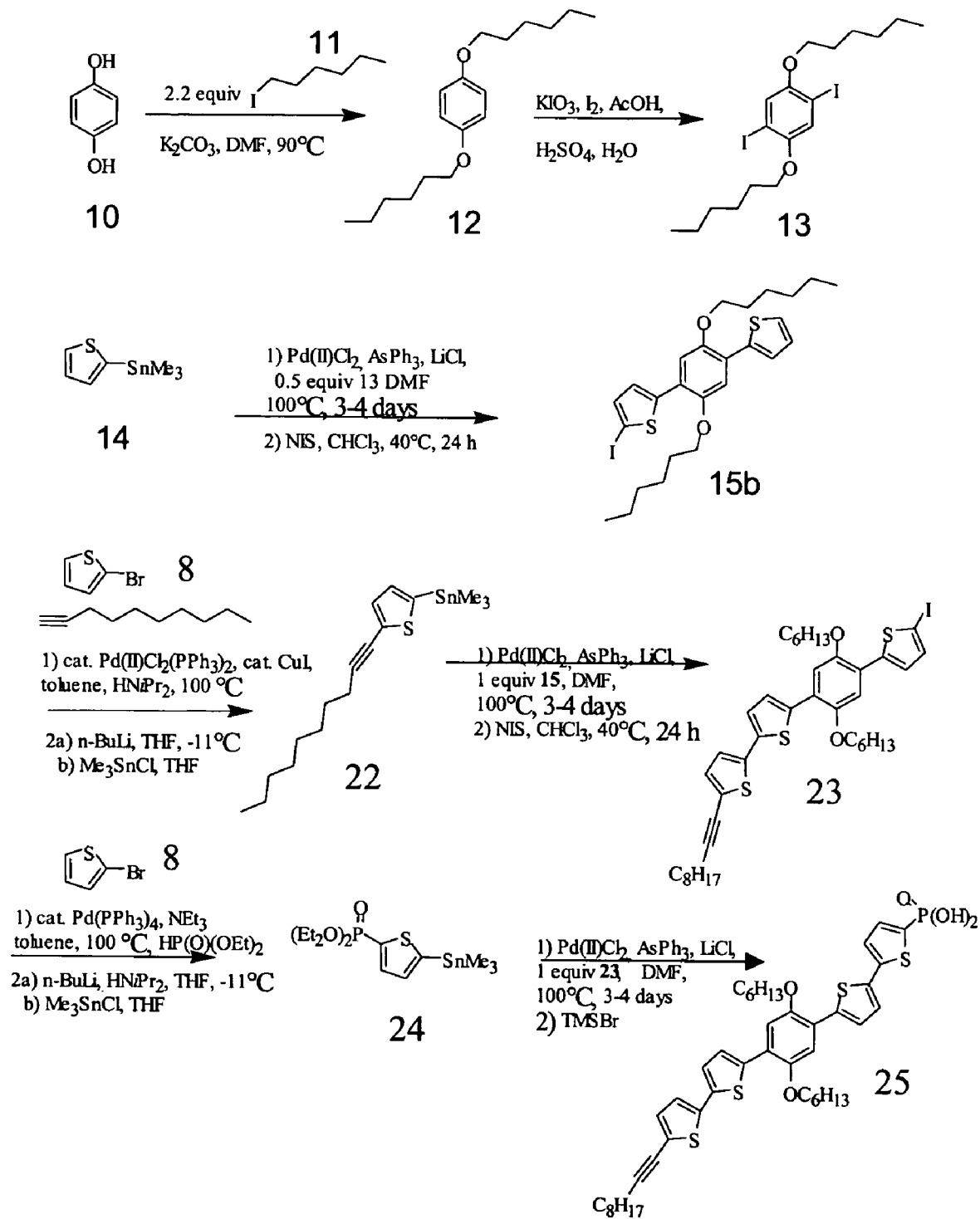
FIG. 6 depicts a chemical synthesis scheme for an additional embodiment of the compositions of the present invention.

Another common intermediate employed in the synthesis of some embodiments of the present invention is the thiophene-containing tail group moiety, 1-stannyl-5-decynyl-thiophene (compound 22), in which a thiophene moiety and tail group are joined prior to coupling to the body structure (in contrast to the synthetic schemes depicted in FIG. 4 and FIG. 5, in which the thiophene moiety is joined to the body structure prior to coupling of the tail group moiety). This thiophene-tail group intermediate can be prepared as follows (FIG. 6). To a 100 mL schlenk tube with resealable Teflon valve and egg-shaped stirbar, palladium dichloride (0.413 mmol, 0.073 g), triphenylphosphine (0.826 mmol, 0.217 g), and copper(I) iodide (0.413 mmol, 0.079 g) were added in the glove box. On the schlenk line, degassed 2-bromothiophene 8 (20.66 mmol, 3.37 g), diisopropyl amine (30 mL), 1-decyne 2 (20.66 mmol, 2.86 g) and toluene (50 mL) were added sequentially via syringe under argon. The reaction vessel was sealed with the valve, the reaction mixture heated to 100° C. and stirred overnight. The reaction mixture was cooled to ambient temperature, and the solvent removed by roto-evaporation. The residue was dissolved in diethyl ether (250 mL) washed with saturated aqueous ammonium chloride (3×125 mL), dried over sodium sulfate, filtered, and the solvent was removed by roto-evaporation, affording a yellow oil. Purification by plugging through silica gel with hexanes afforded 2-decynyl thiophene (compound 22a) as a light yellow oil (4.32 g, 95% yield). $^1$H NMR (CDCl$_3$) δ 7.18 (d, 1 H), 7.12 (d, 2 H), 6.94 (dd, 1H), 2.44 (t, 2 H), 1.70-1.30 (m, 12 H), 0.92 (t, 3 H); GC/MS (M$^+$ 220 m/z). This compound was used without further purification.

To a 1 L schlenk flask with egg-shaped stirbar in a glove box, the 2-decynylthiophene 22a (57.44 mmol, 12.658 g) was added by pipette. On a schlenk line, tetrahydrofuran (300 mL) was cannula transferred to the reaction vessel through a septum. The reaction mixture was cooled to −78° C. and n-butyl lithium (35.9 mL, 1.6 M solution in hexanes), was added dropwise via syringe and the reaction mixture stirred for 45 min. The reaction vessel was fitted with an addition funnel and trimethyltin chloride (57.4 mL, 1.0 M solution in tetrahydrofuran) was cannula transferred to the funnel under positive argon pressure through a septum. The trimethyltin chloride solution was added dropwise to the stirring lithium salt solution over a period of 15 min. at −78° C. The reaction mixture was allowed to warm to ambient temperature with stirring overnight. The solvent was removed in vacuo on the schlenk line and trapped in a 1 L schlenk flask. The resulting residue was dissolved in diethyl ether (500 mL) washed with brine (3×200 mL), dried over magnesium sulfate, filtered and the solvent removed by roto-evaporation to afford 1-stannyl-5-decynyl-thiophene 22b as a light brown oil (20.6 g, 94% yield). $^1$H NMR (CDCl$_3$) δ 7.20 (d, 1 H), 7.00 (d, 2 H), 2.43 (t, 2 H), 1.60 (m, 2 H), 1.44(m, 2H), 1.30 (m, 8H), 0.899 (t, 3 H), 0.37 (s, 9H); GC/MS (M$^+$) 384 m/z, (M$^+$—CH$_3$) 369 m/z.

Example 5

Synthesis of Conjugated Composition 25

Another example of a conjugated composition of the present invention is compound 25 shown in Table 1 and FIG. 6. This composition was prepared using the thiophene-derivatized tail group moiety 22b and body structure 15b as follows.

To a 50 mL schlenk tube with a stirbar, palladium dichloride (0.12 mmol, 0.021 g), triphenylarsene (0.24 mmol, 0.073 g), LiCl (2.4 mmol, 0.103 g) and 1-stannyl-5-decynyl-thiophene 22b, were added in a glove box. On a schlenk line, compound 15b was dissolved in degassed dimethylformamide and cannula transferred to the schlenk tube under positive argon pressure. The reaction mixture was placed under vacuum, backfilled with argon, the vessel sealed and heated to 100° C. for up to 4 days. The reaction mixture was diluted with ethyl acetate (250 mL) and washed with de-ionized water (100 mL), the organic layer separated and solvent removed in vacuo. Purification by silica flash chromatography (4% ethyl acetate:96% hexane) afforded a precursor to compound 23 (precursor structure not shown) as a yellow oily solid (0.360 g, 23% yield). $^1$H NMR (CDCl$_3$) δ 7.54 (m, 1 H), 7.35 (d, 1 H), 7.25-7.16 (m, 4H), 7.09 (dd, 1 H), 4.09 (m, 4H), 1.93 (m, 4 H), 1.56 (m, 4H), 1.39 (m, 8H), 0.94 (m, 9H); MALDI TOF MS (M+H) 661 m/z.

To a 50 mL schlenk flask with Teflon valve, stirbar and the precursor to compound 23 (0.515 mmol 0.340 g) and chloroform (6.2 mL), N-iodosuccinimide (0.515 mmol, 0.116 g) was added in one portion under argon. The reaction vessel was sealed and the mixture heated to 40° C. for 22 h. The reaction mixture was diluted with ethyl acetate (100 mL) washed with 10% aqueous sodium thiosulfate (3×25 mL), brine (2×25 mL), dried over magnesium sulfate, filtered and plugged through silica gel with ethyl acetate. Solvent removal by roto-evaporation afforded the crude product 23 as a sticky yellow solid which was used without further purification (0.402 g, 99%). $^1$H NMR (CDCl$_3$) δ 7.72 (d, 1 H), 7.56 (m, 1 H), 7.50 (d, 1H), 7.40-7.32 (m, 2H), 7.30-7.20 (m, 2H), 7.11 (dd, 1 H), 5.18 (t, 2H), 4.13 (m, 4H), 2.15 (m, 2H), 1.95 (m, 4H), 1.58 (m, 8H), 1.50-1.20 (m, 14H), 1.28 0.93 (m, 9 H).

In this particular embodiment of the invention, a thiophene-coupled head group moiety 24 was prepared for attachment to the body structure, via coupling to the non-iodinated thiophene of compound 15b. Addition of the precursor head group moiety 24 to the crude reaction product 23 to form conductive composition 25 was performed as provided in FIG. 6.

Example 6

Synthesis of Conjugated Composition 28

Figure 7:
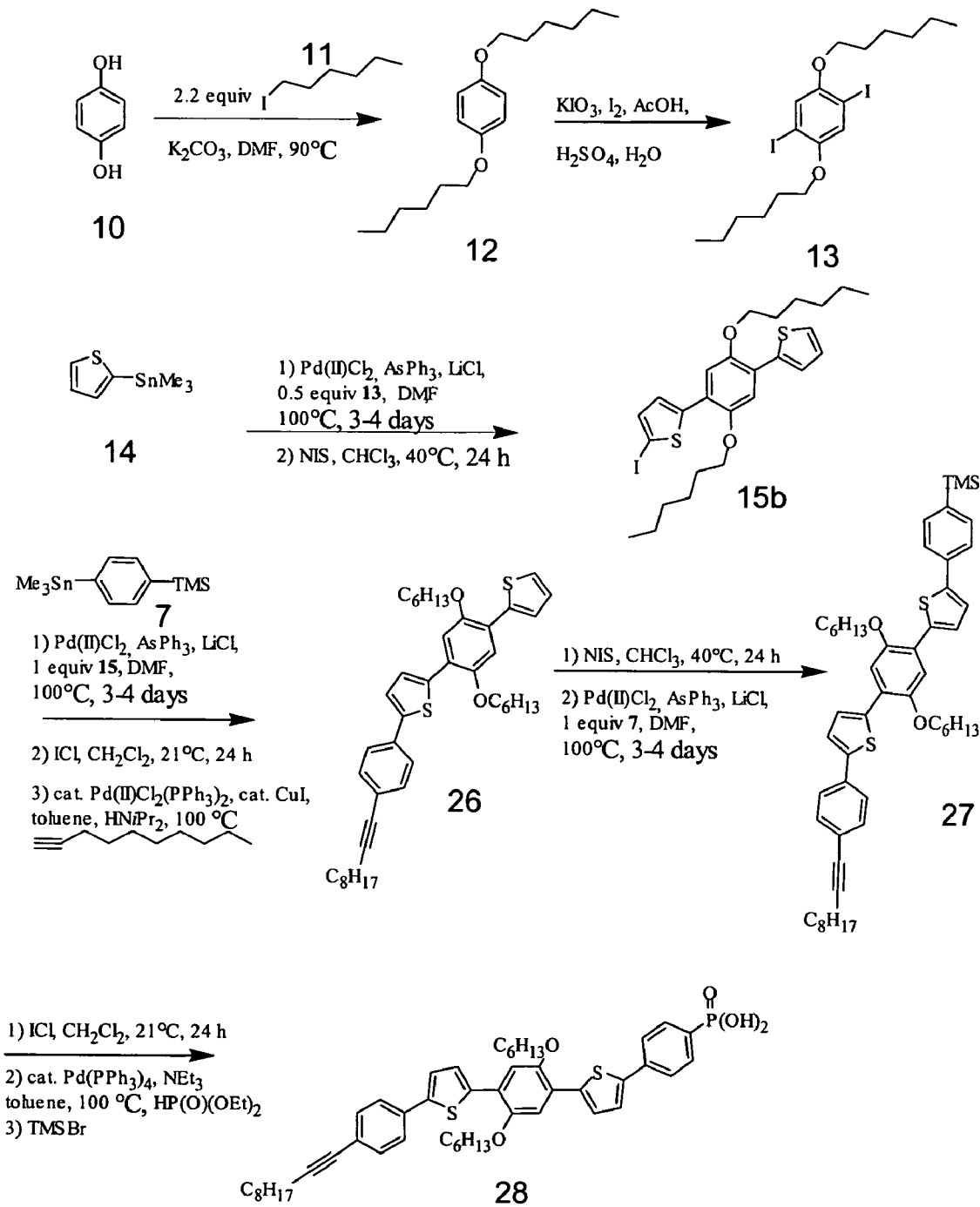
FIG. 7 depicts a chemical synthesis scheme for a further embodiment of the compositions of the present invention.
Figure 10:
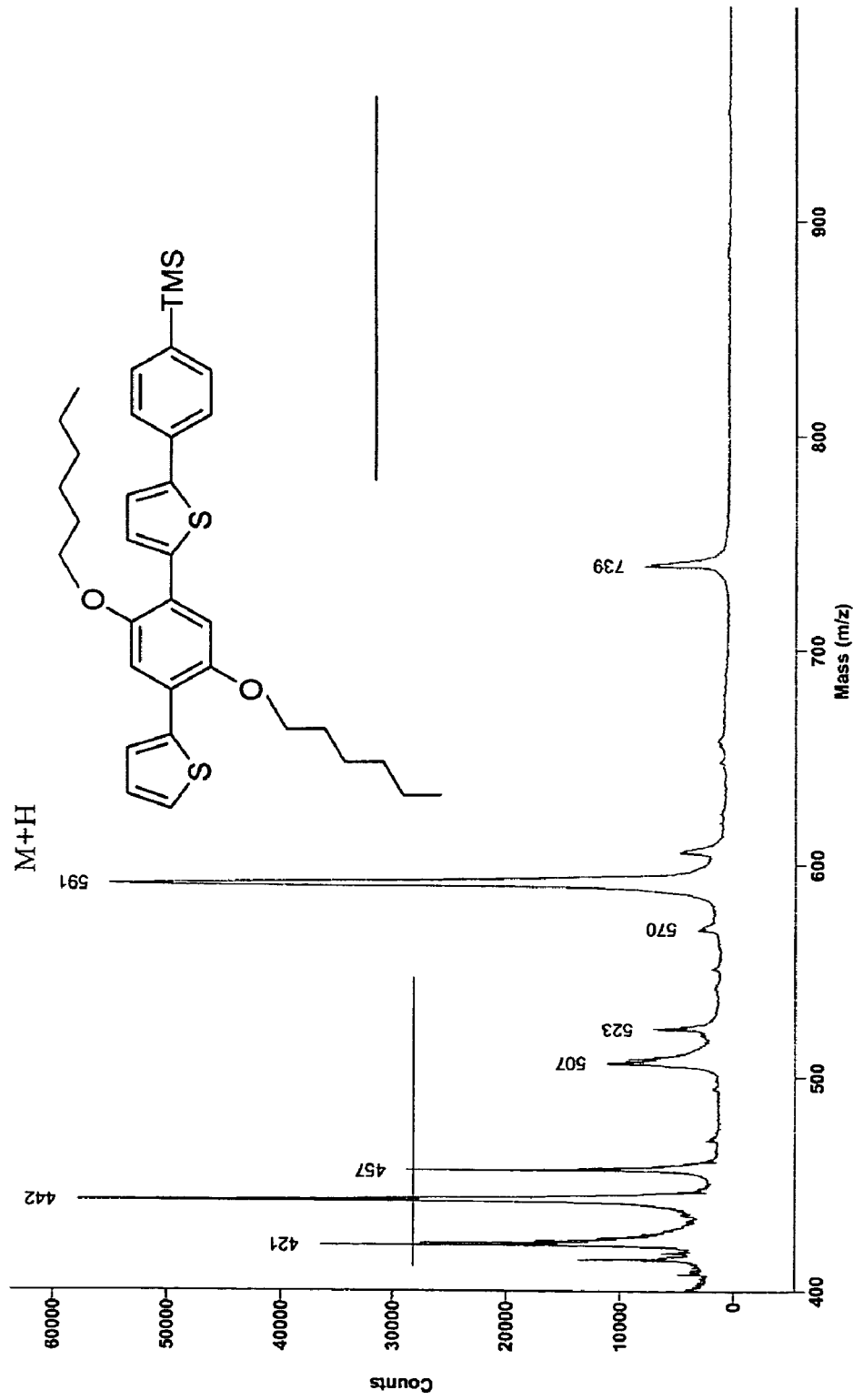

A further example of a conjugated composition of the present invention is compound 28 as shown in Table 1 and FIG. 7. This composition was prepared using the thiophene-containing body structure 15b and a benzyl-containing tail moiety in a similar manner as described in FIG. 7. Alternatively, compound 28 could have been synthesized using the intermediate depicted in FIG. 10 (i.e., by using a body structure having the benzyl ring instead of a head group having the benzyl ring).

Figure 11:
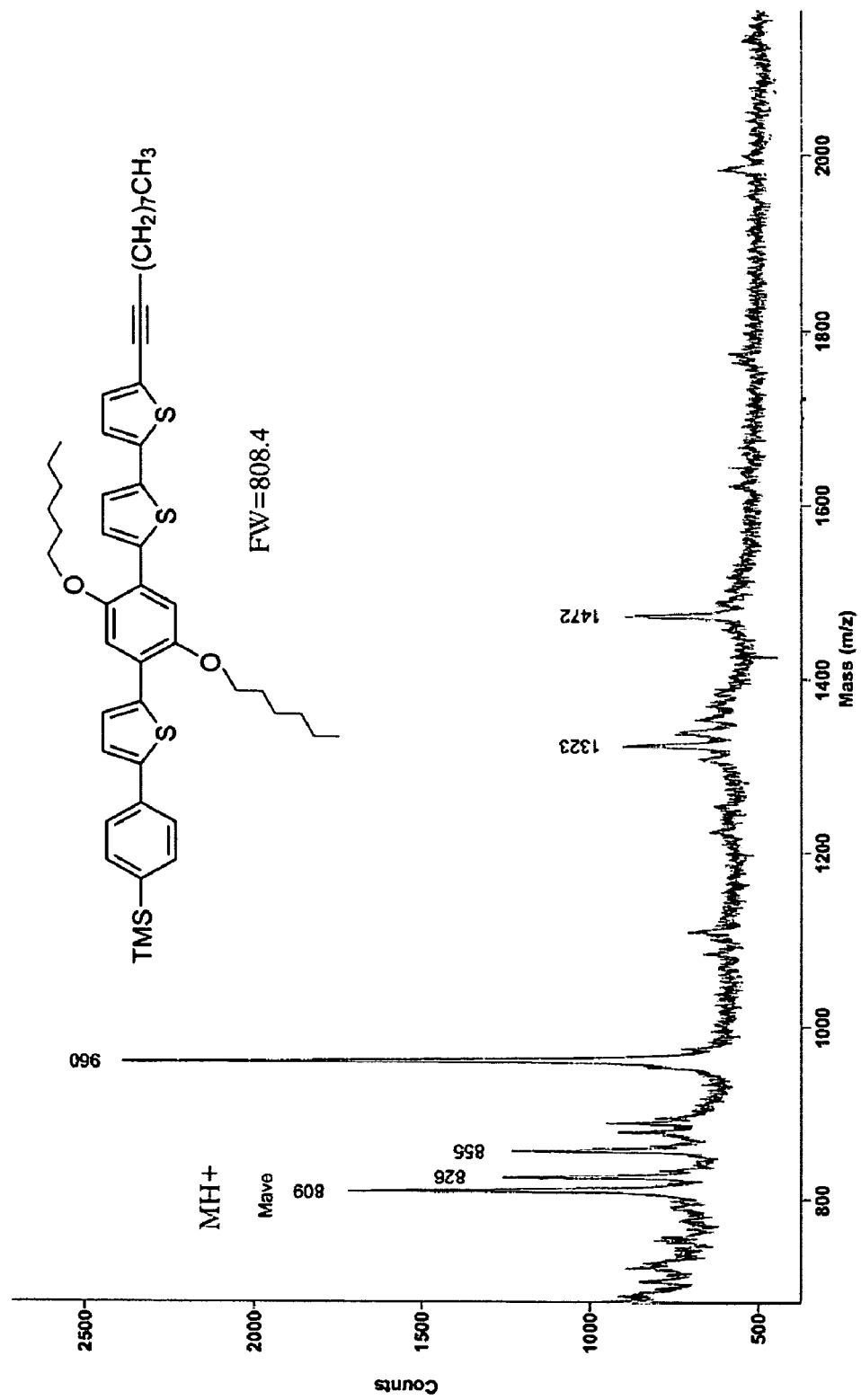
Figure 12:
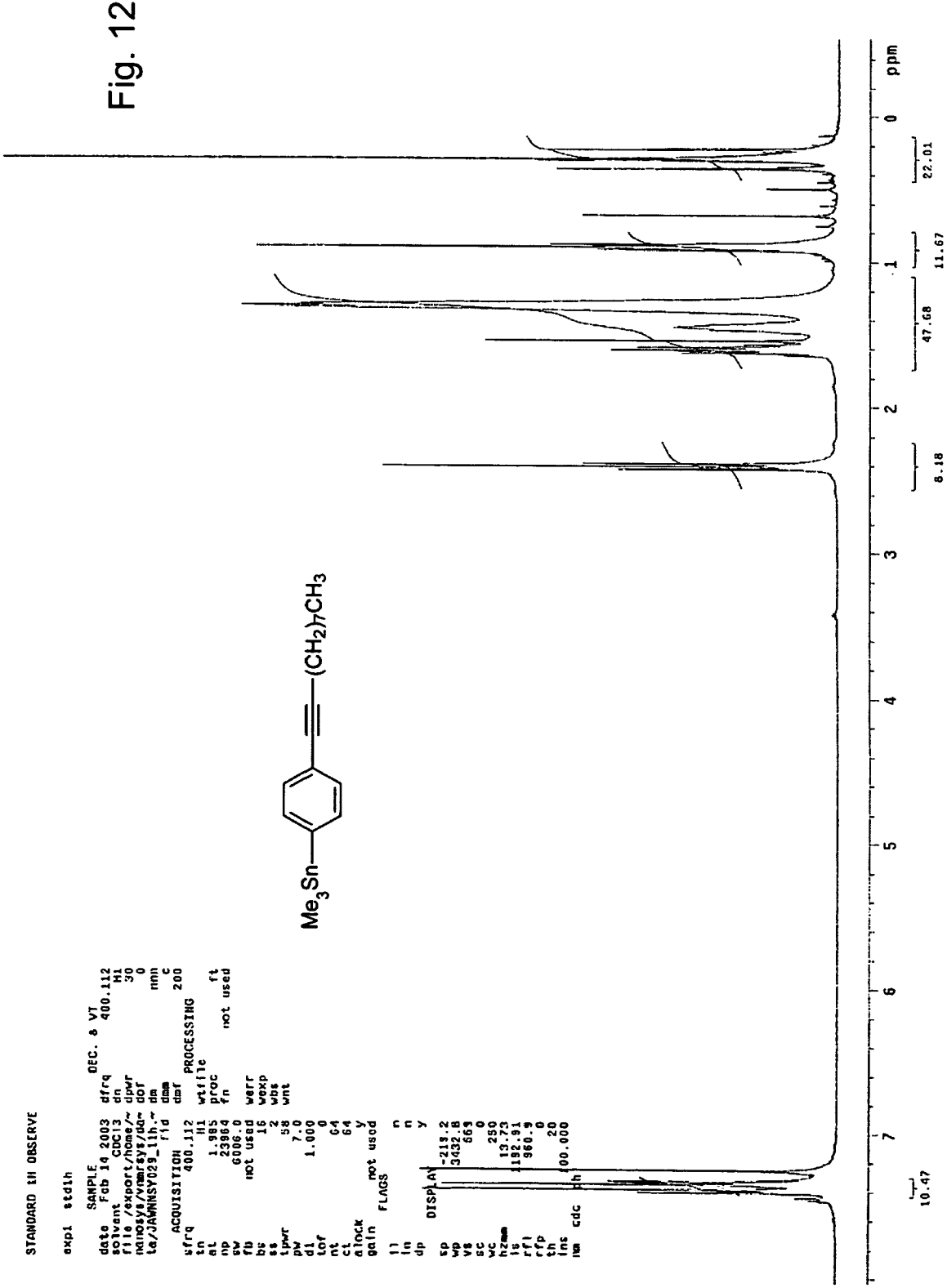

The conductive composition depicted in FIG. 11 could be synthesized in a similar modular manner, using body structure 15b, a benzylated head group (such as shown in FIG. 9, and a thiophene-containing tail group (e.g., compound 22).

Example 7

An Alternate Method for Modular Synthesis of Compound 25

Figure 20:
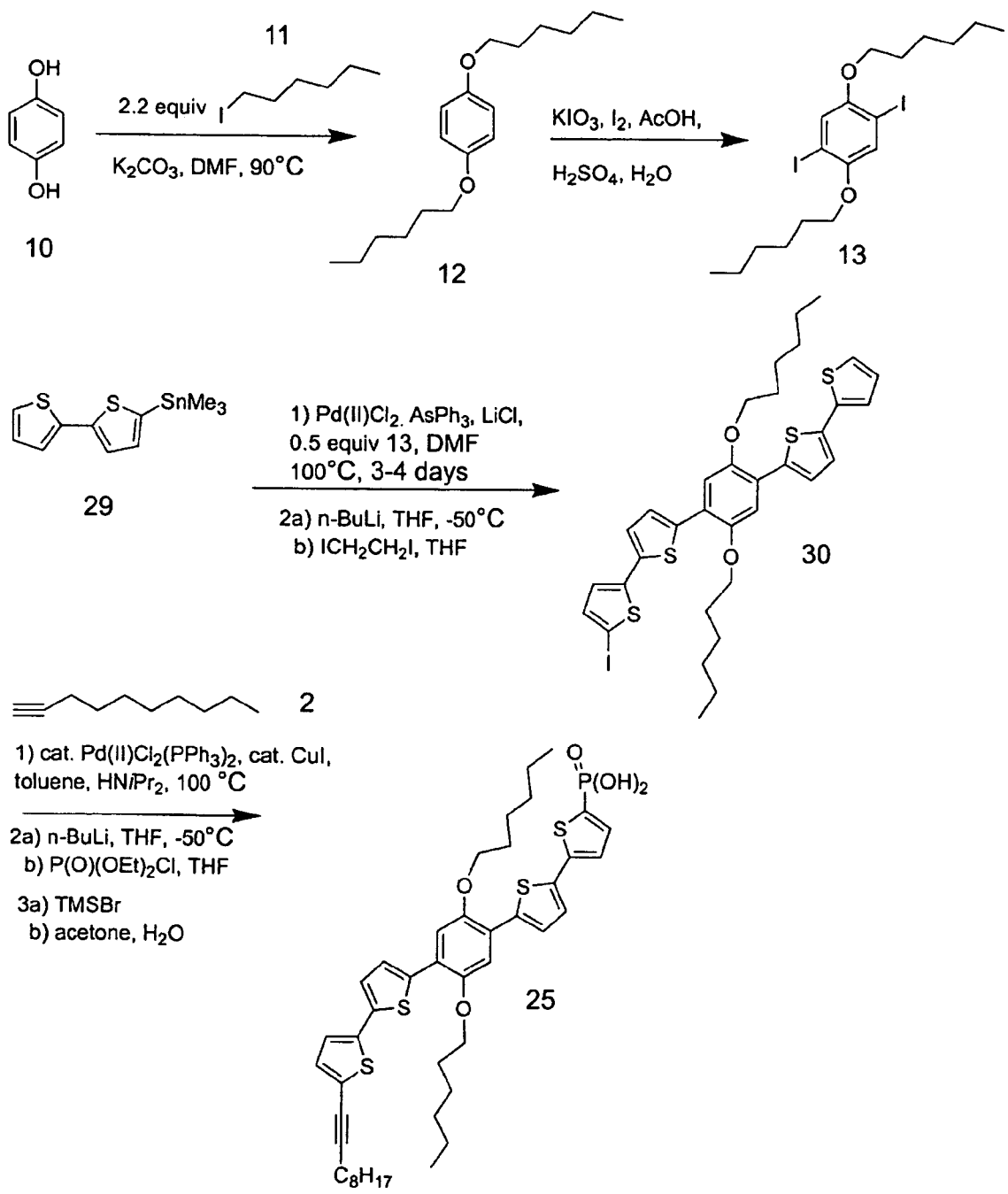
FIGS. 20 through 28 depict additional chemical synthesis schemes for additional embodiments of the present invention.

An alternate modular approach to preparation of conductive composition 25 is also contemplated, as depicted in FIG. 20. In this approach, dithiophene elements are attached as a unit to the body structure, rather than using thiophene-containing head and tail group components. In this synthetic approach, iodinated body structure 13 is prepared from hydroquinone 10 as described above. The iodine moieties are then replaced with two dithiophene structures to form compound 30. Intermediate 30 is then joined to tail group 2 and a phosphonic acid head group, as shown in FIG. 20, to form conductive composition 25.

Example 8

Synthesis of Conjugated Composition 31

Figure 21:
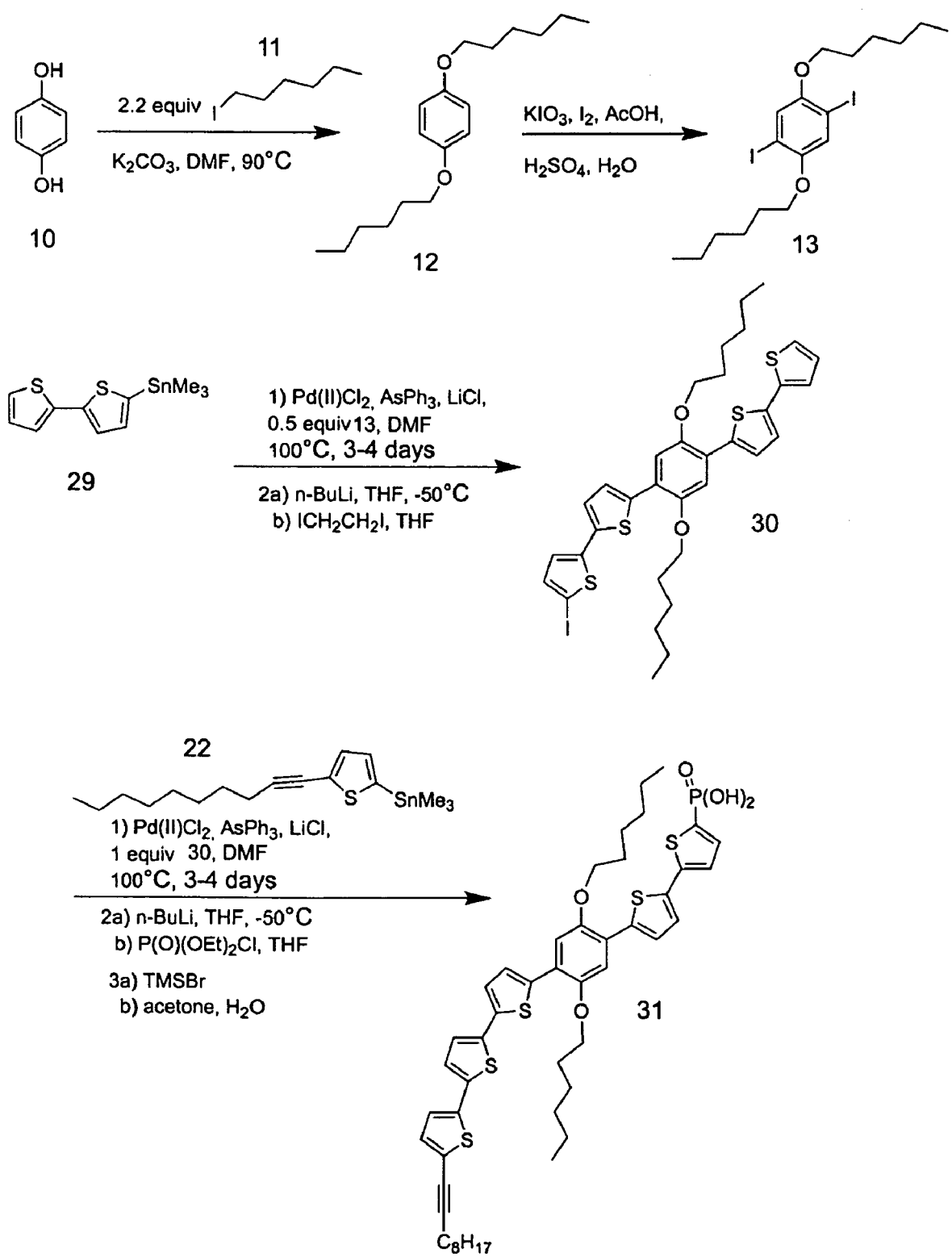

Di-iodinated intermediate 13 can also be used in the synthesis of an additional embodiment of the conductive compositions of the present invention, compound 31, as described in FIG. 21.

Example 9

Synthesis of Polymerizable Conductive Polymers

Embodiments of the present invention are contemplated in which one or more components of the conductive composition (e.g., body structure, head, tail) are present in multiple units. For example, some embodiments include body structures prepared by coupling or polymerizing two or more body structures. The coupling can be performed either prior to or after attachment of the head and tail moieties to the respective body structure members. These embodiments are generically described as conductive compositions having the structure $[H_x-B_y-T_z]_n$, wherein H comprises at least one functionalized head group capable of binding to a nanocrystal surface (or, for nanostructure-bound embodiments, at least one head group bound to a nanocrystal surface); wherein B comprises a body structure comprising one or more conjugated organic moieties, wherein a first conjugated organic moiety is coupled to a proximal functionalized head group or bound head group; wherein T comprises at least one tail group coupled to the body structure; and wherein x, y, z and n independently comprise integers equal to or greater than 1.

Figure 22:
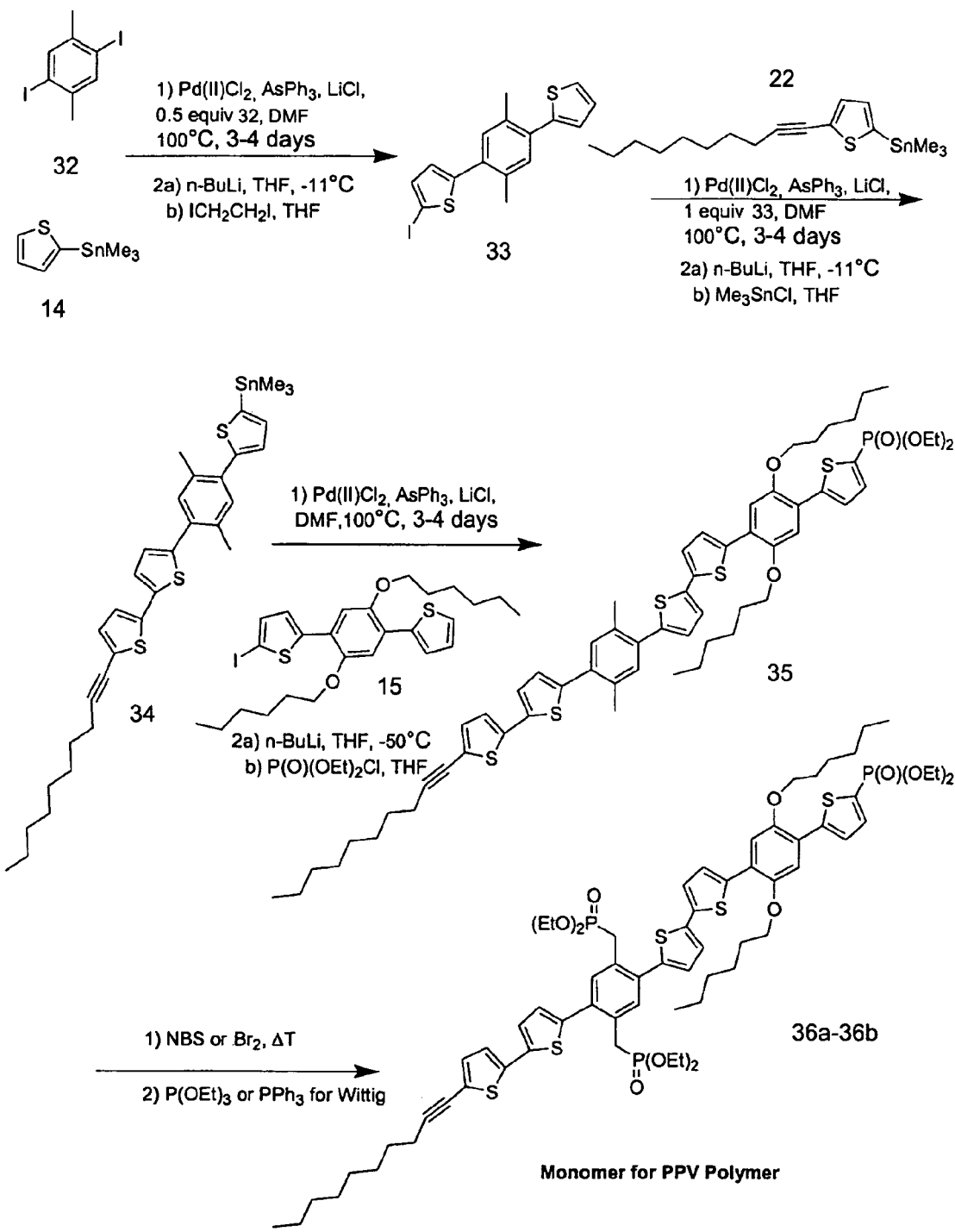

FIG. 22 provides a synthetic scheme for preparation of a conductive composition (compound 36) incorporating two core body structure components, a p-xylene unit (derived from compound 32) and an O-alkylated hydroxyquinone unit (compound 12). It should be noted, however, that although two body structure components are employed from a synthesis perspective, the final product (in this example, compound 36) can also be considered to have one large body component having two aromatic rings coupled by a dithiophene moiety, and having a tail moiety attached to a first end of the overall body structure and a head moiety attached to a second end of the overall body structure. As with many embodiments of the chemical compositions of the present invention, the distinction between body structure, head group and tail group elements is partially based upon the synthetic approach chosen (note the two modular approaches to compound 25 as described above), and as such should not be considered limiting.

Figure 23:
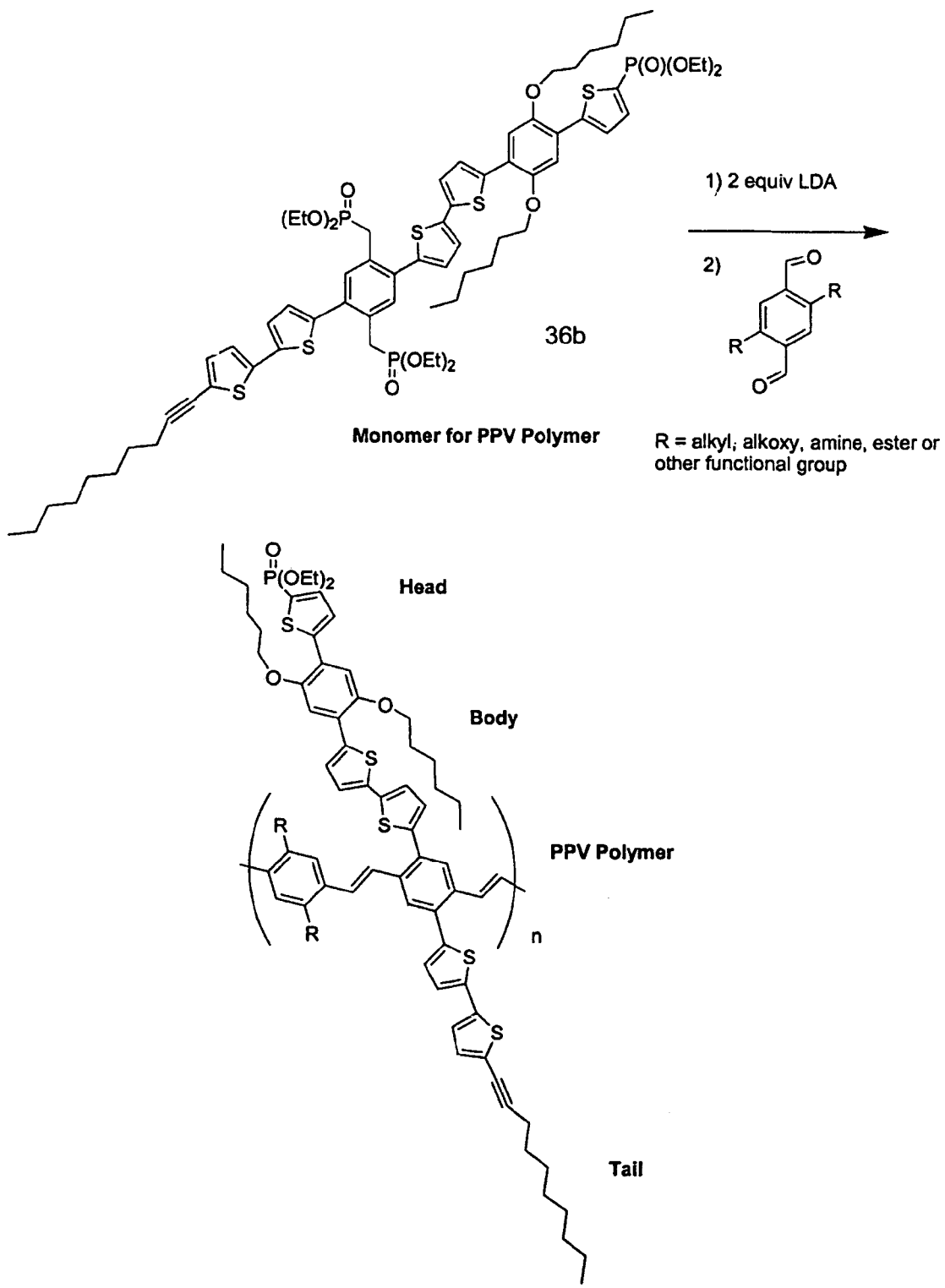
Figure 24:
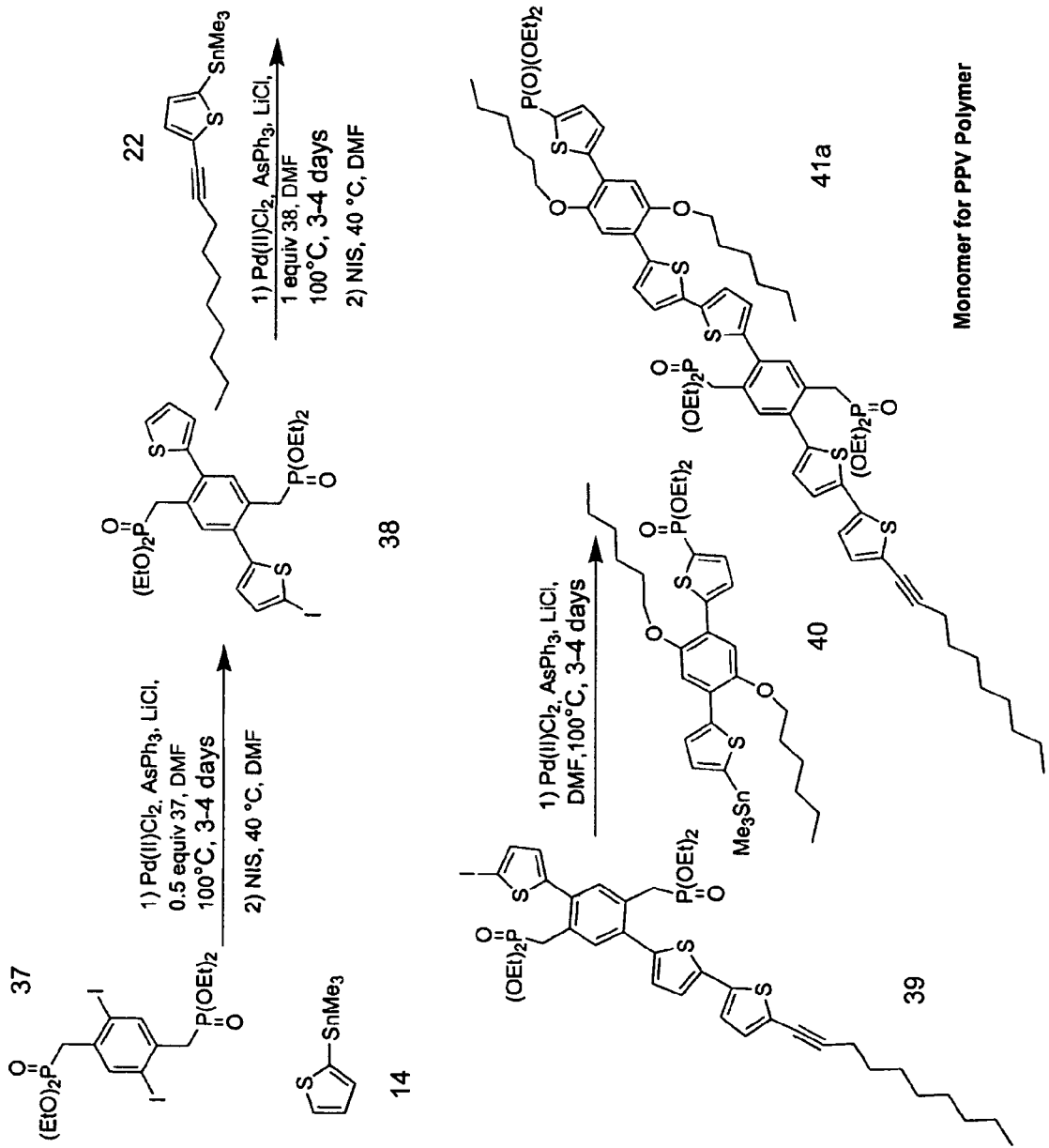

Compound 36 can be synthesized as provided in FIG. 23. In a similar manner, compound 41 can also by synthesized as shown in FIG. 24. In this modular approach, the first portion of the body structure (compound 38) is prepared and then coupled to the tail group 22 (to form intermediate 39); a second body structure portion (compound 20) is stannylated and coupled to a head group (to form intermediate 40), and then these synthetic intermediates are joined to form compound 41.

Compounds 36 and 41 are of particular interest, since these compositions also embody an additional optional feature of the present invention, one of the polymerization aspects of the conductive composition. As shown in FIG. 23, the sidearm elements of the p-xylene derived portion of the body structure can be reacted with a ketone functional group as shown in FIG. 23, for example, in the presence of a stereoselective base, such as lithium diisopropyl amide (LDA). The cross-reactivity between the ketone-containing conductive compositions (preferably on different nanostructures) leads to crosslinking of the adjacent conductive compositions.

This embodiment is particularly of interest in nanostructure-matrix compositions having both n-type and p-type nanocrystals incorporated into the matrix. Coupling of an n-type nanocrystal to an adjacent p-type nanocrystal will allow for an even more efficient transmission of electrons and holes within the matrix.

Example 10

Synthesis of Conductive Composition 43

Figure 25:
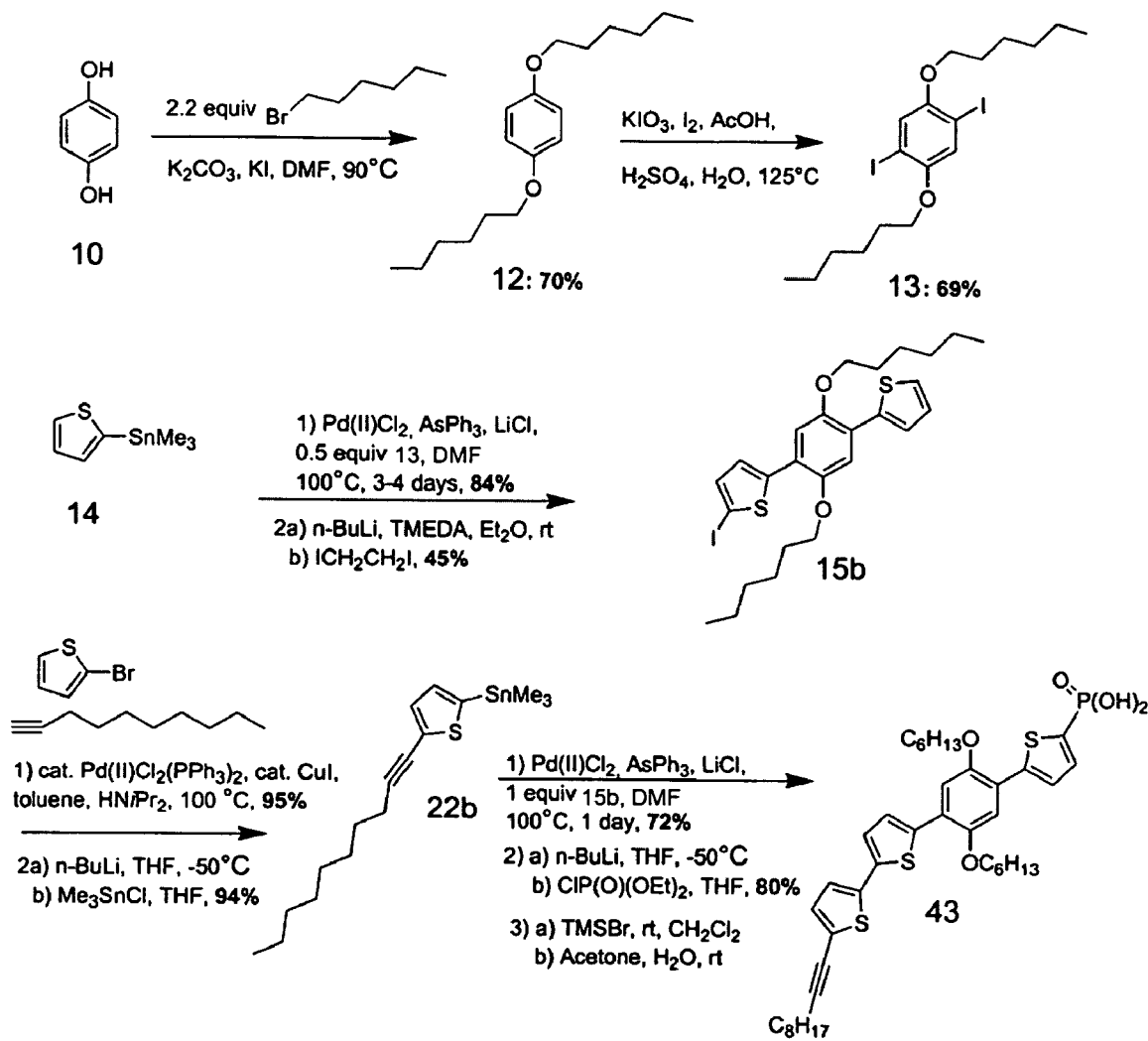

Di-iodinated intermediate 13 can also be used in the synthesis of an additional embodiment of the conductive compositions of the present invention, compound 43 (see FIG. 25). For the synthesis of this compound, intermediate 30 is prepared as described above. The head group and tail group moieties are then coupled to the body structure using the protocols described in FIG. 25, to generate compound 43.

Example 11

Synthesis of Conductive Composition 46

Figure 26:
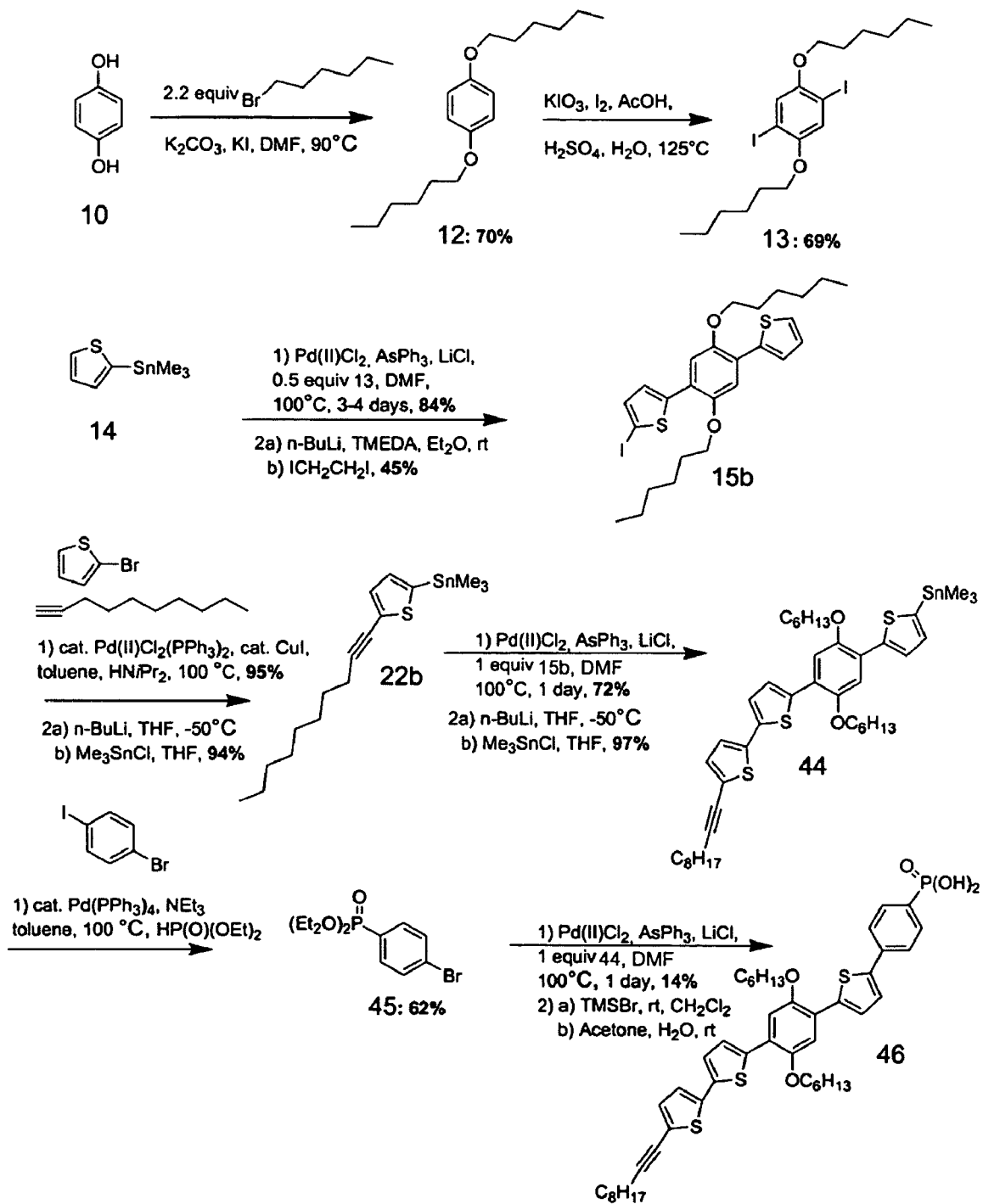

Di-iodinated intermediate 13 can also be used in the synthesis of an additional embodiment of the conductive compositions of the present invention, compound 46 (see FIG. 26).

To a 50 mL schlenk flask with egg-shaped stirbar in a glove box, precursor 22b (0.997 mmol, 0.659 g) was added. The vessel was stoppered, placed under vacuo and backfilled with argon (3×). On a schlenk line, tetrahydrofuran (5 mL) was cannula transferred to the reaction vessel through a septum. The reaction mixture was cooled to −78° C. and n-butyl lithium (0.623 mL, 1.6 M solution in hexanes,) was added dropwise via syringe and the reaction mixture warmed to −50° C. and stirred for 1 h. The reaction mixture was recooled to −78° C. and trimethyltin chloride (0.997 mL, 1.0 M solution in tetrahydrofuran) was added dropwise via syringe to the stirring lithium salt solution at −78° C. The reaction mixture was allowed to warm to ambient temperature with stirring overnight. The solvent was removed in vacuo on the schlenk line and trapped in a 1 L schlenk flask. The resulting residue was extracted with hexanes (3×50 mL) and cannula filtered followed by in vacuo solvent removal to afford intermediate compound 44 as a yellow oil. $^1$H NMR (CDCl$_3$) δ 7.67 (d, 1 H), 7.45 (d, 1 H), 7.28-7.22 (m, 2 H) 7.20 (d, 1H) 7.15 (d, 1H), 7.03 (s, 2H), 4.12 (m, 4H), 2.46 (t, 2 H), 1.93 (m, 4H), 1.62 (m, 2 H), 1.44 (m, 2H), 1.39 (m, 8H), 0.95 (m, 9 H), 0.37 (s, 9H).

To prepare functionalized head moiety 45, compound 13 (50.0 mmol, 14.15 g) and palladium(0)tetrakis[triphenylphosphine] (2.50 mmol, 2.89 g) were added to a 200 mL schlenk tube with a Teflon valve and stirbar. On a schlenk line, degassed triethyl amine (20.9 mL) and degassed toluene (50 mL) were then sequentially added via syringe under argon. Next, degassed diethyl phosphite (50.0 mmol, 6.91 g) was added via syringe under argon. The reaction vessel was sealed, the mixture stirred at ambient temperature for 12 h followed by heating to 50° C. for 1 h. The solvent was removed by roto-evaporation, and the residue dissolved in ethyl acetate (500 mL) and washed with saturated aqueous ammonium chloride (3×200 mL), dried over magnesium sulfate, filtered and the solvent removed by roto-evaporation. Isolation by silica gel chromatography (1:1 Ethyl Acetate: Hexanes) afforded scheme 2.3 compound 8 as a colorless oil (9.17 g, 62% yield) $^1$H NMR (CDCl$_3$) δ 7.90-7.50 (m, 4 H), 4.30-4.10 (m, 4 H) 1.50-1.30 (m, 6H); {1H}$^{31}$P NMR (CDCl$_3$) δ 18.8 (s).

To a 50 mL schlenk tube with a stirbar, palladium dichloride (0.06 mmol, 0.010 g), triphenylarsene (0.10 mmol, 0.031 g), LiCl (1.0 mmol, 0.043 g) and scheme 2.3 compound 8 (1.05 mmol, 0.370 g), were added in a glove box. On a schlenk line, scheme 2.3 compound 7 was dissolved in degassed dimethylformamide (6 mL) and cannula transferred to the schlenk tube under positive argon pressure. The reaction mixture was placed under vacuum, backfilled with argon, the vessel sealed and heated to 100° C. for 12 h. The reaction mixture was diluted with ethyl acetate (250 mL) and washed with de-ionized water (100 mL), the organic layer separated and solvent removed in vacuo. Purification by silica flash chromatography (ethyl acetate:hexane 1:1) afforded Scheme 2.3 compound 9 as a yellow oily solid (0.124 g, 14% yield). $^1$H NMR (CDCl$_3$) δ 7.85-7.80 (m, 2 H) 7.76-7.72 (m, 2H) 7.65 (d, 1 H), 7.46 (d, 1 H), 7.42 (d, 2 H) 7.25 (m, 2H) 7.15 (d, 1H), 7.04 (s, 1H), 7.03 (s, 1H) 4.15 (m, 4H), 2.46 (t, 2 H), 1.97 (m, 4H), 1.62 (m, 2 H), 1.42 (m, 2H), 1.37 (m, 8H), 0.95 (m, 9 H); {1H}$^{31}$P NMR (CDCl$_3$) δ 19.6 (s).

Example 12

Synthesis of Conductive Composition 50

Figure 27:
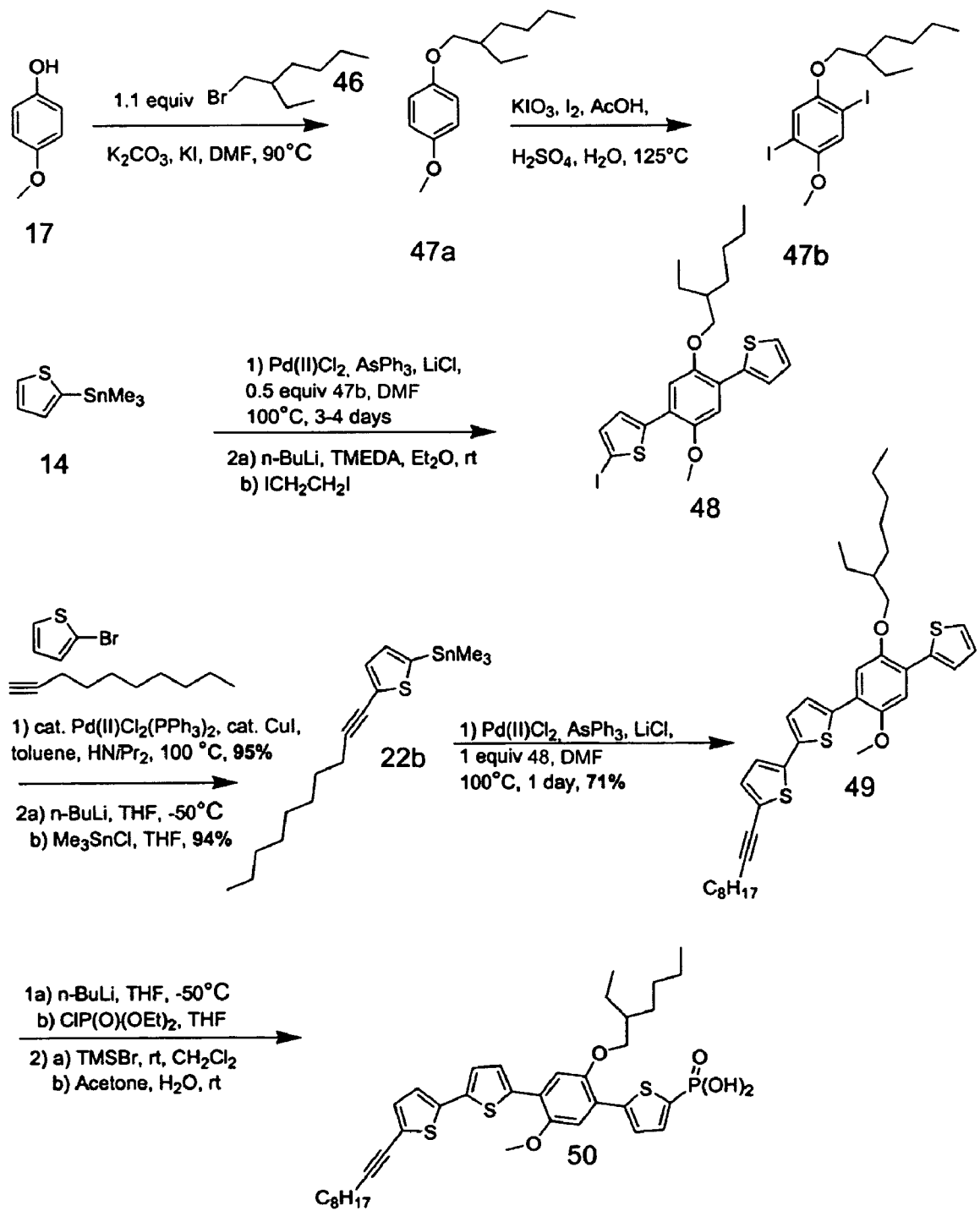

Compound 50 is prepared using iodinated body structure 48, as shown in FIG. 27. To a 250 mL schlenk tube with stirbar and Teflon valve, palladium dichloride (2.05 mmol, 0.363 g), triphenylarsene (4.1 mmol, 1.255 g), and LiCl (41 mmol, 1.759 g) were added in a glove box. On a schlenk line, 1,4-diiodo-2-(2-ethylhexoxy)-5-methoxybenzene (compound 47b, 20.5 mmol, 10.0 g), was added and the vessel placed under vacuum and backfilled with argon (3x). Next, degassed dimethylformamide (DMF, 100 mL) was cannula transferred under positive argon pressure. The vessel was sealed and heated to 100° C. for 1 day. The reaction mixture was cooled and diluted with ethyl acetate (500 mL) and washed with saturated aqueous sodium thiosulfate (3x150 mL) and brine (3x150 mL). The organic layer was separated, dried over sodium sulfate, filtered and the solvent removed by roto-evaporation. Purification by flash chromatography (Ethyl acetate:hexanes, 0, 1, 2, 5 and 10% gradient) and solvent removal by roto-evaporation afforded of 1,4-dithiophene-2-(2-ethylhexoxy)-5-methoxybenzene (7.55 g, 92% yield) as a colorless oil. $^1$H NMR (CDCl$_3$) δ 7.56 (m, 2 H), 7.37 (d, 2 H), 7.29 (s, 1H), 7.26 (s, 1H), 7.13 (m, 2 H), 4.01 (d, 2H), 3.97 (s, 3H), 1.87 (m, 1 H), 1.61 (m, 4H), 1.38 (m, 8H), 1.00 (t, 3 H), 0.98 (t, 3H).

To a 500 mL schlenk flask with egg-shaped stirbar in a glove box, the reaction product (16.85 mmol, 6.75 g) was added. The vessel was stoppered, placed under vacuo and backfilled with argon (3x). On a schlenk line, tetrahydrofuran (241 mL) was cannula transferred to the reaction vessel through a septum. Next N,N-Tetramethyl ethylenediamine (16.85 mmol, 1.96 g) was transferred to the reaction mixture via syringe. The reaction mixture was cooled to −78° C. and n-butyl lithium (10.53 mL, 1.6 M solution in hexanes,) was added dropwise via syringe and the reaction mixture was stirred for 1 h. A THF solution (70 mL) of 1,2-diiodoethane (21.91 mmol, 6.174 g) was cannula transferred to the stirring lithium salt solution at −78° C. The reaction mixture was allowed to warm to ambient temperature with stirring overnight. The solvent was removed by roto-evaporation and the residue dissolved in ethyl acetate (225 mL) and washed with 10% sodium thiosulfate (1x150 mL) and brine (200 mL). The organic layer was separated, dried over magnesium sulfate, filtered and the solvent removed by roto-evaporation. Purification by flash chromatography (Ethyl acetate:hexanes, 0, 1, 2, 5 and 10% gradient) and solvent removal by roto-evaporation afforded 4-iodo-(1,4-dithiophene-2-(2-ethylhexoxy)-5-methoxybenzene (compound 48, 6.21 g, 70% yield) as a yellow oil. $^1$H NMR (CDCl3) δ 7.55 (m, 1 H), 7.38 (d, 1 H), 7.29 (s, 1H), 7.25 (d, 1H), 7.21 (d, 1H), 7.20 (s, 1H), 7.13 (dd, 1 H), 4.01 (d, 2H), 3.99 (s, 3H), 1.88 (m, 1 H), 1.61 (m, 4H), 1.36 (m, 8H), 1.01 (t, 3 H), 0.98 (t, 3H).

The iodinated body structure 48 is then coupled to the tail moiety to form intermediate compound 49 (as described in FIG. 27). To a 100 mL schlenk tube with a stirbar, palladium dichloride (0.32 mmol, 0.057 g), triphenylarsene (0.64 mmol, 0.197 g), LiCl (6.43 mmol, 0.277 g) and 1-stannyl-5-decynyl-thiophene 22b, were added in a glove box. On a schlenk line, compound 48 was dissolved in degassed dimethylformamide and cannula transferred to the schlenk tube under positive argon pressure. The reaction mixture was placed under vacuum, backfilled with argon, the vessel sealed and heated to 100° C. for up to 1 day. The reaction mixture was diluted with ethyl acetate (250 mL) and washed with de-ionized water (100 mL), the organic layer separated and solvent removed in vacuo. Purification by silica flash chromatography (5-15% ethyl acetate:95-85% hexane) afforded the precursor compound as a yellow oil (2.83 g, 71% yield). $^1$H NMR (CDCl$_3$) δ 7.57 (d, 1 H), 7.47 (m, 1 H), 7.38 (m, 1H), 7.32-7.25 (m, 2 H), 7.17 (d, 1H), 7.13 (dd, 1H) 7.09-7.00 (m, 2H), 4.00 (m, 2H), 3.99 (s, 3H), 2.47 (t, 2H) 1.87 (m, 1H), 1.63 (m, 4H), 1.45 (m, 2H), 1.36 (m, 8H), 1.30-0.94 (m, 9H)); MALDI TOF MS (M+H) 618 m/z.

To a 100 mL schlenk flask with egg-shaped stirbar in a glove box, precursor 49 (4.56 mmol, 2.82 g) was added. The vessel was stoppered, placed under vacuo and backfilled with argon (3x). In a drybox, tetrahydrofuran (23.3 mL) was pipetted to the reaction vessel and the substrate dissolved at ambient temperature. The reaction mixture was cooled to −78° C. and n-butyl lithium (2.85 mL, 1.6 M solution in hexanes,) was added dropwise via syringe and the reaction mixture warmed to −50° C. and stirred for 1 h. The reaction mixture was recooled to −78° C. and diethylphosphonate chloride (0.4.56 mmol, 0.658 mL) was added dropwise via syringe to the stirring lithium salt solution at −78° C. The reaction mixture was allowed to warm to ambient temperature with stirring overnight. The solvent was removed by roto-evaporation and the resulting residue was dissolved in ethyl acetate (150 mL), dried over sodium sulfate, filtered. Purification by silica flash chromatography (5-15% ethyl acetate:95-85% hexane) afforded the precursor compound as an orange oil.

Example 13

Synthesis of Conductive Composition 25

Figure 28:
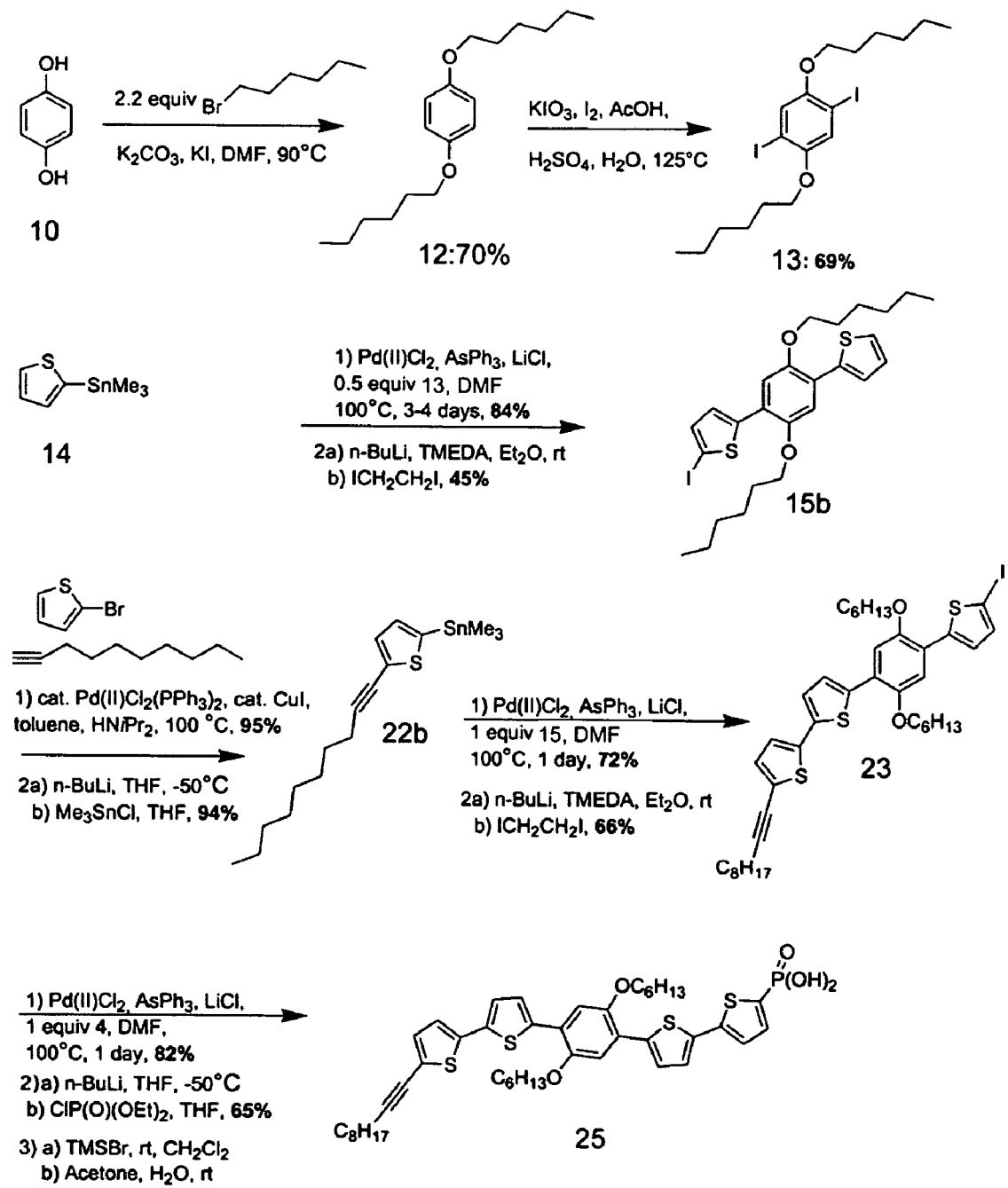

FIG. 28 provides an alternate approach to the synthesis of conductive composition 25.

Example 14

Preparation of Nanostructures

Excess organic surfactants such as trioctyl phosphine (TOP), trioctyl phosphine oxide (TOPO), hexadecyl phosphonic acid (HDPA), octadecyl phosphonic acid (ODPA), and tri-n-butyl phosphine (TBP) are commonly present in nanostructure preparations as prepared by standard techniques cited herein. Optionally, any excess organic surfactant is removed from the nanostructure preparation prior to association with the conductive compositions of the present invention. This can be achieved, for example, by adding a solvent mixture prepared from a first solvent in which a nanostructure is soluble (e.g., toluene or chloroform) and a second solvent in which the nanostructure is not soluble (e.g., isopropanol or longer chain alcohol, or an acetate such as ethyl acetate). While the ratio of first solvent to second solvent as prepared in the solvent mixture typically ranges between 1:1 and 10:1, one preferred solvent mixture is 4 parts toluene to one part isopropanol.

An additional quantity of the second solvent is then added in a quantity sufficient to precipitate the nanostructures (but not the excess surfactants) from the solvent mixture. The precipitated nanostructures are then separated from the solvent mixture (e.g., by centrifuging), thereby removing excess organic surfactant from the nanostructures. Optionally, the precipitated nanostructures can be washed with the solvent mixture one or more additional times, e.g., if analysis determines that the nanostructure preparation still contains an undesirable quantity of excess surfactant.

Additionally, any excess organic salts can be removed from the nanocrystal reaction mixture by performing a pyridine exchange on the nanocrystals in the nanocrystal reaction mixture, and precipitating the organic salts while leaving the nanocrystals in solution. The pyridine exchange is performed, for example, by heating the nanocrystal reaction mixture to 150° C. for about 1 hour.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of synthesizing an organic composition that facilitates charge transfer for use in a nanostructure-containing device, the method comprising:
   a) providing a body structure comprising a conjugated organic precursor, wherein the conjugated organic precursor comprises at least three positions available for attachment of substituent modules;
   b) providing a first substituent module comprising a thiophene derivative which comprises diethylphosphite;
   c) providing a second substituent module, wherein the second substituent module comprises an alkyne derivative comprising between three and 22 carbons; and
   d) optionally providing a third substituent module, wherein the optional third substituent module comprises an alkyl derivative comprising between one and 22 carbons;
   e) coupling the first substituent module at a first position, coupling the second substituent module at a second position, and optionally coupling the third substituent module at a third position, thereby synthesizing the organic composition, wherein coupling the first substituent module comprises performing a palladium-catalyzed phosphite-aryl coupling;
   wherein coupling of the modules to the body structure does not destroy an electronic conjugation of the body structure, and,
   wherein at least one substituent of the first, second or third substituent modules is capable of binding to a nanostructure surface or is already bound to a nanostructure surface.

2. The method of claim 1, wherein the first substituent module comprises an aryl-thiophene moiety and wherein coupling the first substituent module comprises:
   a) performing a Stille coupling to form an iodinated intermediate;
   b) exchanging an iodine substituent of the iodinated intermediate for a TMS substituent; and,
   c) coupling a phosphite group to the aryl portion of the bound first substituent module via a palladium-catalyzed mechanism.

3. A method of synthesizing an organic composition that facilitates charge transfer for use in a nanostructure-containing device, the method comprising:
   a) providing a body structure comprising a conjugated organic precursor, wherein the conjugated organic precursor comprises at least three positions available for attachment of substituent modules;
   b) providing a head group comprising a first substituent module, wherein the first substituent module comprises a phosphonic acid derivative, a carboxylic acid derivative, an amine derivative, a phosphine derivative, a thiol derivative, a thiophene derivative, or a combination thereof;
   c) coupling the head group to an external surface of a nanocrystal, thereby providing a nanocrystal-bound composition;
   d) providing a second substituent module, wherein the second substituent module comprises an alkyne derivative comprising between three and 22 carbons; and
   e) optionally providing a third substituent module, wherein the optional third substituent module comprises an alkyl derivative comprising between one and 22 carbons;
   f) coupling the first substituent module at a first position, coupling the second substituent module at a second position, and optionally coupling the third substituent module at a third position, thereby synthesizing the organic composition; and
   wherein coupling of the modules to the body structure does not destroy an electronic conjugation of the body structure.

4. The method of claim 3, wherein the nanostructure comprises CdTe or InP.

5. The method of claim 3, wherein coupling the head group to the external surface of the nanostructure comprises interacting one or more free electrons in the head group with proximal metal moieties of the nanostructure.

6. The method of claim 3, further comprising:
   g) polymerizing the organic composition after coupling the composition to the nanocrystal surface, thereby forming a polymerized organic composition.

* * * * *